(12) United States Patent
Ryu et al.

(10) Patent No.: US 11,123,041 B2
(45) Date of Patent: *Sep. 21, 2021

(54) ULTRASOUND DIAGNOSIS APPARATUS FOR SELF-DIAGNOSIS AND REMOTE-DIAGNOSIS, AND METHOD OF OPERATING THE ULTRASOUND DIAGNOSIS APPARATUS

(71) Applicant: SAMSUNG ELECTRONICS CO., LTD., Suwon-si (KR)

(72) Inventors: Jae-young Ryu, Suwon-si (KR);
Dong-ki Kim, Seoul (KR);
Young-hwan Kim, Hwaseong-si (KR);
Min-woo Seo, Seongnami-si (KR);
Jei-young Lee, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 146 days.

This patent is subject to a terminal disclaimer.

(21) Appl. No.: 16/294,412

(22) Filed: Mar. 6, 2019

(65) Prior Publication Data
US 2019/0200955 A1 Jul. 4, 2019

Related U.S. Application Data

(63) Continuation-in-part of application No. 15/500,398, filed as application No. PCT/KR2015/009098 on Aug. 28, 2015, now Pat. No. 10,660,607.

(30) Foreign Application Priority Data

Aug. 28, 2014 (KR) .................. 10-2014-0113348

(51) Int. Cl.
*A61B 8/00* (2006.01)
*G16H 30/40* (2018.01)
(Continued)

(52) U.S. Cl.
CPC .............. *A61B 8/4263* (2013.01); *A61B 8/14* (2013.01); *A61B 8/4427* (2013.01); *A61B 8/463* (2013.01);
(Continued)

(58) Field of Classification Search
CPC ...... G16H 40/63; G16H 30/40; A61B 8/4263; A61B 8/54; A61B 8/463; A61B 8/56;
(Continued)

(56) References Cited

U.S. PATENT DOCUMENTS 6,705,992 B2   3/2004   Gatzke
7,806,824 B2   10/2010  Ohtake
(Continued)

FOREIGN PATENT DOCUMENTS

CN   1608592 A   4/2005
CN   101730505 A  6/2010
(Continued)

OTHER PUBLICATIONS

Communication dated Apr. 2, 2020, issued by the State Intellectual Property Office of P.R. China in counterpart Chinese Application No. 201580045417.2.
(Continued)

*Primary Examiner* — Catherine M Voorhees
(74) *Attorney, Agent, or Firm* — Sughrue Mion, PLLC

(57) ABSTRACT

An ultrasound diagnosis apparatus and method enabling general users to easily acquire ultrasound images even when the users are unskilled at using ultrasound diagnosis apparatuses, including a probe comprising an analog front-end controller, an analog-to-digital converter, a field-programmable gate array, and a communication module, the probe being configured to acquire ultrasound data of an object.

15 Claims, 47 Drawing Sheets

(51) Int. Cl.
 *A61B 8/08* (2006.01)
 *A61B 8/14* (2006.01)
 *G16H 40/63* (2018.01)

(52) U.S. Cl.
 CPC .............. *A61B 8/488* (2013.01); *A61B 8/54* (2013.01); *A61B 8/56* (2013.01); *G16H 30/40* (2018.01); *G16H 40/63* (2018.01)

(58) Field of Classification Search
 CPC ......... A61B 8/488; A61B 8/4427; A61B 8/14; A61B 8/5223; A61B 8/565
 See application file for complete search history.

(56) References Cited

U.S. PATENT DOCUMENTS

| | | | |
|---|---|---|---|
| 9,005,127 B2 | 4/2015 | Azuma | |
| 9,451,930 B2 | 9/2016 | Abe | |
| 9,471,981 B2 | 10/2016 | Arai et al. | |
| 9,480,457 B2 | 11/2016 | Kondou | |
| 10,660,607 B2* | 5/2020 | Ryu | A61B 8/06 |
| 2005/0119569 A1* | 6/2005 | Ohtake | A61B 8/00 600/437 |
| 2008/0146277 A1 | 6/2008 | Anglin et al. | |
| 2008/0262356 A1 | 10/2008 | Chalana et al. | |
| 2010/0174192 A1 | 7/2010 | Azuma | |
| 2012/0203107 A1 | 8/2012 | Kim | |
| 2012/0220876 A1 | 8/2012 | Hwang | |
| 2013/0123635 A1* | 5/2013 | Wegner | A61B 8/4494 600/447 |
| 2014/0018661 A1 | 1/2014 | Tsujita et al. | |
| 2016/0119529 A1* | 4/2016 | Stolka | A61B 8/52 348/211.1 |
| 2016/0157827 A1* | 6/2016 | Kristoffersen | A61B 8/4494 600/447 |
| 2018/0344286 A1* | 12/2018 | Mienkina | A61B 5/4848 |
| 2020/0182989 A1* | 6/2020 | Freeman | G01S 7/52095 |

FOREIGN PATENT DOCUMENTS

| | | |
|---|---|---|
| CN | 102626324 A | 8/2012 |
| CN | 103781426 A | 5/2014 |
| JP | 2002263101 A | 9/2002 |
| JP | 2006505294 A | 2/2006 |
| JP | 2009207800 A | 9/2009 |
| JP | 2010-201049 A | 9/2010 |
| JP | 2010233921 A | 10/2010 |
| JP | 2012-91042 A | 5/2012 |
| JP | 2012-147858 A | 8/2012 |
| JP | 5027922 B2 | 9/2012 |
| JP | 5410629 B1 | 2/2014 |
| JP | 2016-501605 A | 1/2016 |
| KR | 1020100057341 A | 5/2010 |
| WO | 2008/149573 A1 | 12/2008 |
| WO | 2012/124341 A1 | 9/2012 |
| WO | 2014/097090 A1 | 6/2014 |

OTHER PUBLICATIONS

Office Action dated May 7, 2019 by the Japanese Patent Office in counterpart Japanese Patent Application No. 2017-502779.
Office Action dated Jul. 2, 2019 by the State Intellectual Property Office of P.R. China in counterpart Chinese Patent Application No. 201580045417.2.
Communication dated Apr. 9, 2018 issued by the European Patent Office in counterpart European Patent Application No. 15835199.9.
Communication dated Dec. 16, 2016, issued by the Korean Intellectual Property Office in counterpart Korean Application No. 10-2014-0113348.
Communication dated May 31, 2016, issued by the Korean Intellectual Property Office in counterpart Korean Application No. 10-2014-0113348.
Communication dated Nov. 27, 2015, issued by the Korean Intellectual Property Office in counterpart Korean Application No. 10-2014-0113348.
International Search Report and Written Opinion dated Dec. 15, 2015, issued by the International Searching Authority in counterpart International Application No. PCT/KR2015/009098 (PCT/ISA/220, 210, and 237).

* cited by examiner

ULTRASOUND DIAGNOSIS APPARATUS FOR SELF-DIAGNOSIS AND REMOTE-DIAGNOSIS, AND METHOD OF OPERATING THE ULTRASOUND DIAGNOSIS APPARATUS

CROSS-REFERENCE TO RELATED APPLICATIONS

This application is a continuation-in-part of U.S. application Ser. No. 15/500,398 filed on Jan. 30, 2017, which is a National Stage Entry of International Application No. PCT/KR2015/009098 filed Aug. 28, 2015, which claims priority from Korean Patent Application No. 10-2014-0113348 filed Aug. 28, 2014, the disclosures of which are incorporated herein in their entireties by reference.

BACKGROUND

1. Field

One or more embodiments relate to an ultrasound diagnosis apparatus and a method of operating the ultrasound diagnosis apparatus. More particularly, one or more embodiments relate to an ultrasound diagnosis apparatus which a user may use to conveniently acquire an ultrasound image at home even when he or she is unskilled at using the ultrasound diagnosis apparatus, and an ultrasound diagnosis method of conveniently acquiring an ultrasound image at a user's home by using the ultrasound diagnosis apparatus. One or more embodiments also relate to an ultrasound diagnosis apparatus and method in which an ultrasound image acquired by the ultrasound diagnosis apparatus is transmitted to a skilled user remotely located away from the ultrasound diagnosis apparatus so that the ultrasound image may be used in diagnosis.

2. Description of the Related Art

Ultrasound diagnosis apparatuses transmit an ultrasound signal generated by a transducer of a probe to an object and receive information regarding an ultrasound echo signal reflected from the object, thereby obtaining an image of a part inside the object. In particular, ultrasound diagnosis apparatuses are used for medical purposes, such as observation of the inside of an object, detection of foreign substances inside the object, and diagnosis of damage thereof. Such ultrasound diagnosis apparatuses have various advantages, including stability, real-time display, and safety because there is no exposure to radiation, compared to X-ray apparatuses, and thus, the ultrasound diagnosis apparatuses are commonly used together with other image diagnosis apparatuses.

In this connection, an ultrasound diagnosis apparatus and method enabling a user to easily acquire an ultrasound image even when the user is not skilled in ultrasound diagnosis apparatuses need to be provided.

Since ultrasound diagnosis apparatuses are large and expensive equipment, general users other than skilled persons working for professional organizations have difficulty in utilizing the ultrasound diagnosis apparatuses. However, ultrasound diagnosis apparatuses have currently become miniaturized with developments in technology, and prices of ultrasound diagnosis apparatuses have reached low enough levels for general users to purchase the ultrasound diagnosis apparatuses. When a general user utilizes an ultrasound diagnosis apparatus, he or she can obtain an ultrasound image at home. Thus, even general users can simply observe the inside of their bodies and can be diagnosed remotely by providing acquired ultrasound images to a remote skilled user. However, since it is difficult to manipulate ultrasound diagnosis apparatuses, if a user has no background knowledge, it is difficult to position a probe at a body part that is to be measured, and it is also difficult to set suitable image modes according to body parts. In other words, since general users are not provided with an interface that can be easily used by the general users, availability of ultrasound diagnosis apparatuses degrades.

Recently, ultrasound imaging systems have been developed to reduce system hardware and computational complexity with image quality comparable to conventional cart-based ultrasound imaging systems. Most efforts have focused on using programmable methodologies, such as field-programmable gate arrays (FPGAs) and digital signal processor (DSP) architectures. For example, a fully programmable system for ultrasound imaging using a combination of a low-cost FPGA and a DSP integrated with a 32-channel dynamic receive beamformer has been introduced. However, this hybrid architecture fails to satisfy the requirements of conventional B-mode ultrasound imaging based on its limited data transfer rate. Further, the foregoing architectures are insufficient to perform high-resolution multi-beamforming, coded pulsing, and apodization.

Other efforts have introduced a minimized system using a single low-cost FPGA in a laptop-sized portable ultrasound imaging system. The FPGA in such systems performs various types of ultrasound image processing, including transmit and dynamic receive beamforming, mid-processing, and back-end processing. However, only 16 channels of beamformers are capable of being implemented into the system based on hardware limitations. Thus, the image quality, including the contrast resolution, is much lower than that of conventional ultrasound imaging systems, which commonly have more than 32-channels. Also, the system could not perform any other imaging modes except B-mode imaging.

In order to support point-of-care (POC) diagnosis, a variety of commercially-available and portable ultrasound imaging systems have been introduced. However, these systems are insufficient for POC diagnosis due to relatively greater weights and sizes, limited display sizes and pixel resolutions, limited types of support for imaging modes, limited battery time, among other deficiencies.

Further, other portable ultrasound imaging systems use application-specific integrated circuits (ASICs) which have similar form factors comparable with a personal digital assistance (PDA). However, in these conventional portable ultrasound imaging devices, the application of the system is inevitably limited because the system employs specific connectors and processing cores for using conventional probes. Thus, the probe is limited in adaptation for widespread usage. Demands for portable ultrasound systems are expected to integrate most features of traditional cart-based systems with comparable performance. For example, color (C), pulsed-wave (PW), and continuous-wave (CW) Doppler modes should be implemented by portable imaging systems. Additionally, portable systems might adapt semiconductor technologies to provide greater solutions, which can meet performance requirements while also providing reduced size and power consumption.

In this way, some embodiments herein provide a probe for a portable ultrasound imaging system. To achieve high resolution ultrasound images, some embodiments herein provide 128-channel analog front-end controller (AFEC) and analog-to-digital converter (ADC) chipsets fabricated using complementary metal-oxide-semiconductor (CMOS) processes. The probe employs an FPGA to perform digital beamforming and pre-processing for ultrasound signals, and a wireless module to connect to an external device (e.g., a mobile phone or tablet PC) for user convenience. Some embodiments herein provide a probe with a 300 gram weight, and that demonstrates real-time B-mode images. Embodiments herein support CW and Doppler modes, and are expected to be used by any person without training in ultrasound operational protocols in a multitude of scenarios.

Additionally, some embodiments herein provide a 128-channel full digital beamforming wireless handheld probe for ultrasound medical imaging. The probe system includes a 128-channel analog front-end controller (AFEC), a 128-channel analog-to-digital converter (ADC), a signal processing field-programmable gate array (FPGA), and a wireless module to achieve high resolution image quality as well as small form factor to integrate in a compact system. The AFEC chip is fabricated using a 0.35 μm high voltage (HV) CMOS process, and is configured to perform 76.8 $V_{pp}$ of pulse in a transmitting mode and 47 dB of gain range with a discrete gain step of 1.5 dB in a receiving mode. Additionally, the ADC chip was fabricated using a 0.13 μm standard CMOS process with a signal-to-noise and distortion ratio (SNDR) of 67 dB at an effective number of bits (ENOB) of 10.57 bits. The FPGA is configured to support precise and flexible digital beamforming combined with the AFEC and ADC chipsets. Fabricated chips and the FPGA are integrated on a printed circuit board (PCB) with a size of 60 mm (width)×150 mm (length)×50 mm (height) and a weight of about 300 grams. The probe is configured to provide real-time B-mode images at a frame rate of 30 frames per second.

SUMMARY

One or more embodiments include an ultrasound diagnosis apparatus and method enabling general users to easily acquire ultrasound images even when the users have no background knowledge, and a computer-readable storage medium having the ultrasound diagnosis method recorded thereon.

Additional aspects will be set forth in part in the description which follows and, in part, will be apparent from the description, or may be learned by practice of the presented embodiments.

According to one or more embodiments of the disclosure, an ultrasound diagnosis apparatus includes a probe configured to acquire ultrasound data of an object; an image generation unit configured to generate an ultrasound image of the object by using the ultrasound data; a probe location acquisition unit configured to acquire a location of the probe on the object; a display unit configured to display the location of the probe and a reference location on an image representing the object; and a control unit configured to determine whether the location of the probe corresponds to the reference location.

The ultrasound diagnosis apparatus may further include a storage unit configured to map a plurality of locations of the probe with a plurality of reference ultrasound images and store a result of the mapping. The probe location acquisition unit may compare the ultrasound image with the plurality of reference ultrasound images, select one from among the plurality of reference ultrasound images based on a result of the comparison, and acquire a location corresponding to the selected reference ultrasound image as the location of the probe.

The ultrasound diagnosis apparatus may further include a photographing unit configured to photograph the probe and the object. The probe location acquisition unit may detect an area corresponding to the probe and an area corresponding to the object from an image captured by photographing the probe and the object, and acquire the location of the probe based on a location of the area corresponding to the probe with respect to the area corresponding to the object.

When it is determined that the location of the probe does not correspond to the reference location, the control unit may determine a movement path to be taken by the probe to move to the reference location, and the display unit may display the movement path from the location of the probe to the reference location on the image representing the object.

When the location of the probe corresponds to the reference location, the control unit may control the display unit to display an image representing that the location of the probe corresponds to the reference location.

When the location of the probe corresponds to the reference location, the control unit may control the probe to transmit an ultrasound signal to the object and receive an echo signal from the object to acquire the ultrasound data.

The ultrasound diagnosis apparatus may further include a communication unit configured to transmit the ultrasound image to an external device when the location of the probe corresponds to the reference location.

The ultrasound diagnosis apparatus may further include an input unit configured to receive a user input of selecting at least one location from among a plurality of locations on the object, and the control unit may determine the selected location as the reference location.

The ultrasound diagnosis apparatus may further include a communication unit configured to receive, from an external device, information that is used to determine the reference location, and the control unit may determine the reference location based on the received information.

The ultrasound diagnosis apparatus may further include a communication unit configured to transmit at least one selected from the location of the probe, the reference location, the ultrasound image, and an image displayed on the display unit to an external device.

The communication unit may receive information that is used to generate the ultrasound image, from the external device. The control unit may control at least one selected from the probe and the image generation unit, based on the received information.

According to one or more embodiments of the disclosure, a method of operating an ultrasound diagnosis apparatus including a probe acquiring ultrasound data of an object and an image generation unit generating an ultrasound image of the object by using the ultrasound data includes acquiring a location of the probe on the object; displaying the location of the probe and a reference location on an image representing the object; and determining whether the location of the probe corresponds to the reference location.

The method may further include mapping a plurality of locations of the probe with a plurality of reference ultrasound images and storing a result of the mapping. The acquiring of the location of the probe may include comparing the ultrasound image with the plurality of reference ultrasound images; selecting one reference ultrasound image from the plurality of reference ultrasound images, based on a result of the comparing; and acquiring a location corresponding to the selected reference ultrasound image as the location of the probe.

The method may further include photographing the probe and the object, and the acquiring of the location of the probe may include detecting an area corresponding to the probe and an area corresponding to the object from an image captured by photographing the probe and the object; and acquiring the location of the probe based on a location of the area corresponding to the probe with respect to the area corresponding to the object.

The determining whether the location of the probe corresponds to the reference location may include determining a movement path to be taken by the probe to move to the reference location when it is determined that the location of the probe does not correspond to the reference location; and displaying the movement path from the location of the probe to the reference location on the image representing the object.

The method may further include displaying an image representing that the location of the probe corresponds to the reference location, when the location of the probe corresponds to the reference location.

The method may further include transmitting an ultrasound signal to the object and receiving an echo signal from the object to acquire the ultrasound data, when it is determined that the location of the probe corresponds to the reference location.

The method may further include transmitting the ultrasound image of the object to an external device when it is determined that the location of the probe corresponds to the reference location.

The method may further include receiving a user input of selecting at least one location from among a plurality of locations on the object; and determining the selected location as the reference location.

The method may further include receiving, from an external device, information that is used to determine the reference location; and determining the reference location based on the received information.

The method may further include transmitting at least one selected from the location of the probe, the reference location, the ultrasound image, and an image displayed on display unit to an external device.

The method may further include receiving information that is used to generate the ultrasound image, from the external device; and controlling at least one selected from the probe and the image generation unit, based on the received information.

According to one or more embodiments of the disclosure, a non-transitory computer-readable recording medium has recorded thereon a program for executing the above-described method.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION OF EMBODIMENTS

Figure 1:
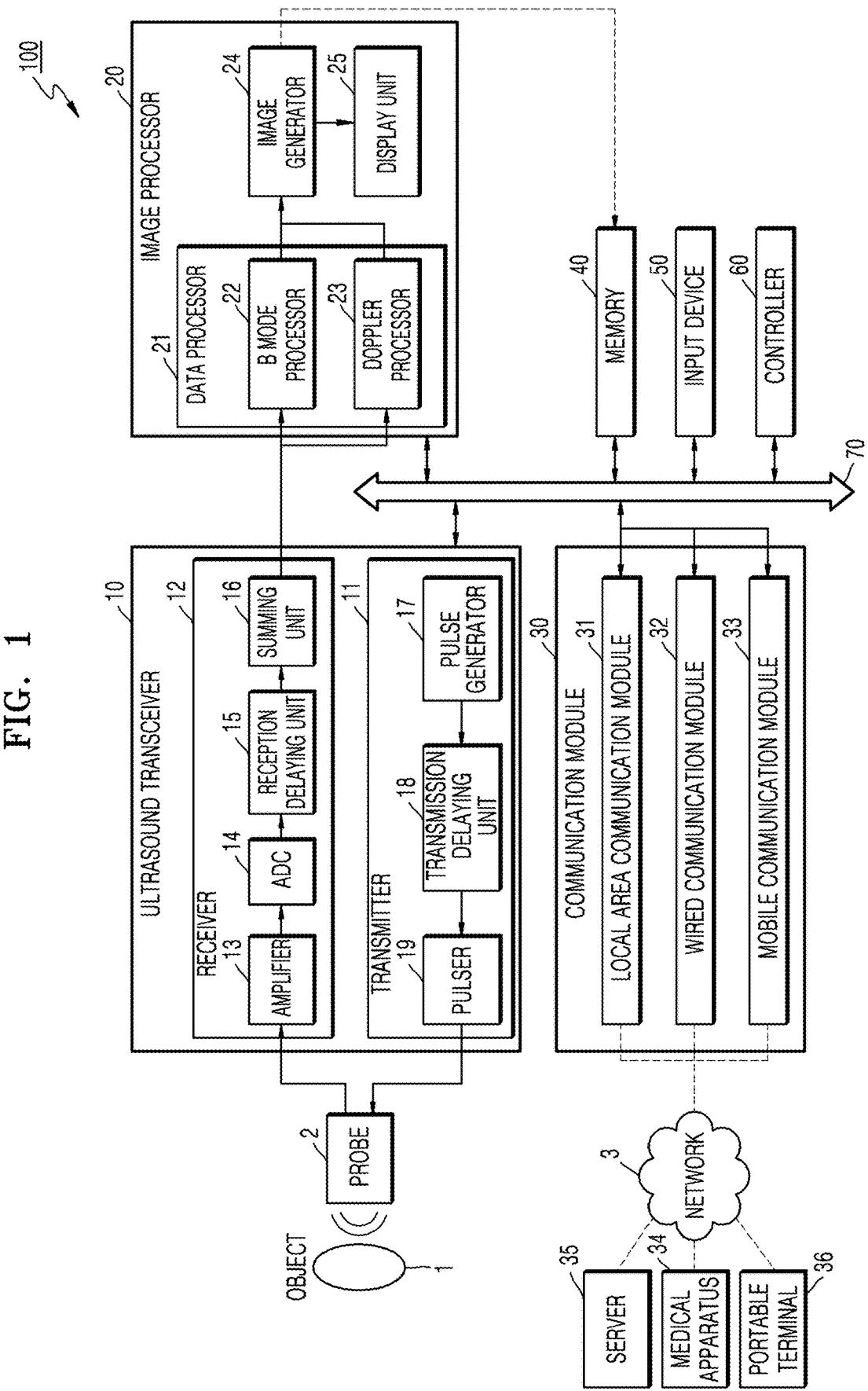
FIG. 1 is a block diagram of an ultrasound diagnosis apparatus according to an embodiment of the disclosure.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

Throughout the specification, it will also be understood that when a component "includes" an element, unless there is another opposite description thereto, it should be understood that the component does not exclude another element and may further include another element. In addition, terms such as " . . . unit", " . . . module", or the like refer to units that perform at least one function or operation, and the units may be implemented as hardware or software or as a combination of hardware and software.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism.

Also, a "user" may be, but is not limited to, a medical expert such as a doctor, a nurse, a medical laboratory technologist, a medial image expert, or a technician who repairs a medical apparatus. Hereinafter, embodiments will be described in detail with reference to the accompanying drawings.

FIG. 1 is a block diagram showing a configuration of an ultrasound diagnosis apparatus according to an embodiment.

Referring to FIG. 1, the ultrasound diagnosis apparatus 100 may include a probe 2, an ultrasound transceiver 10, an image processor 20, a communication module 30, display unit 25, a memory 40, an input device 50, and a controller 60, which may be connected to one another via buses 70.

The ultrasound diagnosis apparatus 100 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 2 transmits ultrasound waves to an object 1 in response to a driving signal applied by the ultrasound transceiver 10 and receives echo signals reflected by the object 1. The probe 2 includes a plurality of transducers, and the plurality of transducers oscillate in response to electric signals and generate acoustic energy, that is, ultrasound waves. Furthermore, the probe 2 may be connected to the main body of the ultrasound diagnosis apparatus 100 by wire or wirelessly, and according to embodiments, the ultrasound diagnosis apparatus 100 may include a plurality of probes 2.

A transmitter 11 supplies a driving signal to the probe 2. The transmitter 11 includes a pulse generator 17, a transmission delaying unit 18, and a pulser 19. The pulse generator 17 generates pulses for forming transmission ultrasound waves based on a predetermined pulse repetition frequency (PRF), and the transmission delaying unit 18 delays the pulses by delay times necessary for determining transmission directionality. The pulses which have been delayed correspond to a plurality of piezoelectric vibrators included in the probe 2, respectively. The pulser 19 applies a driving signal (or a driving pulse) to the probe 2 based on timing corresponding to each of the pulses which have been delayed.

A receiver 12 generates ultrasound data by processing echo signals received from the probe 2. The receiver 12 may include an amplifier 13, an analog-to-digital converter (ADC) 14, a reception delaying unit 15, and a summing unit 16. The amplifier 13 amplifies echo signals in each channel, and the ADC 14 performs analog-to-digital conversion with respect to the amplified echo signals. The reception delaying unit 15 delays digital echo signals output by the ADC 1124 by delay times necessary for determining reception directionality, and the summing unit 16 generates ultrasound data by summing the echo signals processed by the reception delaying unit 15. In some embodiments, the receiver 12 may not include the amplifier 13. In other words, if the sensitivity of the probe 2 or the capability of the ADC 14 to process bits is enhanced, the amplifier 13 may be omitted.

The image processor 20 generates an ultrasound image by scan-converting ultrasound data generated by the ultrasound transceiver 10 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 22 extracts B mode components from ultrasound data and processes the B mode components. An image generator 24 may generate an ultrasound image indicating signal intensities as brightness based on the extracted B mode components 22.

Similarly, a Doppler processor 23 may extract Doppler components from ultrasound data, and the image generator 24 may generate a Doppler image indicating a movement of an object as colors or waveforms based on the extracted Doppler components.

According to an embodiment, the image generator 24 may generate a three-dimensional (3D) ultrasound image via volume-rendering with respect to volume data and may also generate an elasticity image by imaging deformation of the object 1 due to pressure. Furthermore, the image generator 24 may display various pieces of additional information in an ultrasound image by using text and graphics. In addition, the generated ultrasound image may be stored in the memory 40.

A display 25 displays the generated ultrasound image. The display 25 may display not only an ultrasound image, but also various pieces of information processed by the ultrasound diagnosis apparatus 100 on a screen image via a graphical user interface (GUI). In addition, the ultrasound diagnosis apparatus 100 may include two or more displays 25 according to embodiments.

The communication module 30 is connected to a network 3 by wire or wirelessly to communicate with an external device or a server. The communication module 30 may exchange data with a hospital server or another medical apparatus in a hospital, which is connected thereto via a PACS. Furthermore, the communication module 30 may perform data communication according to the digital imaging and communications in medicine (DICOM) standard.

The communication module 30 may transmit or receive data related to diagnosis of an object, e.g., an ultrasound image, ultrasound data, and Doppler data of the object, via the network 3 and may also transmit or receive medical images captured by another medical apparatus, e.g., a computed tomography (CT) apparatus, a magnetic resonance imaging (MRI) apparatus, or an X-ray apparatus. Furthermore, the communication module 30 may receive information about a diagnosis history or medical treatment schedule of a patient from a server and utilizes the received information to diagnose the patient. Furthermore, the communication module 30 may perform data communication not only with a server or a medical apparatus in a hospital, but also with a portable terminal of a medical doctor or patient.

The communication module 30 is connected to the network 3 by wire or wirelessly to exchange data with a server 35, a medical apparatus 34, or a portable terminal 36. The communication module 30 may include one or more components for communication with external devices. For example, the communication module 1300 may include a local area communication module 31, a wired communication module 32, and a mobile communication module 33.

The local area communication module 31 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra-wideband (UWB), infrared data association (IrDA), Bluetooth low energy (BLE), and near field communication (NFC).

The wired communication module 32 refers to a module for communication using electric signals or optical signals. Examples of wired communication techniques according to an embodiment may include communication via a twisted pair cable, a coaxial cable, an optical fiber cable, and an Ethernet cable.

The mobile communication module 33 transmits or receives wireless signals to or from at least one selected from a base station, an external terminal, and a server on a mobile communication network. The wireless signals may be voice call signals, video call signals, or various types of data for transmission and reception of text/multimedia messages.

The memory 40 stores various data processed by the ultrasound diagnosis apparatus 100. For example, the memory 40 may store medical data related to diagnosis of an object, such as ultrasound data and an ultrasound image that are input or output, and may also store algorithms or programs which are to be executed in the ultrasound diagnosis apparatus 100.

The memory 40 may be any of various storage media, e.g., a flash memory, a hard disk drive, EEPROM, etc. Furthermore, the ultrasound diagnosis apparatus 100 may utilize web storage or a cloud server that performs the storage function of the memory 40 online.

The input device 50 refers to a means via which a user inputs data for controlling the ultrasound diagnosis apparatus 100. The input device 50 may include hardware components, such as a keypad, a mouse, a touch panel, a touch screen, and a jog switch. However, embodiments are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 60 may control all operations of the ultrasound diagnosis apparatus 100. In other words, the controller 60 may control operations among the probe 2, the ultrasound transceiver 10, the image processor 20, the communication module 30, the memory 40, and the input device 50 shown in FIG. 1.

All or some of the probe 2, the ultrasound transceiver 10, the image processor 20, the communication module 30, the memory 40, the input device 50, and the controller 60 may be implemented as software modules. However, embodiments of the disclosure are not limited thereto, and some of the components stated above may be implemented as hardware modules. Furthermore, at least one selected from the ultrasound transceiver 10, the image processor 20, and the communication module 30 may be included in the controller 60. However, embodiments of the disclosure are not limited thereto.

Figure 2:
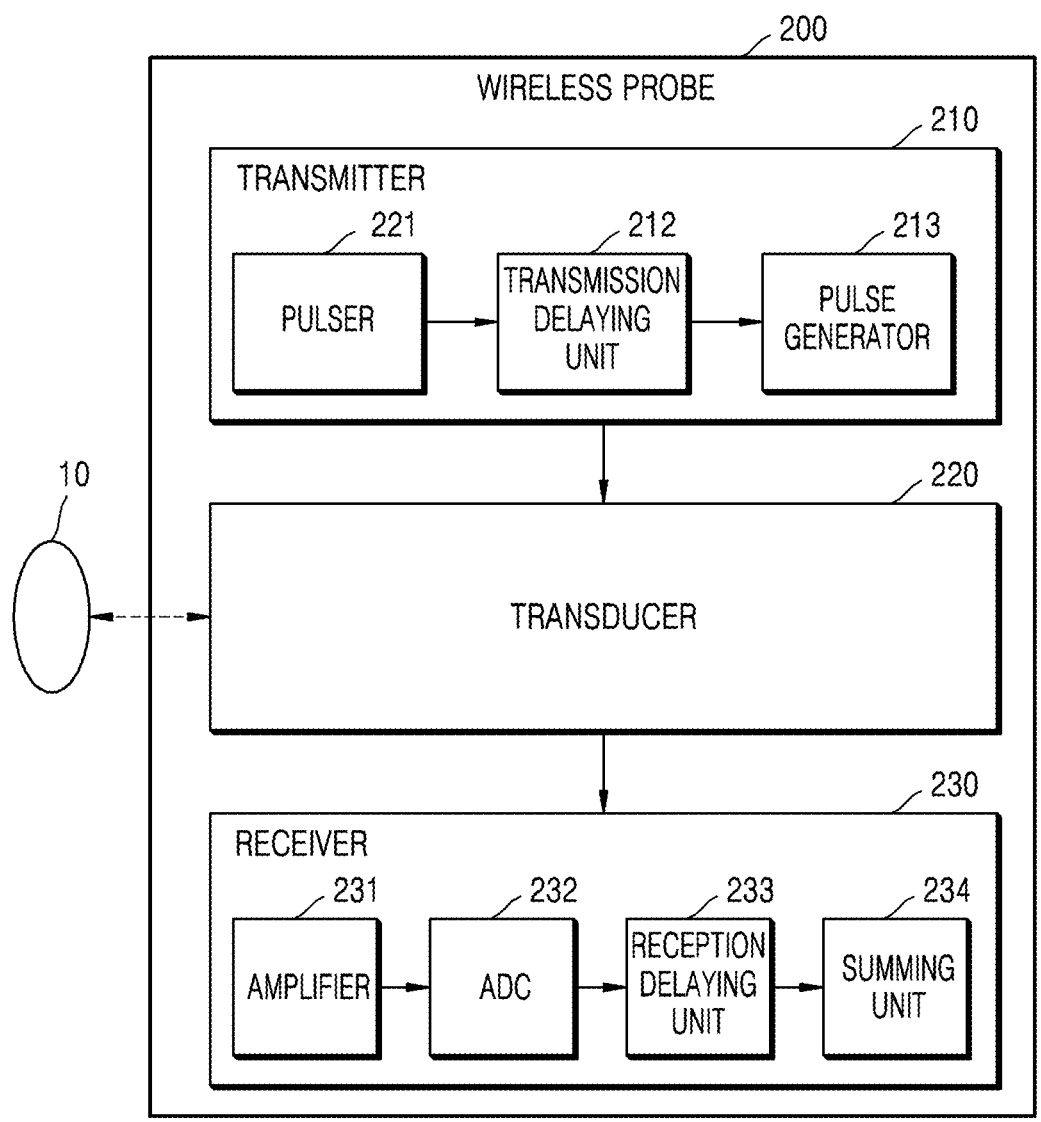
FIG. 2 is a block diagram of a wireless probe according to an embodiment of the disclosure.

FIG. 2 is a block diagram showing a configuration of a wireless probe according to an embodiment.

As described above with reference to FIG. 1, the wireless probe 200 may include a plurality of transducers, and, according to embodiments, may include some or all of the components of the ultrasound transceiver 10 shown in FIG. 1.

The wireless probe 200 according to the embodiment shown in FIG. 2 includes a transmitter 210, a transducer 220, and a receiver 230. Since descriptions thereof are given above with reference to FIG. 1, detailed descriptions thereof will be omitted here. In addition, according to embodiments, the wireless probe 200 may selectively include a reception delaying unit 233 and a summing unit 234. The transmitter 210 includes a pulser 221, a transmission delaying unit 212, and a pulse generator 213. The receiver 230 includes an amplifier 231, an ADC 232, the reception delaying unit 233, and the summing unit 234.

The wireless probe 200 may transmit ultrasound signals to the object 1, receive echo signals from the object 10, generate ultrasound data, and wirelessly transmit the ultrasound data to the ultrasound diagnosis apparatus 100 shown in FIG. 1.

Since ultrasound diagnosis apparatuses are large and expensive equipment, general users other than skilled persons working for professional organizations have difficulty in utilizing the ultrasound diagnosis apparatuses. However, ultrasound diagnosis apparatuses have currently become miniaturized with developments in technology, and the prices of ultrasound diagnosis apparatuses have reached low enough levels for general users to purchase the ultrasound diagnosis apparatuses. When a general user utilizes an ultrasound diagnosis apparatus, he or she can obtain an ultrasound image at home. Thus, even general users can simply observe the inside of their bodies and can be diagnosed remotely by providing acquired ultrasound images to a remote skilled user.

However, since it is difficult to manipulate ultrasound diagnosis apparatuses, if a user has no background knowledge, it is difficult to position a probe at a body part that is to be measured, and it is also difficult to set suitable image modes according to body parts.

An ultrasound imaging apparatus according to an embodiment of the disclosure enables even users unskilled at manipulating ultrasound imaging apparatuses to easily acquire an ultrasound image. An ultrasound diagnosis apparatus and method and a computer-readable storage medium having the ultrasound diagnosis method recorded thereon, according to an embodiment of the disclosure, will now be described in detail with reference to FIGS. 3-22.

The ultrasound diagnosis apparatus may construct an ultrasound image by acquiring a signal from a probe, and then may measure a length, an angle, an area, a volume, and the like of a particular organ, a particular structure, and the like on the ultrasound image. Via this measurement, the ultrasound diagnosis apparatus may acquire information about an abnormal part within a body or acquire information about a gestational age or the like. The ultrasound diagnosis apparatus is frequently used in a medical field because the ultrasound diagnosis apparatus is important means for assisting a medical diagnosis. Thus, if an inspection target is able to acquire an ultrasound image at home and transmit the ultrasound image to a remote medical expert, the inspection target can be diagnosed by the medical expert without visiting a hospital. For example, if an inspection target is able to acquire an ultrasound image at home and transmit the ultrasound image to a remote medical expert, the inspection target may acquire an ultrasound image at home immediately when he or she feels wrong with his or her body, and transmit the ultrasound image to a medical expert. Moreover, since the inspection target is able to acquire an ultrasound image at any time without restrictions on the time and the space, the inspection target is able to more minutely observe, for example, the progress of a body disease of the inspection target or the development process of a fetus.

Figure 3:
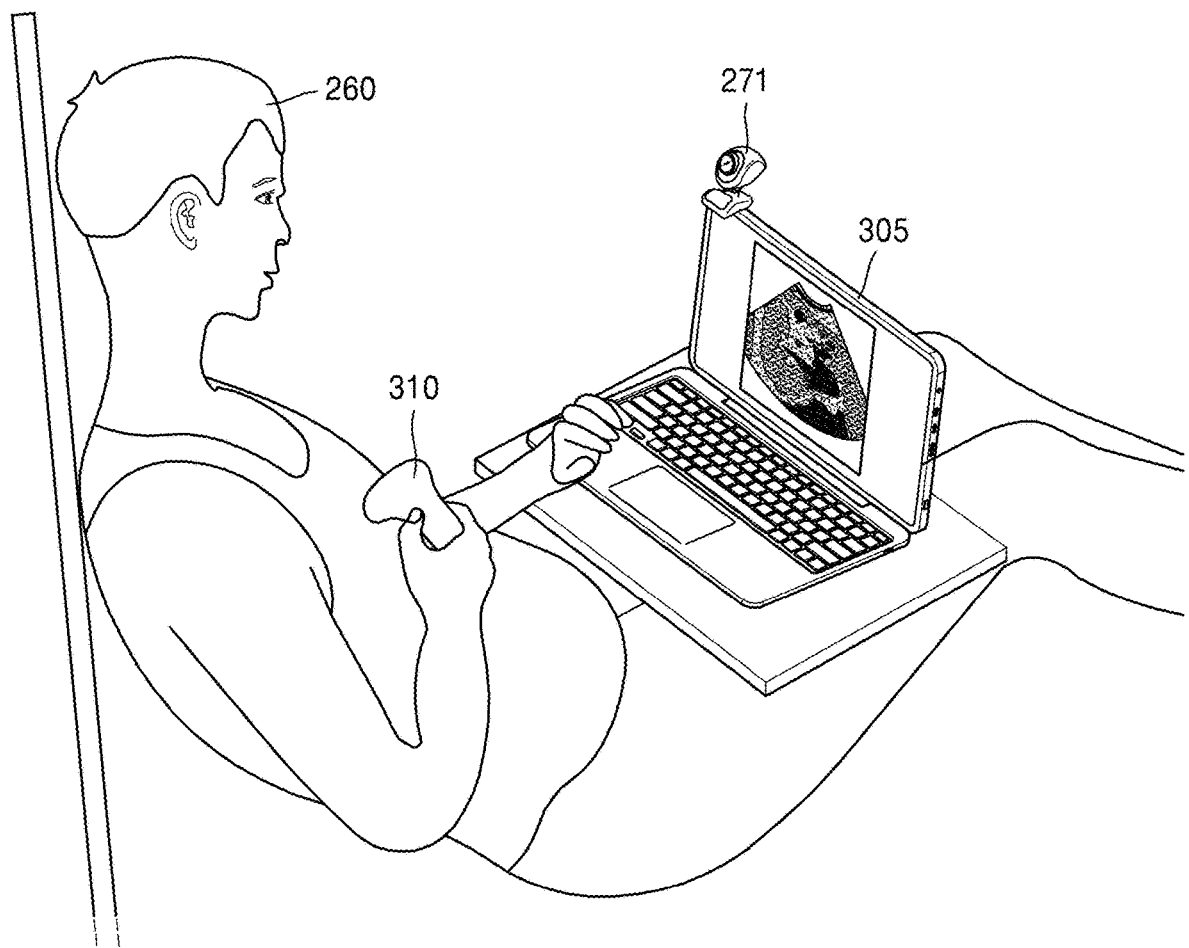
FIG. 3 schematically illustrates an ultrasound diagnosis apparatus being used by a user according to an embodiment of the disclosure.

FIG. 3 schematically illustrates use of an ultrasound diagnosis apparatus according to an embodiment of the disclosure. Since a probe 310 of FIG. 3 corresponds to the probe 2 of FIG. 1 or the probe 200 of FIG. 2, a repeated description thereof will be omitted here.

According to an embodiment of the disclosure, a user 260 may acquire an ultrasound image by using the probe 310. The probe 310 may be connected to a desktop 305 via wires or wirelessly.

FIG. 3 illustrates a case where the user 260 is identical to an inspection target. However, embodiments of the disclosure are not limited thereto, and the user 260 may be a person who uses the ultrasound diagnosis apparatus to diagnose an inspection target.

The user 260 may position the probe 310 at a body part of which an ultrasound image is desired to be acquired. The desktop 305 may acquire an ultrasound image, based on ultrasound data received from the probe 310. The acquired ultrasound image may be displayed on a display unit included in the desktop 305.

Since ultrasound waves are unable to pass through the air within bones or a stomach, the diagnosis accuracy of an acquired ultrasound image may vary according to a location of a probe. Thus, a user who is unskilled at using ultrasound diagnosis apparatuses has difficulty in ascertaining a suitable location at which a probe is to be positioned in order to obtain an ultrasound image of a desired internal part of a body. The ultrasound diagnosis apparatus according to an embodiment of the disclosure enables even an unskilled user to easily acquire an ultrasound image, by providing a "reference location" of a probe, which is suitable to obtain the ultrasound image.

The reference location denotes a location of a probe that is determined to be suitable to acquire an ultrasound image of a predetermined body part. The predetermined body part denotes a part of an inspection target, of which an ultrasound image may be acquired, such as a liver, a kidney, or a heart. For example, when a user desires to acquire an ultrasound image of a liver, the reference location may be the abdominal walls below the bone above the pit of the stomach and the right ribs.

The desktop 305 may acquire a relative location of the probe 310 with respect to the user 260, based on the acquired ultrasound image. The desktop 305 may include a photographing unit 271, and the photographing unit 271 may photograph the user 260 and the probe 310. The desktop 305 may acquire a relative location of the probe 310 with respect to the user 260, based on an image captured by the photographing unit 271.

The desktop 305 may display, to the user 260, a screen image including the location of the probe 310, the reference location, and a path from the location of the probe 310 to the reference location. The user 260 may position the probe 310 at the reference location along the path displayed on the display unit of the desktop 305. When the location of the probe 310 corresponds to the reference location, the desktop 305 may perform a predetermined operation. For example, the desktop 305 may inform the user 260 that the location of the probe 310 corresponds to the reference location, according to a predetermined method. The desktop 305 may also acquire an ultrasound image from the reference location. The desktop 305 may transmit the acquired ultrasound image to a remote medical expert. The remote medical expert may diagnose the inspection target, based on the received ultrasound image.

Figure 4:
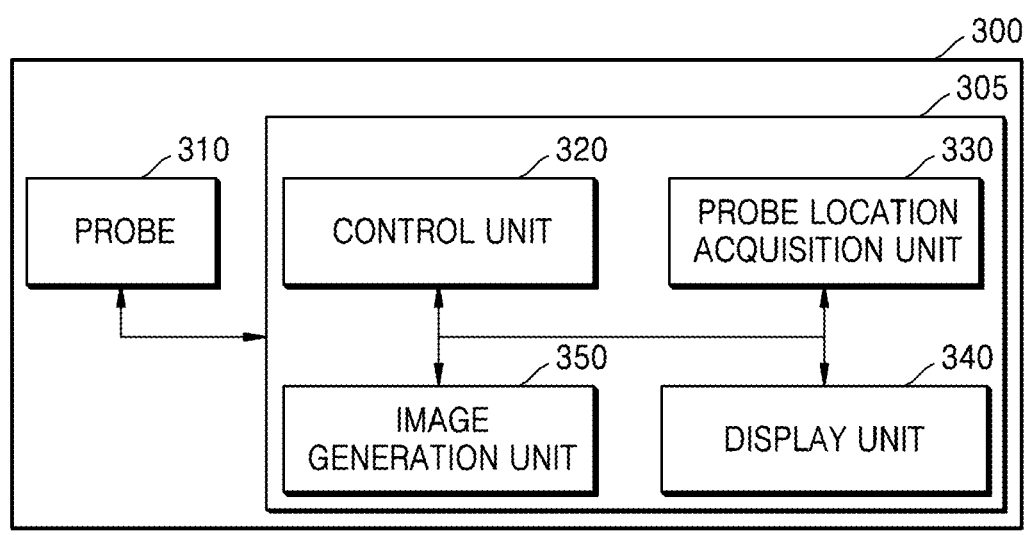
FIG. 4 is a block diagram of an ultrasound diagnosis apparatus according to an embodiment of the disclosure.

FIG. 4 is a block diagram of an ultrasound diagnosis apparatus 300 according to an embodiment of the disclosure.

Referring to FIG. 4, the ultrasound diagnosis apparatus 300 includes a probe 310 and a desktop 305. The desktop 305 includes a control unit 320, a probe location acquisition unit 330, a display unit 340, and an image generation unit 350. The probe 310, the control unit 320, the display unit 340, and the image generation unit 350 of FIG. 4 may respectively correspond to the probe 2, the control unit 60, the display unit 25, and the image generation unit 24 of FIG. 1. Alternatively, the probe 310 may correspond to the probe 200 of FIG. 2.

The probe 310 may be connected to the desktop 305 via wires or wirelessly. The probe 310 may transmit an ultrasound signal to a target according to a control signal transmitted by the desktop 305, and receive a response signal (or an ultrasound echo signal) reflected by the object to form a reception signal. The probe 310 may form ultrasound image data by focusing the reception signal, and may transmit the ultrasound image data to the desktop 305. The image generation unit 350 included in the desktop 305 may generate an ultrasound image by using the ultrasound image data received from the probe 310. The display unit 340 may display the generated ultrasound image.

The desktop 305 may not only be a general cart-type or portable ultrasound apparatus but also be a general computer including a processor, such as a tablet, a personal computer (PC), or a laptop. The desktop 305 may be connected to the probe 310 via wires or wirelessly. The desktop 305 may receive information from the probe 310 and perform various operations to acquire an ultrasound image.

The probe 310 acquires ultrasound data regarding the object. The image generation unit 350 generates an ultrasound image of the object by using the ultrasound data. The probe location acquisition unit 330 acquires a location of the probe 310 on the object. The display unit 340 displays the location of the probe 310 and a predetermined reference location on an image representing the object. The control unit 320 determines whether the location of the probe 310 corresponds to the reference location.

The image representing the object is an image that is displayed on the display unit 340, and may be an actual image obtained by photographing an inspection target. The image representing the object may be a figure that represents the body of the inspection target. Portions of the image representing the object may respectively correspond to body parts of the inspection target.

When it is determined that the location of the probe 310 does not correspond to the reference location, the control unit 320 may determine a movement path to be taken by the probe 310 to move to the reference location. The display unit 340 may also display the movement path from the location of the probe 310 to the reference location on the image representing the object. When it is determined that the location of the probe 310 corresponds to the reference location, the control unit 320 may control the display unit 340 to display an image representing that the location of the probe 310 corresponds to the reference location. When the location of the probe 310 corresponds to the reference location, the control unit 320 may also control the probe 310 to transmit the ultrasound signal to the object and receive an echo signal from the object to acquire the ultrasound data.

The probe location acquisition unit 330 may acquire a location of the probe 310 with respect to the object. The probe location acquisition 330 may acquire a spatial distance and a spatial direction from a predetermined reference point of the object to the probe 310 as the location of the probe 310, or divide the object into a plurality of areas and acquire as the location of the probe 310 an area that is closest to the probe 310 or an area that the probe 310 contacts. The location of the probe 310 may be displayed on the image representing the object.

Alternatively, the probe location acquisition unit 330 may include a location tracking sensor that is included in the probe 310 or attached to the probe 310.

For example, the probe location acquisition unit 330 may be located outside the probe 310. The probe location acquisition unit 330 may acquire the location of the probe 310 by tracking a movement of the probe 310 on the basis of a predetermined point within a space where the ultrasound diagnosis apparatus 300 is located. A method of tracking a movement of the probe 310 by using a location tracking sensor is well known, and thus a detailed description thereof will be omitted here.

For example, the ultrasound diagnosis apparatus 300 may further include an input unit for receiving a user input of selecting at least one location from a plurality of locations on the object, and the control unit 320 may determine the selected location as the reference location. The ultrasound diagnosis apparatus 300 may further include a communication unit for receiving, from an external device, information used to determine the reference location, and the control unit 320 may determine the reference location based on the received information.

The ultrasound diagnosis apparatus 300 may display the reference location on the display unit 340. A user may easily position the probe 310 at the reference location, based on the location of the probe 310 and the reference location displayed on the display unit 340.

Figure 5:
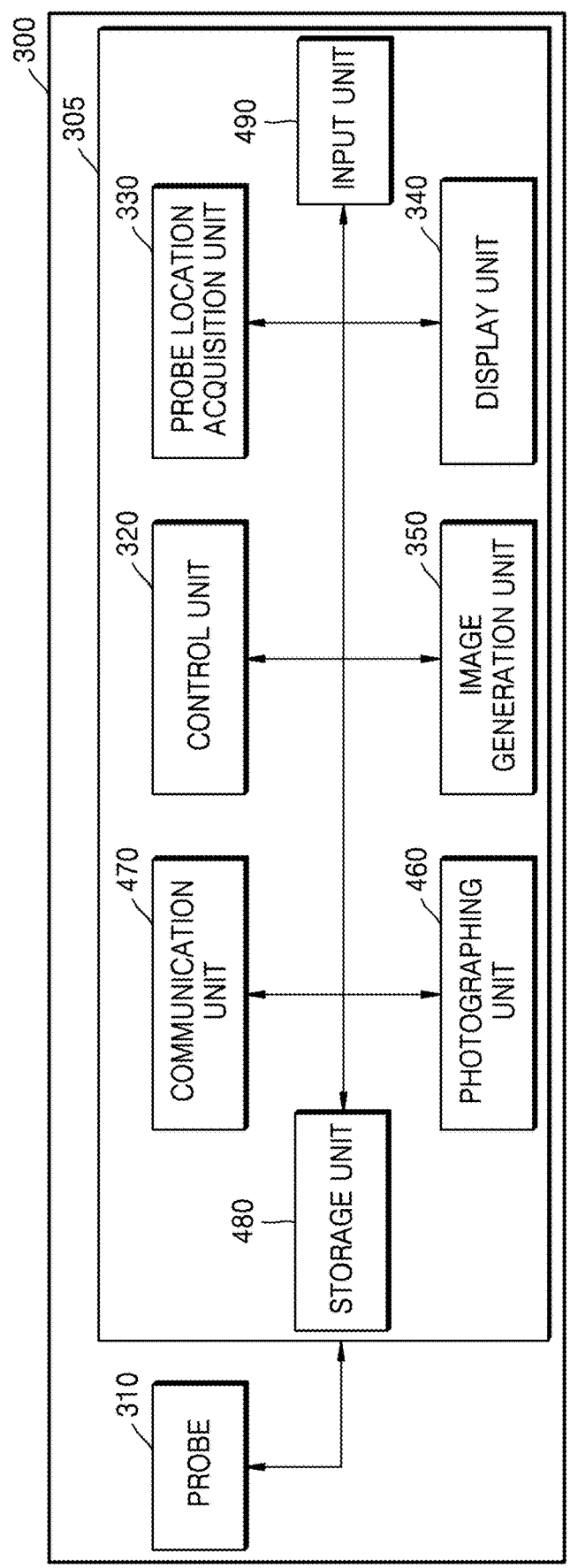
FIG. 5 is a block diagram of an ultrasound diagnosis apparatus according to an embodiment of the disclosure.

FIG. 5 is a block diagram of an ultrasound diagnosis apparatus 300 according to an embodiment of the disclosure.

Referring to FIG. 5, the ultrasound diagnosis apparatus 300 may further include a photographing unit 460, a communication unit 470, a storage unit 480, and an input unit 490, in addition to the components of the ultrasound diagnosis apparatus 300 of FIG. 4.

The photographing unit 460 may photograph the probe 310 and the object. The probe location acquisition unit 330 may detect an area corresponding to the probe 310 and an area corresponding to the object from an image obtained by photographing the probe 310 and the object, and acquire the location of the probe 310 based on a location of the area corresponding to the probe 310 with respect to the area corresponding to the object.

The photographing unit 460 is an image capturing apparatus, and a camcorder, a webcam, a digital camera, or the like may be used as the photographing unit 460. A recent camera that is used in game players and PCs and is capable of motion recognition may be used as the photographing unit 460. The ultrasound diagnosis apparatus 300 may further include the photographing unit 460 photographing the probe 310 and the object, and the probe location acquisition unit 330 may detect an area corresponding to the probe 310 and an area corresponding to the object from the image obtained by photographing the probe 310 and the object, and acquire the location of the probe 310 based on the location of the area corresponding to the probe with respect to the area corresponding to the object.

The communication unit 470 may correspond to the communication unit 30 of FIG. 1. When the location of the probe 310 corresponds to the reference location, the communication unit 470 may transmit an ultrasound image to an external device. The communication unit 470 may receive information used to determine the reference location, from the external device. The communication unit 470 may transmit at least one selected from the location of the probe 310, the reference location, the ultrasound image, and an image that is displayed on the display unit 340 to the external device. The communication unit 470 may receive, from the external device, information used to generate the ultrasound image, and the control unit 320 may control at least one selected from the probe 310 and the image generation unit 350, based on the received information.

The storage unit 480 may correspond to the memory 40 of FIG. 1. The storage unit 480 may map a plurality of locations of the probe 310 with a plurality of reference ultrasound images and store a result of the mapping. The probe location acquisition unit 330 may compare the ultrasound image with the plurality of reference ultrasound images, select one from among the plurality of reference ultrasound images based on a result of the comparison, and acquire a location corresponding to the selected reference ultrasound image as the location of the probe 310.

Figure 6A:
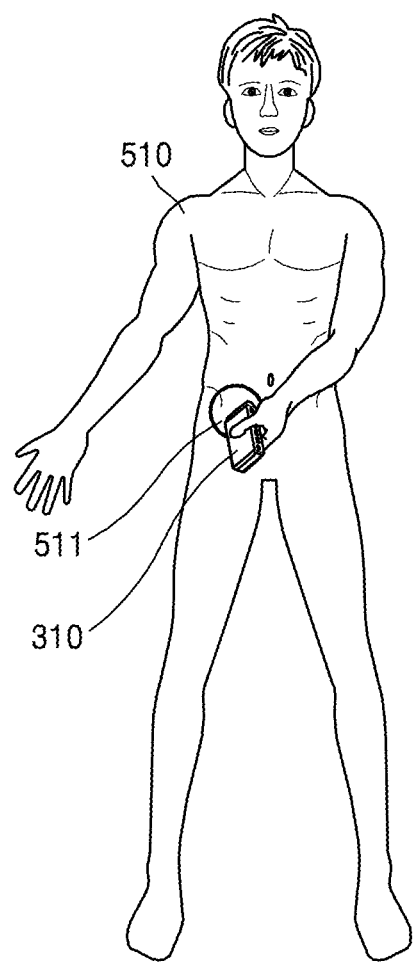
FIGS. 6A and 6B explain a method in which an ultrasound diagnosis apparatus operates, according to an embodiment of the disclosure.
Figure 6B:
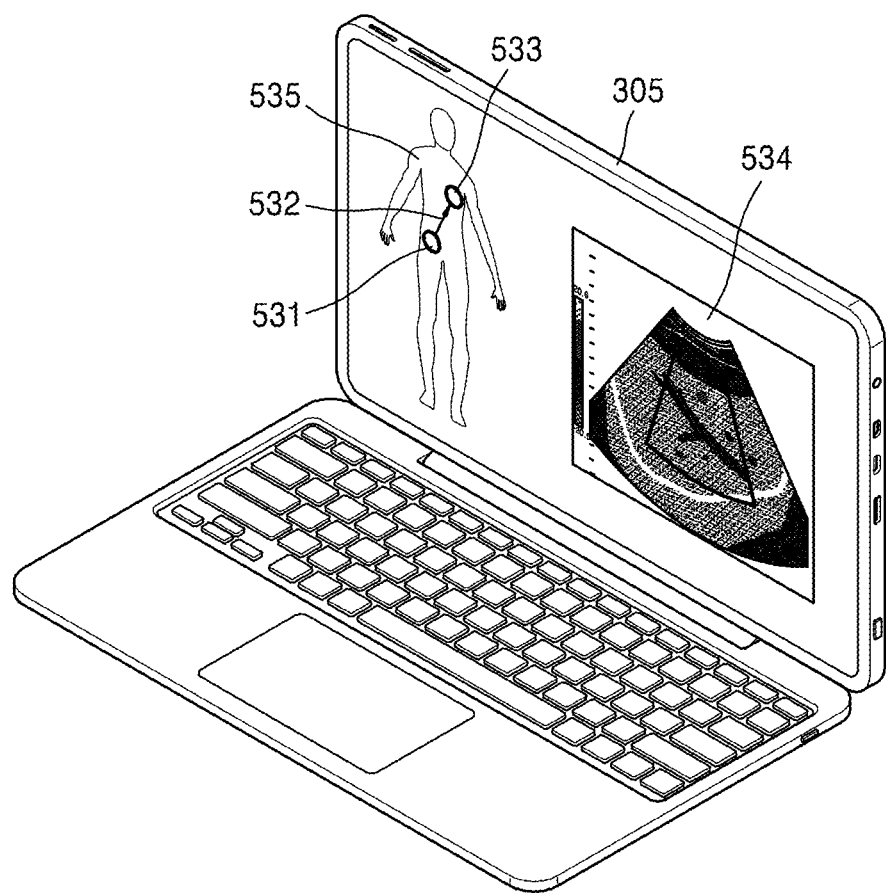

A detailed operation of the ultrasound diagnosis apparatus 300 will now be described in detail with reference to FIGS. 6A-22. FIGS. 6A and 6B explain a method in which the ultrasound diagnosis apparatus 300 operates, according to an embodiment of the disclosure.

FIG. 6A illustrates acquisition of an ultrasound image by a user 510 using the probe 310, according to an embodiment of the disclosure. Referring to FIG. 6A, the user 510 is identical to an inspection target, a body part of which an ultrasound image is to be acquired. However, embodiments of the disclosure are not limited thereto, and the user 510 may be a person who uses the ultrasound diagnosis apparatus 300 to diagnose the inspection target, such as a friend or a family of the inspection target.

For convenience of explanation, a case where the user 510 is identical with the inspection target will now be illustrated. The user 510 may position the probe 310 at an arbitrary location 511 of the body of the user 510. The probe 310 may be positioned at a location corresponding to a body part of which an ultrasound image is desired to be acquired by the user 510, but may be positioned at a wrong location due to lack of background knowledge of the user 510. For example, even when the user 510 desires to acquire an ultrasound image of a liver, the user 510 may position the probe 310 at a location inappropriate for acquiring an image of the liver, due to being unaware of the location of the liver within his or her body.

FIG. 6B illustrates a desktop 305 according to an embodiment of the disclosure.

Referring to FIG. 6B, the image generation unit 350 may generate an ultrasound image 534, based on the ultrasound data acquired by the probe 310. The ultrasound image 534 may be displayed on the display unit 340. The storage unit 480 may map the plurality of locations of the probe 310 with the plurality of reference ultrasound images and store a result of the mapping. The plurality of reference ultrasound images may include ultrasound images serving as respective standards of body parts of the body of the user 510. The probe location acquisition unit 330 may compare the ultrasound image 534 generated by the image generation unit 350 with the plurality of reference ultrasound images. The probe location acquisition unit 330 may select a reference ultrasound image corresponding to the ultrasound image 534 from among the plurality of reference ultrasound images, according to a result of the comparison. For example, the probe location acquisition unit 330 may select a reference ultrasound image that is the most similar to the ultrasound image 534. For example, the probe location acquisition unit 330 may calculate a correlation between the ultrasound image 534 and each of the reference ultrasound images, which are stored in the storage unit 480. The probe location acquisition unit 330 may select a reference ultrasound image having the highest correlation with the ultrasound image 534.

The probe location acquisition unit 330 may determine a body part corresponding to the selected reference ultrasound image as a location 531 of the probe 310. The location 531 of the probe 310 may be acquired in real time as the user 510 moves the probe 310. The location 531 of the probe 310 may be displayed together with an image 535 representing the object, on the display unit 340.

Based on the body part of which the user 510 desires to acquire an ultrasound image, the ultrasound diagnosis apparatus 300 may determine a reference location of the probe 310 which is used to acquire the ultrasound image of the body part. The ultrasound diagnosis apparatus 300 may display a reference location 533 together with the image 535 representing the object, on the display unit 340. The ultrasound diagnosis apparatus 300 may display a path 532 from the location 531 of the probe 310 to the reference location 533, on the image 535 representing the object.

Thus, the user 510 may move the probe 310 while checking in real time the location 531 of the probe 310 and the reference location 533 displayed on the display unit 340. The user 510 may move the probe 310 while checking in real time the path 532 from the location 531 of the probe 310 to the reference location 533. The user 510 may move the probe 310 at the reference location 533, which is suitable for acquiring the ultrasound image, by moving the probe 310 along the path 532 provided by the ultrasound diagnosis apparatus 300.

For example, when the user 510 desires to acquire an ultrasound image of a liver, the ultrasound diagnosis apparatus 300 may determine, as the reference location, a location of the probe 310 that is suitable for acquiring the ultrasound image of the liver. The ultrasound diagnosis apparatus 300 may display the determined reference location on the image 535 representing the object. Thus, the user 510 of the ultrasound diagnosis apparatus 300 may easily move the probe 310 to the reference location, even when the user 510 has no background knowledge about the reference location of the probe 310 that is suitable for acquiring the ultrasound image of the liver.

Figure 7:
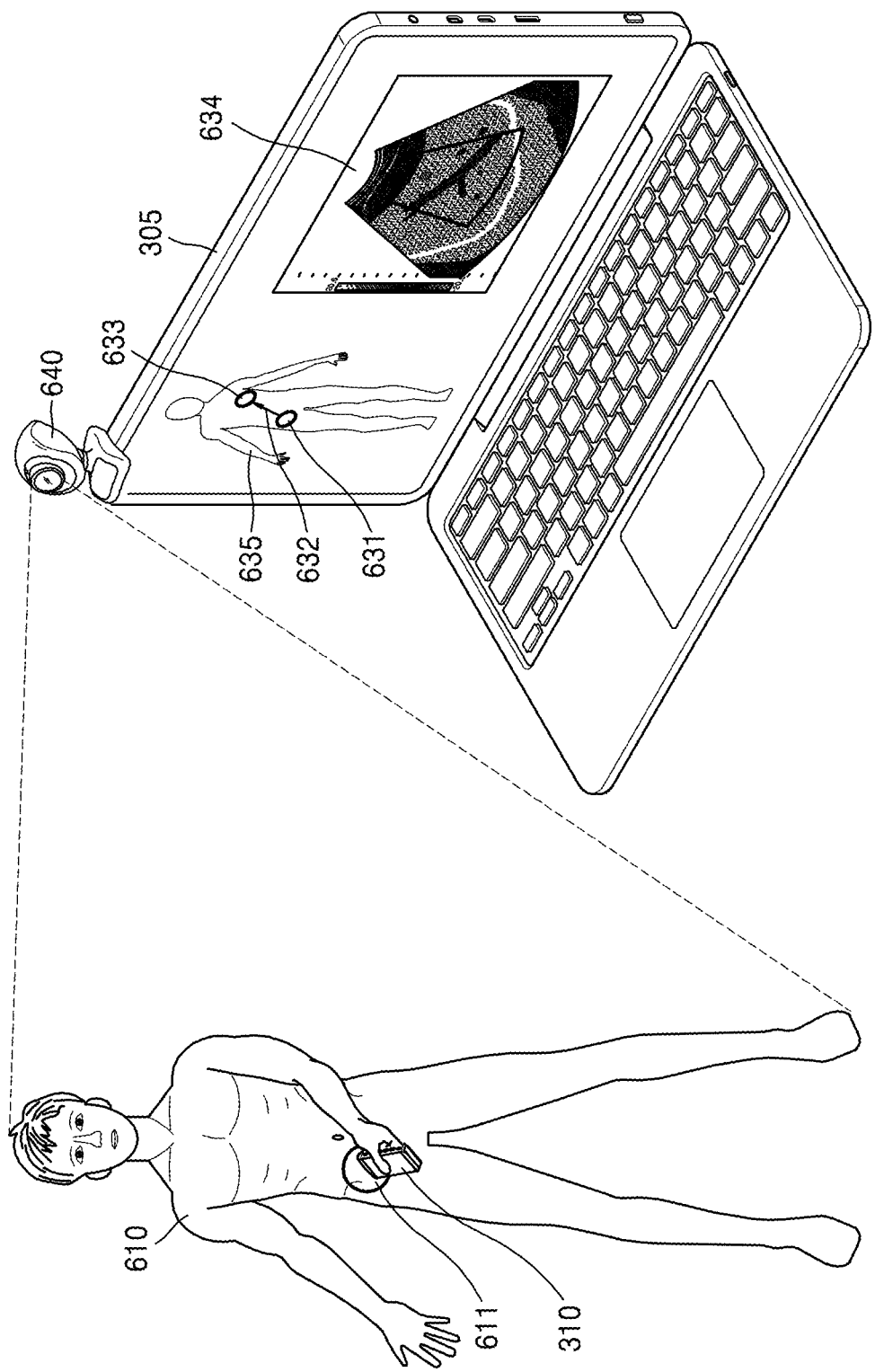
FIG. 7 explains a method in which an ultrasound diagnosis apparatus operates, according to an embodiment of the disclosure.

FIG. 7 explains a method in which the ultrasound diagnosis apparatus 300 operates, according to an embodiment of the disclosure.

The desktop 305 may further include a photographing unit 640 photographing the probe 310 and the object, and the probe location acquisition unit 330 may detect an area corresponding to the probe 310 and an area corresponding to the object from an image obtained by photographing the probe 310 and the object, and acquire the location of the probe 310 based on a location of the area corresponding to the probe 310 with respect to the area corresponding to the object.

For example, referring to FIG. 7, a user 610 may position the probe 310 at an arbitrary part 611 of the body of the user 610, similar to FIG. 6A. The photographing unit 640 may photograph the user 610 and the probe 310. Although the photographing unit 640 photographs the entire body in FIG. 7, embodiments of the disclosure are not limited thereto. The photographing unit 640 may photograph a portion of the body of the inspection target. The probe location acquisition unit 330 may acquire a location 631 of the probe 310, based on an image captured by photographing the user 610 and the probe 310.

The probe location acquisition unit 330 may acquire an area corresponding to the probe 310 from the captured image. The probe location acquisition unit 330 may acquire the location 631 of the probe 310 on an image 635 representing the object, based on a location of the area corresponding to the probe 310 on an image 635 representing the object. The location 631 of the probe 310 may be acquired in real time as the user 610 moves the probe 310. A sensor may be attached to the probe 310 and acquire the location 631 of the probe 310. The location 631 of the probe 310 may be displayed together with the image 635 representing the object, on the display unit 340.

The display unit 340 may display an ultrasound image 634 generated by the image generation unit 350. A predetermined reference location 633 may be displayed together with the image 635 representing the object, on the display unit 340. A path 632 from the location 631 of the probe 310 to the reference location 633 may be displayed together with the image 635 representing the object, on the display unit 340.

Figure 8A:
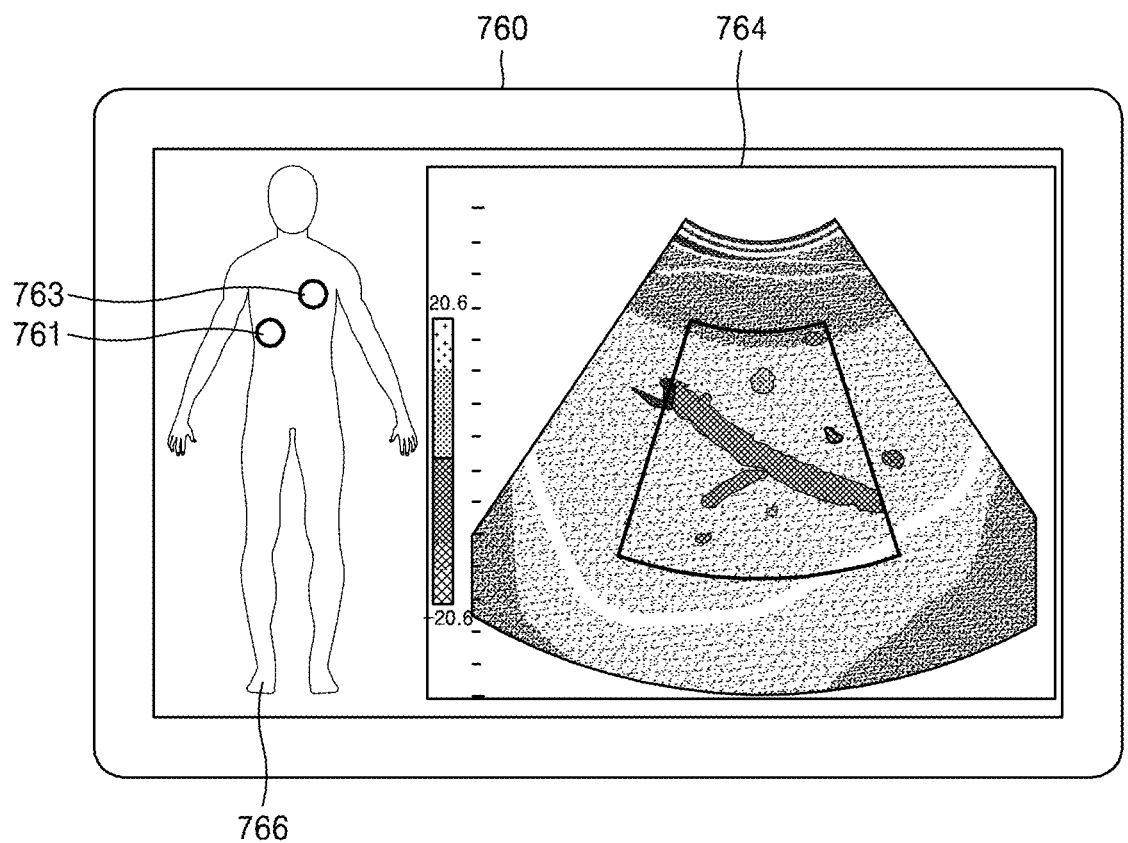
FIGS. 8A and 8B illustrate screen images of an ultrasound diagnosis apparatus according to an embodiment of the disclosure.
Figure 8B:
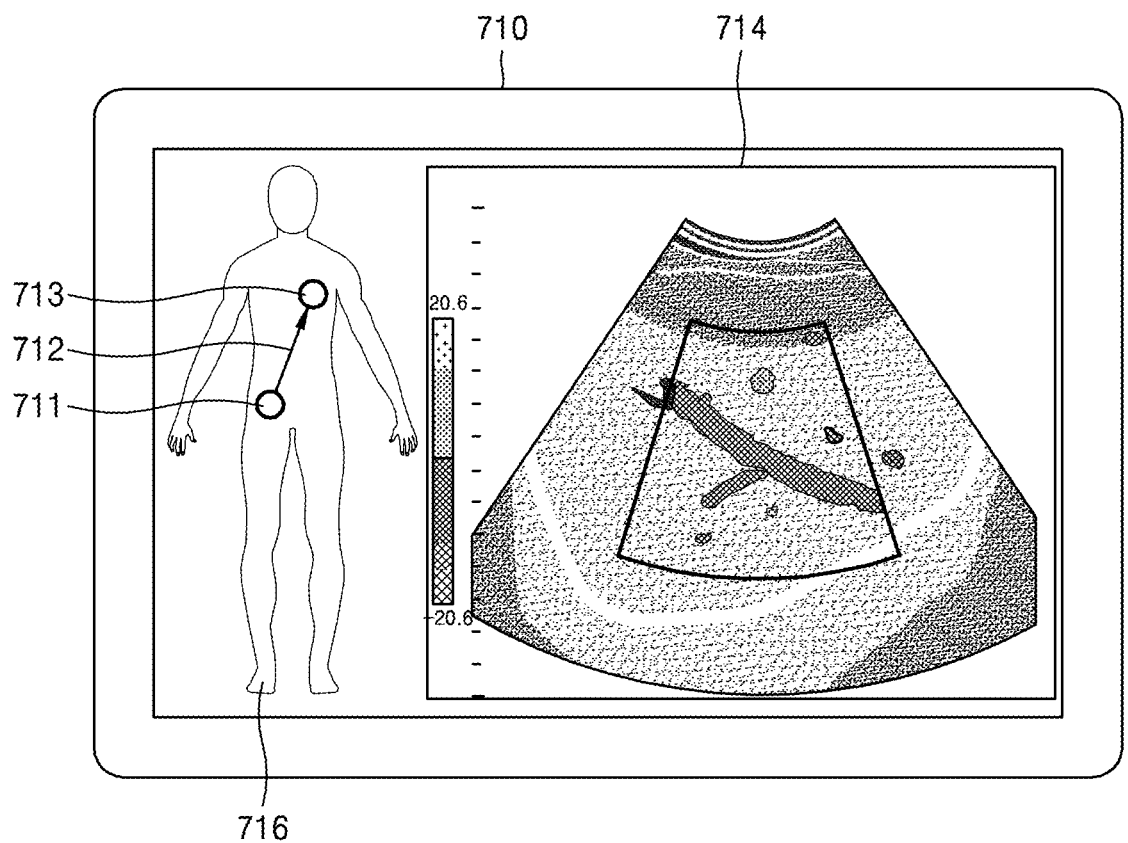

FIGS. 8A and 8B illustrate screen images of an ultrasound diagnosis apparatus according to an embodiment of the disclosure.

Referring to FIG. 8A, a display unit 760 may display an ultrasound image 764 generated by the image generation unit 350, and an image 766 representing the object. When a location 761 of the probe 310 and a predetermined reference location 763 are acquired, the display unit 760 may display the location 761 of the probe 310 and the predetermined reference location 763. The location 761 of the probe 310 may be updated in real time and displayed on the display unit 760, and a user may move the probe 310 while checking the updated location 761 of the probe 310. Thus, the user may easily move the location 761 of the probe to the predetermined reference location 763.

FIG. 8B illustrates a screen image according to another embodiment of the disclosure. When it is determined that the location of the probe 310 does not correspond to a reference location, the control unit 320 may determine a movement path to be taken by the probe 310 to move to the reference location. The display unit 340 may display a movement path from the location of the probe 310 to the reference location on an image representing the object.

A display unit 710 may display an ultrasound image 714 generated by the image generation unit 350, and an image 716 representing the object. The ultrasound diagnosis apparatus 300 may acquire a location 711 of the probe 310 and a predetermined reference location 713. The display unit 710 may display the location 711 of the probe 310 and the predetermined reference location 713.

According to an embodiment of the disclosure, when it is determined that the location 711 of the probe 310 does not correspond to the reference location 713, the control unit 320 may determine a path 712 to be taken to move the location 711 of the probe 310 to the reference location 713. For example, the path 712 may be a shortest distance from the location 711 of the probe 310 to the reference location 713. The path 712 may be a path for acquiring an optimal ultrasound image of the object.

The location 711 of the probe 310 may be changed in real time as the user moves the probe 310. The control unit 320 may determine the path 712 in real time, based on the changed location 711 of the probe 310. The path 712 may be displayed together with the image 716 representing the object, on the display unit 710. The user may easily move the location 711 of the probe 310 to the reference location 713 while checking the location 711 of the probe 310, the path 712, and the reference location 713, which are displayed on the display unit 710.

According to an embodiment of the disclosure, the communication unit 470 may receive information related to the reference location 713 and the path 712 from a remote user, and the control unit 320 may acquire the reference location 713 and the path 712 based on the received information.

Figure 9A:
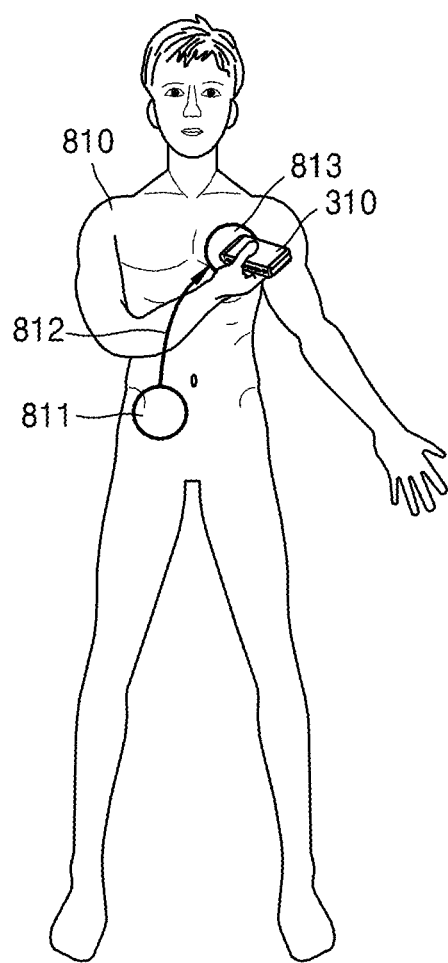
FIGS. 9A-9C explain a method in which an ultrasound diagnosis apparatus operates, according to an embodiment of the disclosure.
Figure 9B:
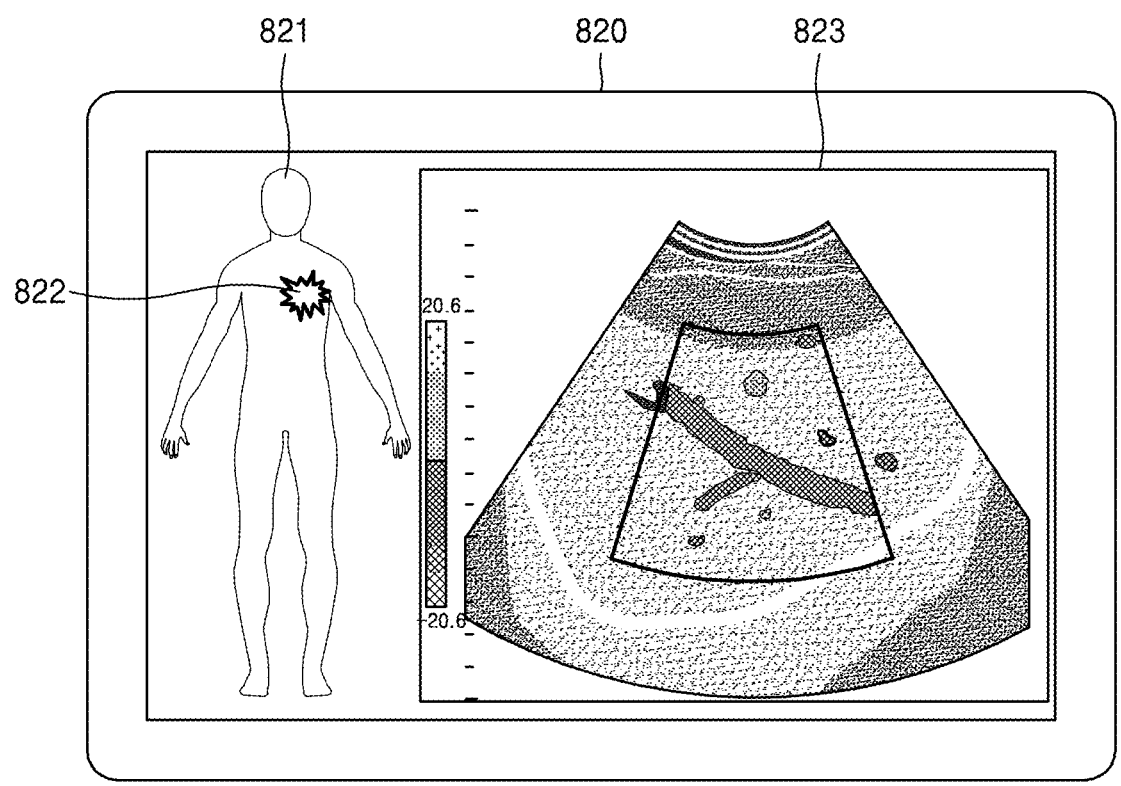
Figure 9C:
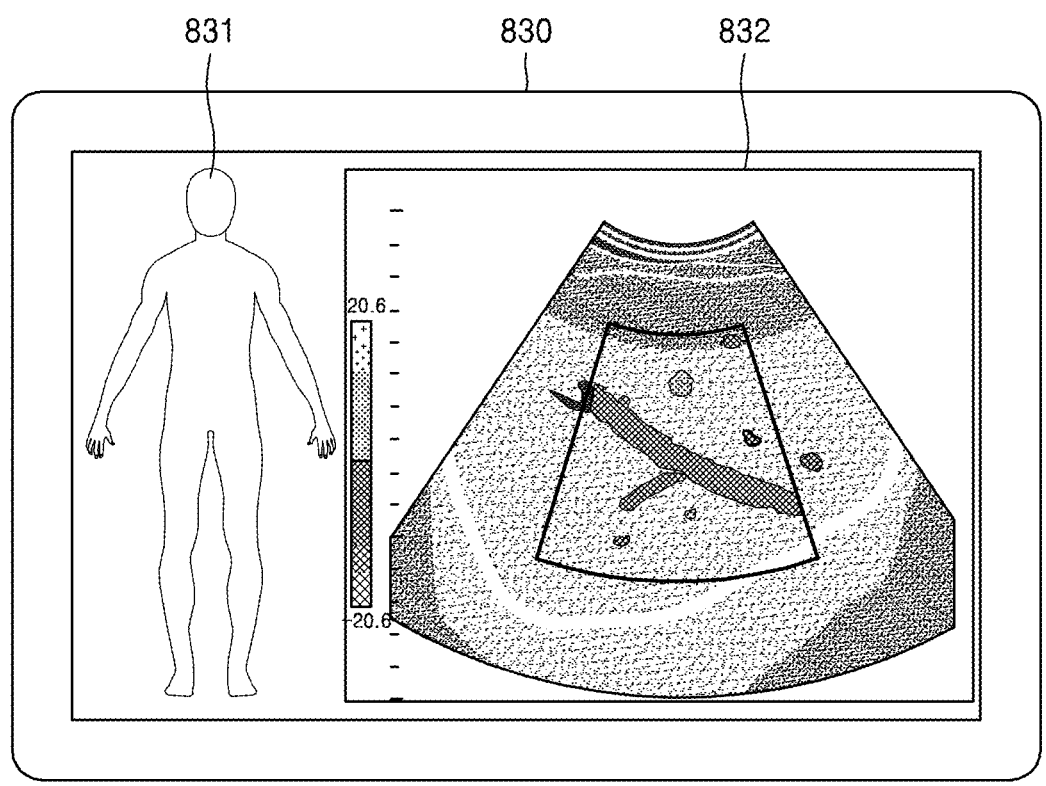

FIGS. 9A-9C explain a method in which the ultrasound diagnosis apparatus 300 operates, according to an embodiment of the disclosure.

When a location of the probe 310 corresponds to a reference location, the control unit 320 may control the display unit 340 to display an image representing that the location of the probe 310 corresponds to the reference location. When the location of the probe 310 corresponds to the reference location, the control unit 320 may also control the probe 310 to transmit an ultrasound signal to the object and receive an echo signal from the object to acquire ultrasound data.

For example, FIG. 9A illustrates a case where a user 810 is identical with an inspection target, but embodiments of the disclosure are not limited thereto. The user 810 may be a person who uses the ultrasound diagnosis apparatus 300 to diagnose the inspection target. The user 810 may position the probe 310 at a reference location 813 by moving the probe 310 along a path 812 from an initial location 811. The control unit 320 may determine whether the reference location 813 corresponds to a location of the probe 310. When the location of the probe 310 corresponds to the reference location 813, the control unit 320 may control the display unit 340 to display an image representing that the location of the probe 310 corresponds to the reference location 813. Although not shown in the drawings, when the location of the probe 310 corresponds to the reference location 813, the control unit 320 may inform the user 810 that the location of the probe 310 corresponds to the reference location 813, via sound, light, vibration, or the like instead of via the image.

For example, FIG. 9B illustrates an image representing that the location of the probe 310 corresponds to a reference location, according to an embodiment of the disclosure. A display unit 820 may display an image 821 representing a target, together with an ultrasound image 823. When the location of the probe 310 corresponds to the reference location, the control unit 320 may control an icon 822 representing the reference location to flicker. Alternatively, when the location of the probe 310 corresponds to the reference location, the control unit 320 may control the entire screen image to flicker. However, embodiments of the disclosure are not limited thereto, and the ultrasound diagnosis apparatus 300 may inform a user that the probe 310 has reached a reference location suitable for acquiring an ultrasound image, by notifying the user that the reference location corresponds to the location of the probe 310, via sound, vibration, or the like.

For example, FIG. 9C illustrates an image that may be displayed when the location of the probe 310 corresponds to a reference location, according to an embodiment of the disclosure. A display unit 830 may display an image 831 representing a target, together with an ultrasound image 832. When the location of the probe 310 corresponds to the reference location, the control unit 320 may control the location of the probe 310, a path, and the reference location to disappear. A user may easily determine whether the probe 310 has reached the reference location, by checking whether the location of the probe 310, the path, and the reference location have disappeared from the display unit 830.

When the location of the probe 310 corresponds to the reference location, the ultrasound diagnosis apparatus 300 may control the probe 310 to transmit an ultrasound signal to the object and receive an echo signal from the object to acquire ultrasound data. The image generation unit 350 may generate an ultrasound image, based on the acquired ultrasound data. The acquired ultrasound image 823 or 832 may be displayed on the display unit 820 or 830.

The ultrasound diagnosis apparatus 300 may determine whether the acquired ultrasound image 823 or 832 is abnormal, by comparing the acquired ultrasound image 823 or 832 with a predetermined ultrasound image. The ultrasound diagnosis apparatus 300 may suggest the inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image 823 or 832. The ultrasound diagnosis apparatus 300 may enable a medical diagnosis to be made with respect to the ultrasound image 823 or 832, by transmitting the ultrasound image 823 or 832 to the professional medical organization in response to a user input.

Figure 10A:
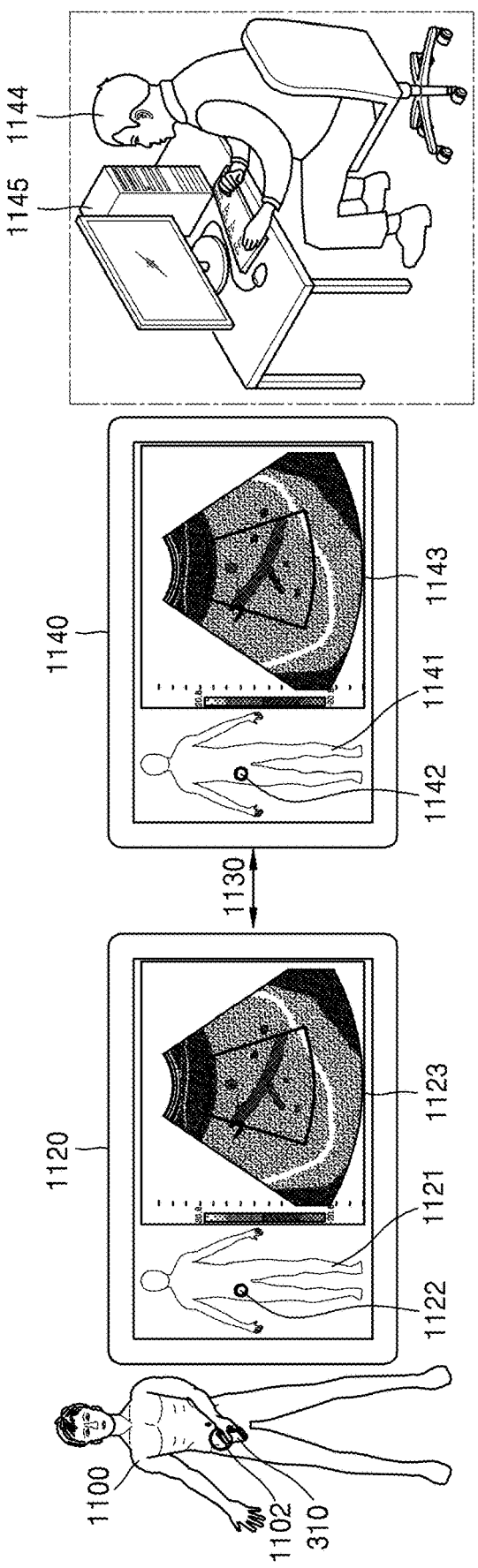
FIGS. 10A and 10B explain a method in which an ultrasound diagnosis apparatus interoperates with an external device, according to an embodiment of the disclosure.
Figure 10B:
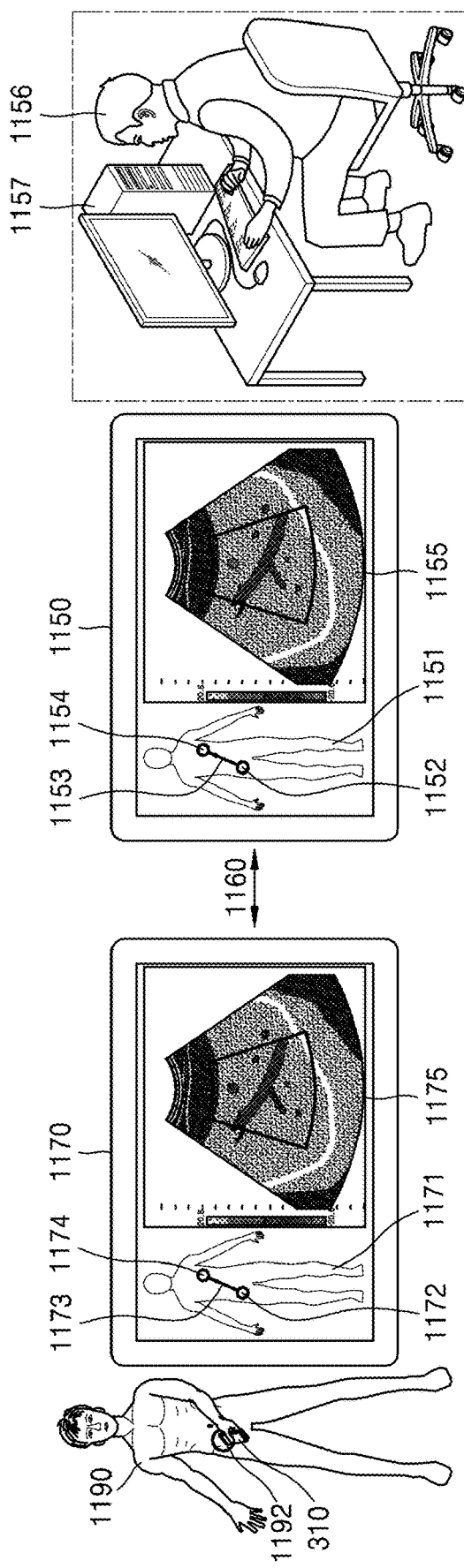

FIGS. 10A and 10B explain a method in which the ultrasound diagnosis apparatus 300 interoperates with an external device, according to an embodiment of the disclosure.

FIGS. 10A and 10B illustrate cases where users 1100 and 1190 are identical with inspection targets, but embodiments of the disclosure are not limited thereto. The user 1100 may be a person who uses the ultrasound diagnosis apparatus 300 to diagnose the inspection target.

When the user 1100 wants to receive a diagnosis from a remote medical expert 1144, the user 1100 may request the remote medical expert 1144 for the diagnosis. The remote medical expert 1144 may request the ultrasound diagnosis apparatus 300 to acquire an ultrasound image, via an external device 1145. The ultrasound diagnosis apparatus 300 may enable a remote medical examination to be performed by the remote medical expert 1144, by interoperating with the external device 1145 as described below.

As shown in FIG. 10A, in response to a request from the remote medical expert 1144 to acquire an ultrasound image, the user 1100 may position the probe 310 at an arbitrary body part 1102. The ultrasound diagnosis apparatus 300 may acquire a current location of the probe 310 and display the current location of the probe 310 on a display unit 1120. For example, as shown in FIG. 10A, the ultrasound diagnosis apparatus 300 may display a location 1122 of the probe 310 on an image 1121 representing a target. The communication unit 470 may transmit/receive information to/from the external device 1145, as indicated by reference numeral 1130. For example, the communication unit 470 may transmit the location 1122 of the probe 310 and an ultrasound image 1123 to the external device 1145.

A display unit 1140 of the external device 1145 may display the same screen image as that displayed on the display unit 1120 of the user 1100. For example, the display unit 1140 of the external device 1145 may display an ultrasound image 1143. An image 1141 representing the object, together with a location 1142 of the probe 310, may be displayed on the display unit 1140. The location 1142 of the probe 310 and the ultrasound image 1143, which are provided via the ultrasound diagnosis apparatus 300, may respectively correspond to the location 1122 of the probe 310 and the ultrasound image 1123, which are provided via the external device 1145. For example, the whole or a portion of a screen image that is provided to the user 1100 via the ultrasound diagnosis apparatus 300 may be provided to the remote medical expert 1144 via the external device 1145. In other words, the medical expert 1144 may receive the same screen image as that received by the user 1100.

Since the user 1100 positions the probe 310 at any location without special knowledge about a body part desired to be observed by the medical expert 1144, the location 1142 of the probe 310 positioned by the user 1100 may not be a location (that is, a reference location) suitable for acquiring an ultrasound image of the body part desired to be observed by the medical expert 1144. The medical expert 1144 may transmit information related to the reference location to the ultrasound diagnosis apparatus 300 via the external device 1145. The ultrasound diagnosis apparatus 300 may receive the information related to the reference location and display the reference location to the user 1100. The user 1100 may change the location of the probe 310, based on the displayed reference location.

Referring to FIG. 10B, a remote medical expert 1156 may determine information used to determine a reference location 1154, by checking an ultrasound image 1155 and a location 1152 of the probe 310 displayed on a display unit 1150. The information used to determine the reference location 1154 may be an accurate coordinate on the body, but may be a body part of which the medical expert 1156 desires to acquire an ultrasound image. An external device 1157 may receive the information used to determine the reference location 1154, from the medical expert 1156. The external device 1157 may also receive a path 1153 from the location 1152 of the probe 310 to the reference location 1154, from the medical expert 1156. For example, the medical expert 1156 may input the reference location 1154 and the path 1153 to an image 1151 representing a target, by using a mouse. The ultrasound diagnosis apparatus 300 may receive the information 1160 used to determine the reference location 1154 and the path 1153 from the external device 1157 via the communication unit 470. The ultrasound diagnosis apparatus 300 may acquire the reference location 1154, which is suitable for acquiring an ultrasound image 1175, based on the received information used to determine the reference location 1154.

A display unit 1170 of the ultrasound diagnosis apparatus 300 may display a location 1172 of the probe 310, a path 1173, and a reference location 1174 on an image 1171 representing the object. A user 1190 may move the probe 310 from a location 1192 of the probe 310 to a reference location, based on the displayed path 1173 and the displayed reference location 1174.

When the probe 310 is positioned at a location suitable for scanning a body part of which an ultrasound image is desired to be acquired, the ultrasound diagnosis apparatus 300 may inform the user 1190 that the probe 310 is positioned at the suitable location, according to a predetermined method. The ultrasound diagnosis apparatus 300 may generate an ultrasound image of the body part of which an ultrasound image is desired to be acquired, and display the generated ultrasound image on the display unit 1170. The communication unit 470 may transmit the generated ultrasound image to the external device 1157. The generated ultrasound image may be displayed on the display 1150 of the external device 1157. The medical expert 1156 may give a diagnosis, based on the ultrasound image displayed on the display unit 1150.

When the user 1190 is a user unskilled at manipulating the ultrasound diagnosis apparatus 300, the user 1190 may be unaccustomed to manipulating a function of the ultrasound diagnosis apparatus 300. In particular, the unskilled user 1190 has difficulty in transmitting an ultrasound signal from the probe 310 and adjusting, in a concrete way, a parameter that is used during processing a received echo signal (for example, a gain and a penetrating depth of the probe 310 and a frequency of the transmitted ultrasound signal).

Thus, the ultrasound diagnosis apparatus 300 may receive information that is used to generate an ultrasound image, from the external device 1157 via the communication unit 470. In this case, the external device 1157 may receive the information used to generate an ultrasound image, from the medical expert 1156. The ultrasound diagnosis apparatus 300 may control at least one selected from the probe 310 and the image generation unit 350, based on the received information.

For example the ultrasound diagnosis apparatus 300 may control a parameter including at least one selected from the gain, the penetrating depth, and the frequency of the probe 310, based on the received information. The controller 320 may also control a beamforming method such as timing adjustment of a beam, based on the received information. The ultrasound diagnosis apparatus 300 may also control image processing including at least one selected from noise removal, pixel interpolation, image continuation, and space composition to be performed, based on the received information.

According to an embodiment of the disclosure, since the remote medical expert 1156 is able to manipulate the ultrasound diagnosis apparatus 300, the number of manipulations of the ultrasound diagnosis apparatus 300 by an unskilled user may be minimized. The medical expert 1156 may easily give a diagnosis, based on the ultrasound image controlled by the medical expert 1156.

Figure 11:
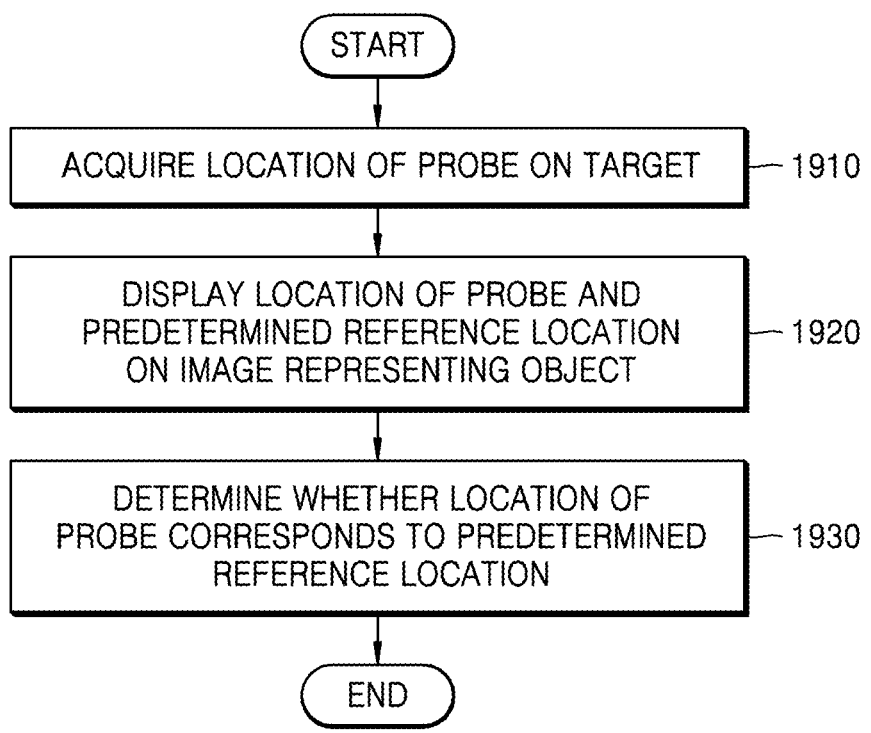
FIG. 11 is a flowchart of a method of operating an ultrasound diagnosis apparatus, according to an embodiment of the disclosure.

FIG. 11 is a flowchart of a method of operating an ultrasound diagnosis apparatus 300, according to an embodiment of the disclosure.

Referring to FIG. 11, in operation 1910, the ultrasound diagnosis apparatus 300 may acquire a location of a probe on a target. For example, the ultrasound diagnosis apparatus 300 may acquire the location of the probe on the object according to methods as described above with reference to FIGS. 5-7. For example the ultrasound diagnosis apparatus 300 may acquire the location of the probe by comparing an ultrasound image acquired at the location of the probe with a reference ultrasound image. The ultrasound diagnosis apparatus 300 may also acquire the location of the probe, based on an image captured by photographing the probe and the object. The ultrasound diagnosis apparatus 300 may also acquire the location of the probe by using a location tracking sensor. Detailed descriptions of the methods of acquiring the location of the probe have already been given above, and thus will be omitted here.

In operation 1920, the ultrasound diagnosis apparatus 300 may display the location of the probe and a predetermined reference location on an image representing the object. In operation 1930, the ultrasound diagnosis apparatus 300 may determine whether the location of the probe corresponds to the predetermined reference location. The reference location is a location that is adequate for the ultrasound diagnosis apparatus 300 to obtain an ultrasound image.

The ultrasound diagnosis apparatus operating method of FIG. 11 may be performed by the ultrasound diagnosis apparatus 300 of FIG. 5. Thus, a description of the method of FIG. 11 that has already been given above with reference to FIG. 5 will be omitted. The operation 1910 of acquiring the location of the probe may be performed by the probe location acquisition unit 330. The displaying operation 1920 may be performed by the display unit 340. The operation 1930 of determining whether the location of the probe corresponds to the predetermined reference location may be performed by the control unit 320.

When it is determined that the location of the probe corresponds to the reference location, the ultrasound diagnosis apparatus 300 may display an image representing that the location of the probe corresponds to the reference location. When it is determined that the location of the probe corresponds to the reference location, the ultrasound diagnosis apparatus 300 may transmit an ultrasound signal to the object and receive an echo signal from the object to thereby acquire ultrasound data. In other words, when the probe is positioned at a location that is the most adequate to acquire an ultrasound image, the ultrasound diagnosis apparatus 300 may automatically acquire the ultrasound data. Accordingly, the ultrasound diagnosis apparatus 300 may enable a user unskilled at manipulating the ultrasound diagnosis apparatus 300 to more conveniently acquire an accurate ultrasound image.

The ultrasound diagnosis apparatus 300 may determine whether an acquired ultrasound image is abnormal, by comparing the acquired ultrasound image with a predetermined ultrasound image. The ultrasound diagnosis apparatus 300 may suggest the inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image. The ultrasound diagnosis apparatus 300 may enable a medical diagnosis to be made with respect to the ultrasound image, by transmitting the ultrasound image to a professional medical organization in response to a user input.

Figure 12:
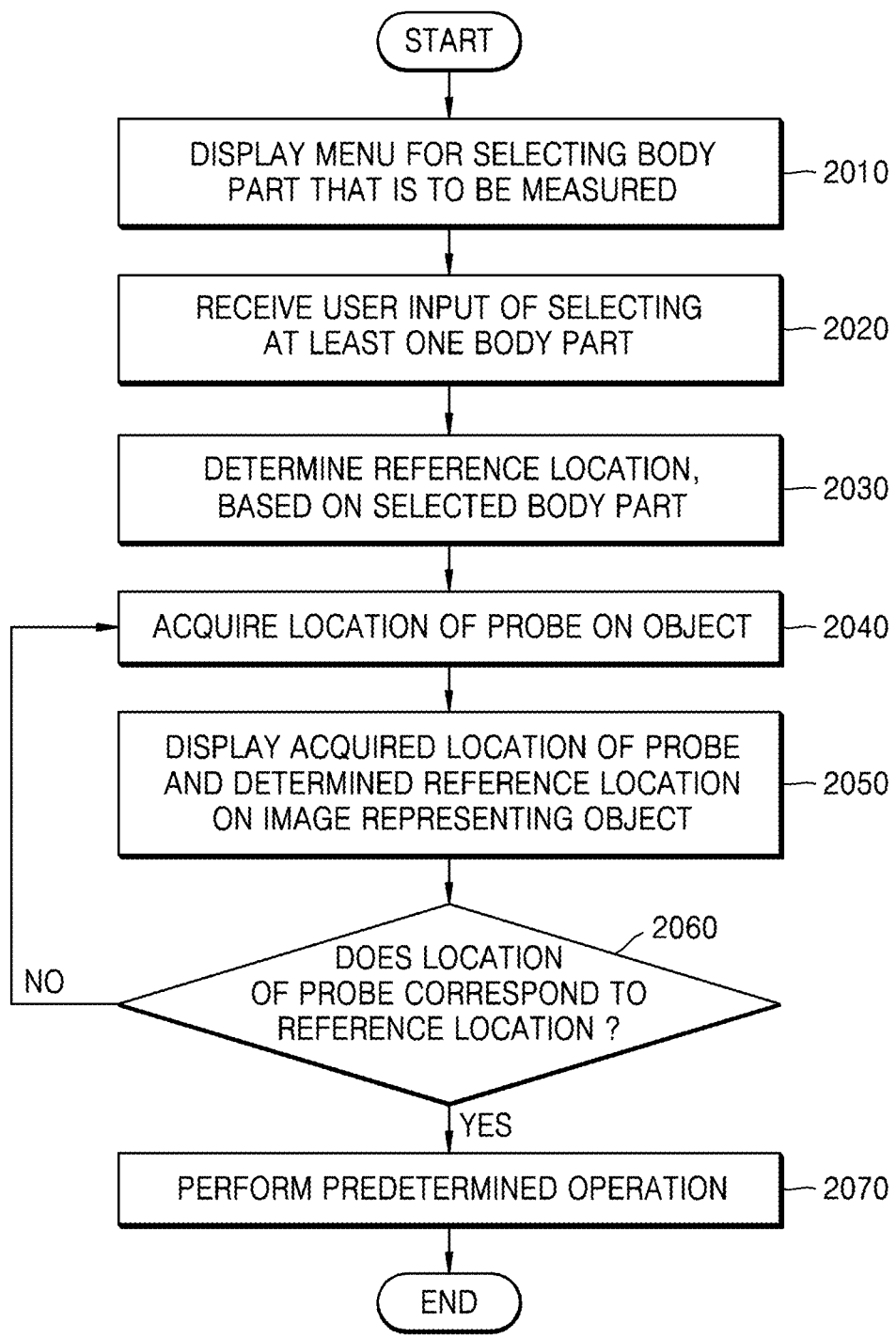
FIG. 12 is a flowchart of a method of operating an ultrasound diagnosis apparatus in order to determine a reference location, according to an embodiment of the disclosure.

FIG. 12 is a flowchart of a method of operating an ultrasound diagnosis apparatus 300 in order to determine a reference location, according to an embodiment of the disclosure.

The reference location is a location of a probe that is suitable to acquire an ultrasound image of each body part. When a user selects a body part of which an ultrasound image is to be acquired, the ultrasound diagnosis apparatus 300 may acquire a reference location that is suitable to acquire the ultrasound image, based on the selected body part.

Referring to FIG. 12, in operation 2010, the ultrasound diagnosis apparatus 300 may display a menu for selecting a body part that is to be measured. The body part selection menu that is provided by the ultrasound diagnosis apparatus 300 will be described in detail later with reference to FIGS. 15-22.

In operation 2020, the ultrasound diagnosis apparatus 300 may receive a user input of selecting at least one body part from a plurality of body parts included in the body part selection menu. In operation 2030, the ultrasound diagnosis apparatus 300 may determine a reference location, based on the selected body part. For example, the storage unit 480 may store a reference location that is suitable to acquire an ultrasound image corresponding to each body part. The ultrasound diagnosis apparatus 300 may select a reference location corresponding to the selected body part from among the stored reference locations.

In operation 2040, the ultrasound diagnosis apparatus 300 may acquire a location of a probe on an object. The method described above with reference to FIGS. 6A-7 may be equally applied to a method in which the probe location acquisition unit 330 acquires the location of the probe.

For example, to acquire the location of the probe, the ultrasound diagnosis apparatus 300 may acquire an ultrasound image and compare the acquired ultrasound image with a plurality of pre-stored reference ultrasound images. The ultrasound diagnosis apparatus 300 may select one from among the plurality of reference ultrasound images based on a result of the comparison, and acquire a location corresponding to the selected reference ultrasound image as the location of the probe.

As another example, to acquire the location of the probe, the ultrasound diagnosis apparatus 300 may photograph the probe and the object and acquire the location of the probe from an image captured by photographing the probe and the object.

In operation 2050, the ultrasound diagnosis apparatus 300 may display the acquired location of the probe and the determined reference location on an image representing the object, via the display unit 340. The display unit 340 may also display a path between the probe location and the reference location, on the image representing the object.

In operation 2060, the ultrasound diagnosis apparatus 300 may determine whether the location of the probe corresponds to the reference location. When the probe location does not correspond to the reference location, the ultrasound diagnosis apparatus 300 may return to operation 2040 to acquire the location of the probe again.

When it is determined that the location of the probe does not correspond to the reference location, the ultrasound diagnosis apparatus 300 may determine a movement path to be taken by the probe 310 to move to the reference location. The ultrasound diagnosis apparatus 300 may display the movement path from the location of the probe to the reference location on the image representing the object. A user may move the probe to the reference location, based on the path from the location of the probe to the reference location which is provided by the ultrasound diagnosis apparatus 300.

When the probe location corresponds to the reference location, the ultrasound diagnosis apparatus 300 may perform a predetermined operation, in operation 2070. For example, when it is determined that the location of the probe corresponds to the reference location, the ultrasound diagnosis apparatus 300 may display an image representing that the location of the probe corresponds to the reference location.

When it is determined that the location of the probe corresponds to the reference location, the ultrasound diagnosis apparatus 300 may transmit an ultrasound signal to the object and receive an echo signal from the object to thereby acquire ultrasound data.

The ultrasound diagnosis apparatus 300 may determine whether an acquired ultrasound image is abnormal, by comparing the acquired ultrasound image with a predetermined ultrasound image. The ultrasound diagnosis apparatus 300 may suggest an inspection target to visit a professional medical organization to receive a diagnosis, according to a result of the determination. The ultrasound diagnosis apparatus 300 may also suggest the inspection target to acquire an ultrasound image of another body part that may be necessary for diagnosis in association with the acquired ultrasound image.

When it is determined that the location of the probe corresponds to the reference location, the ultrasound diagnosis apparatus 300 may transmit an ultrasound image of the object to an external device. For example, the ultrasound diagnosis apparatus 300 may provide an ultrasound image having high diagnosis accuracy to a remote medical expert, by transmitting an ultrasound image acquired via the probe 310 located at the reference location to an external device. The remote medical expert may perform a diagnosis, based on the received ultrasound image.

Figure 13:
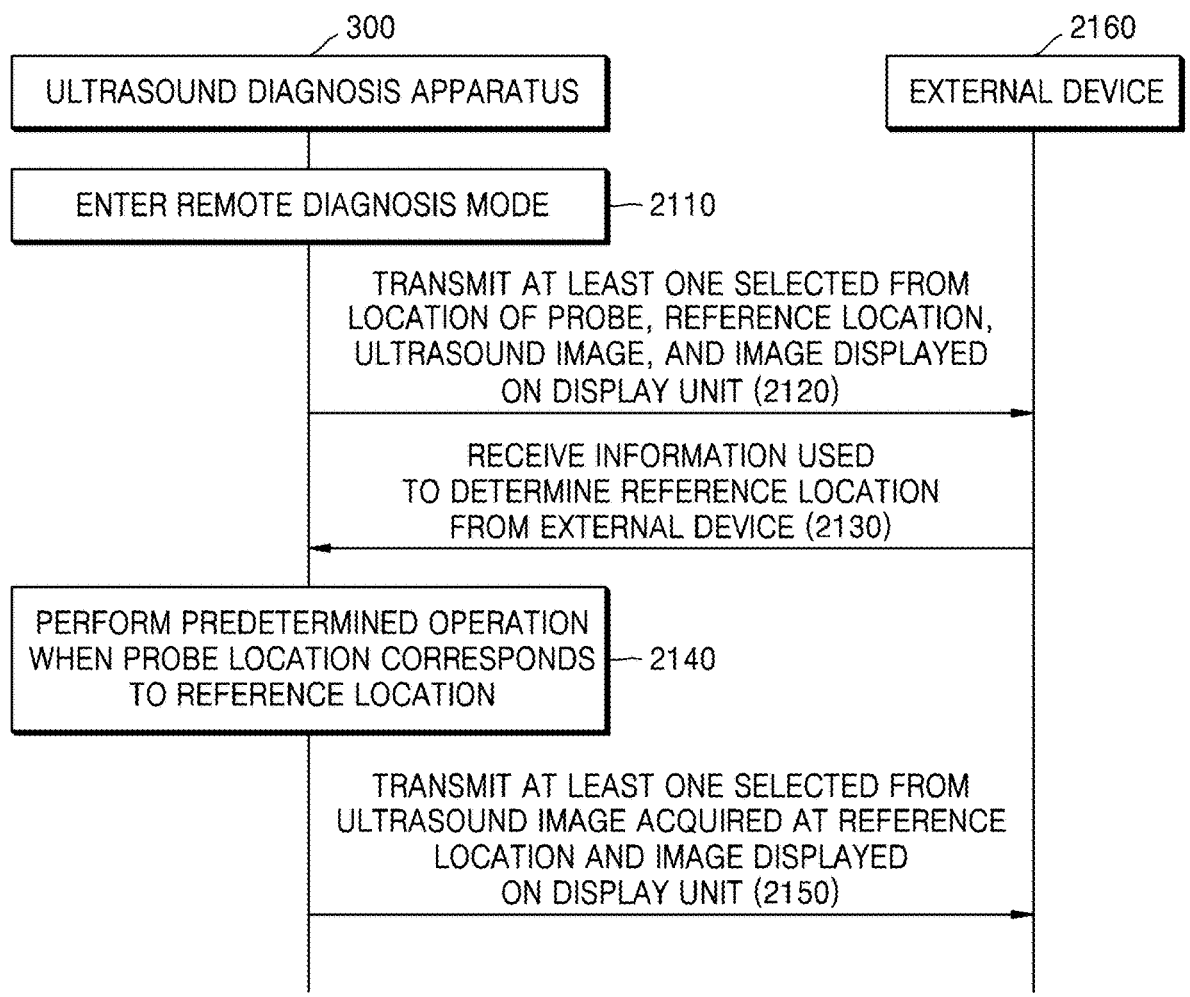
FIG. 13 is a process flow diagram of a method in which an ultrasound diagnosis apparatus interoperates with an external device, according to an embodiment of the disclosure.

FIG. 13 is a process flow diagram of a method in which the ultrasound diagnosis apparatus 300 interoperates with an external device 2160, according to an embodiment of the disclosure.

The ultrasound diagnosis apparatus 300 may enter a remote diagnosis mode, in operation 2110. In the remote diagnosis mode, a remote medical expert may diagnose an inspection target, based on an ultrasound image acquired in the house of the inspection target. In the remote diagnosis mode, since wire-wireless bidirectional communication is used, the remote medical expert and the inspection target may interoperate with each other. Since the remote medical expert is able to set various parameters of an ultrasound diagnosis apparatus, efficiency of medical treatment may improve.

When entering the remote diagnosis mode, the external device 2160 which is used by the remote medical expert and the ultrasound diagnosis apparatus 300 are connected to each other via wire-wireless bidirectional communication. For example, the ultrasound diagnosis apparatus 300 may enter a remote diagnosis mode, based on an input of a user who wants to be remotely diagnosed. As another example, the ultrasound diagnosis apparatus 300 may receive a request signal for entering a remote diagnosis mode from the external device 2160, and enter the remote diagnosis mode by transmitting a response signal to the request of the external device 2160.

The ultrasound diagnosis apparatus 300 may transmit at least one selected from a location of a probe, a reference location, an ultrasound image, and an image displayed on the display unit of the ultrasound diagnosis apparatus 300 to the external device 2160, in operation 2120. The external device 2160 may display the at least one selected from the location of the probe, the reference location, the ultrasound image, and the image displayed on the display unit, to the medical expert who uses the external device 2160. The medical expert may newly determine a body part of which an ultrasound image is desired to be acquired, based on information that is provided via the external device 2160. The medical expert may correct the reference location received by the external device 2160. The medical expert may input information used to determine the reference location, to the external device 2160. The information used to determine the reference location may be an accurate coordinate value on an image representing an object. Alternatively, the information used to determine the reference location may be the name of the body part of which an ultrasound image is desired to be acquired by the medical expert.

The ultrasound diagnosis apparatus 300 may receive the information used to determine the reference location from the external device 2160, in operation 2130. The ultrasound diagnosis apparatus 300 may acquire the reference location, based on the information used to determine the reference location. The ultrasound diagnosis apparatus 300 may determine whether the location of the probe corresponds to the reference location. When the probe location corresponds to the reference location, the ultrasound diagnosis apparatus 300 may perform a predetermined operation, in operation 2140. For example, the ultrasound diagnosis apparatus 300 may inform the user that the location of the probe corresponds to the reference location, according to a predetermined method. The ultrasound diagnosis apparatus 300 may also acquire an ultrasound image from the reference location. The ultrasound diagnosis apparatus 300 may transmit the acquired ultrasound image to a remote user. The ultrasound diagnosis apparatus 300 may transmit at least one selected from the ultrasound image acquired at the reference location and the image displayed on the display unit to the external device 2160, in operation 2150. The image displayed on the display unit may include a menu display region and measurement values acquired by the ultrasound diagnosis apparatus 300. The medical expert may diagnose the inspection target, based on the information received by the external device 2160.

Figure 14:
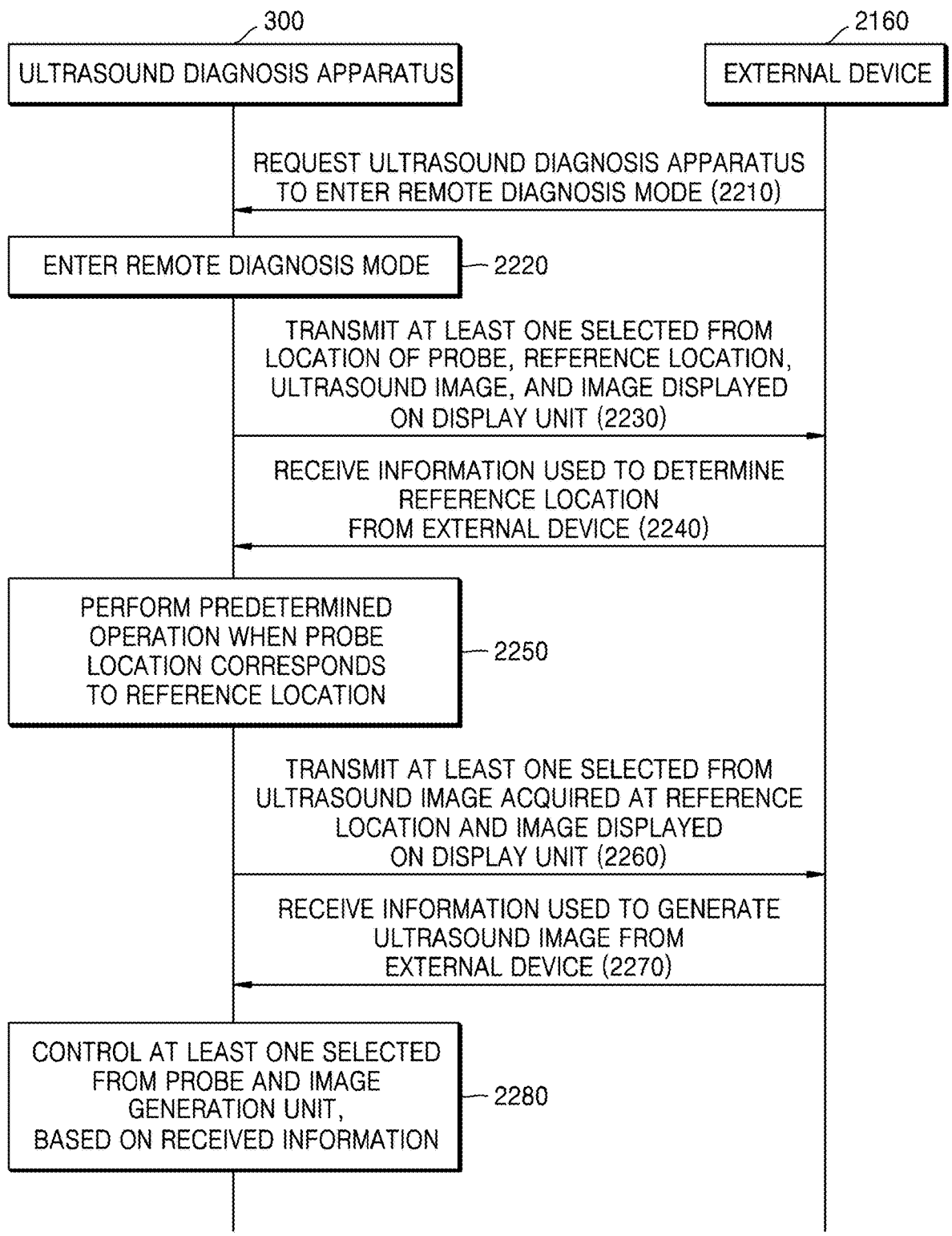
FIG. 14 is a process flow diagram of a method in which an ultrasound diagnosis apparatus interoperates with an external device, according to an embodiment of the disclosure.

FIG. 14 is a process flow diagram of a method in which the ultrasound diagnosis apparatus 300 interoperates with the external device 2160, according to an embodiment of the disclosure. FIG. 14 is a more detailed process flow diagram of FIG. 13, and thus repeated descriptions thereof will be omitted here.

The external device 2160 may request the ultrasound diagnosis apparatus 300 to enter a remote diagnosis mode, in operation 2210. For example, when a user of the ultrasound diagnosis apparatus 300 wants to be diagnosed by a remote medical expert, the user may request the remote medical expert for a remote medical examination. The remote medical expert may determine that an ultrasound image is necessary for a diagnosis. In this case, the remote medical expert may request the ultrasound diagnosis apparatus 300 to acquire an ultrasound image, via the external device 2160.

The ultrasound diagnosis apparatus 300 may enter a remote diagnosis mode, based on a request of the external device 2160, in operation 2220. The ultrasound diagnosis apparatus 300 may transmit at least one selected from the location of the probe, the reference location, the ultrasound image, and the image displayed on the display unit to the external device 2160, in operation 2230. The ultrasound diagnosis apparatus 300 may receive the information used to determine the reference location from the external device 2160, in operation 2240. When the probe location corresponds to the reference location, the ultrasound diagnosis apparatus 300 may perform a predetermined operation, in operation 2250. The ultrasound diagnosis apparatus 300 may transmit at least one selected from an ultrasound image obtained at the reference location and the image displayed on the display unit to the external device 2160, in operation 2260. The ultrasound diagnosis apparatus 300 may receive information used to generate an ultrasound image from the external device 2160, in operation 2270. The control unit 320 may control at least one selected from the probe 310 and the image generation unit 350, based on the received information. The ultrasound diagnosis apparatus 300 may control at least one selected from the probe 310 and the image generation unit 350, based on the received information, in operation 2280.

For example, the control unit 320 may control a parameter including at least one selected from a gain, a penetrating depth, and a frequency of the probe 310, based on the received information. The control unit 320 may control a beamforming method such as timing adjustment of a beam, based on the received information. The control unit 320 may control image processing including at least one selected from noise removal, pixel interpolation, image continuation, and space composition to be performed, based on the received information.

FIGS. 15-22 explain a menu selecting method according to an embodiment of the disclosure.

According to an embodiment of the disclosure, a user may need to select a plurality of menus to use an ultrasound diagnosis apparatus. For example, the user may select a plurality of menus in hierarchical orders illustrated in FIGS. 15 and 19.

The user may be skilled or unskilled at using ultrasound diagnosis apparatuses.

According to an embodiment of the disclosure, the user may select a mode of a menu that is provided by the ultrasound diagnosis apparatus, according to his or her skill. For example, the menus displayed in FIGS. 16-18 may be provided by the ultrasound diagnosis apparatus when the user is a skilled user. The menus displayed in FIGS. 20-22 may be provided by the ultrasound diagnosis apparatus when the user is an unskilled user.

Figure 15:
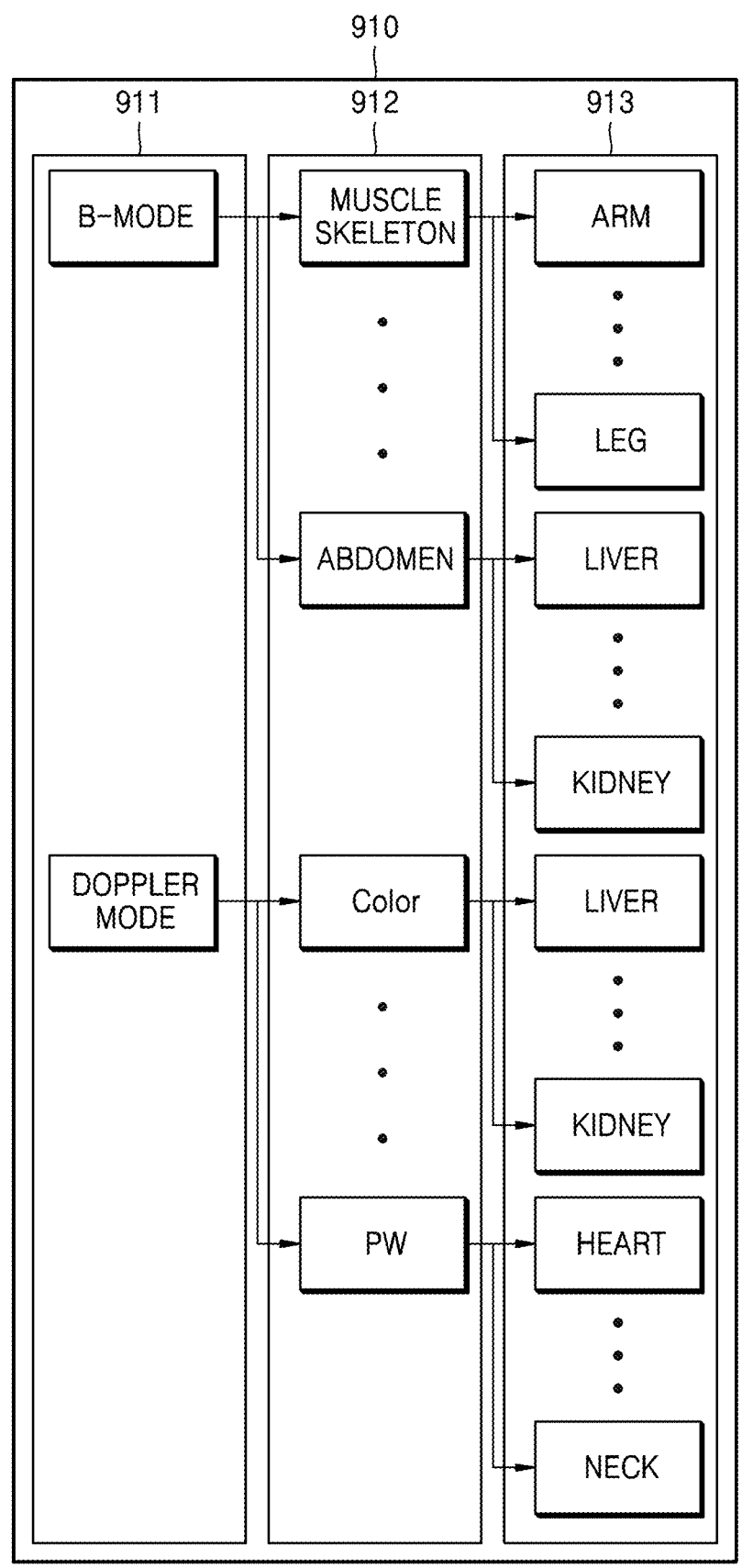
FIG. 15 explains a menu that may be provided when a user skilled at using ultrasound diagnosis apparatuses uses an ultrasound diagnosis apparatus.

FIG. 15 explains a menu that may be provided when a user skilled at using ultrasound diagnosis apparatuses uses an ultrasound diagnosis apparatus.

A selection menu on a general ultrasound diagnosis apparatus may be provided according to a hierarchical structure as illustrated in a block 910 of FIG. 15. In other words, a user may select one item from a block 911, select one item from a block 912, and then select one item from a block 913. For example, when the user wants to obtain an ultrasound image of a liver, the user may select a menu in an order of a B mode, an abdomen, and a liver. When the user wants to obtain an image of a flow of the blood within a heart, the user may sequentially select a Doppler mode, a color, and a heart.

For example, referring to FIG. 15, when using the ultrasound diagnosis apparatus 300, the user may select an image mode of the ultrasound diagnosis apparatus 300 and a body part of which an image is to be acquired. The block 910 indicates a hierarchical structure. The user may select from an uppermost menu to a lowermost menu. The block 911 may be a list representing an uppermost menu. The block 911, which is a list of an uppermost menu, may include at least one item from among a B-mode and a Doppler mode.

The block 912 may represent a list of a lower menu of the block 911. The block 912 may include at least one item from among a muscle skeleton, abdomen, a color, and a PW. The color denotes a color Doppler image, and the PW denotes a spectral Doppler image. A lower list of the B-mode item of the block 911 may include at least one item from among the muscle skeleton and the abdomen included in the block 912. A lower list of the Doppler mode item of the block 911 may include at least one from among the color and the PW included in the block 912.

The block 913 may represent a list of a lower menu of the block 912. The block 913 may include at least one item from among an arm, a leg, a liver, and a kidney. A lower list of the muscle skeleton item of the block 912 may include at least one item from among the arm and the leg included in the block 913. It may be easy for a skilled user having background knowledge about ultrasound diagnosis apparatuses to select a hierarchical menu in the order of the block 911, the block 912, and the block 913. Thus, the ultrasound diagnosis apparatus 300 may provide a menu for selecting a hierarchical menu in the order of the block 911, the block 912, and the block 913, to a skilled user.

Figure 16:
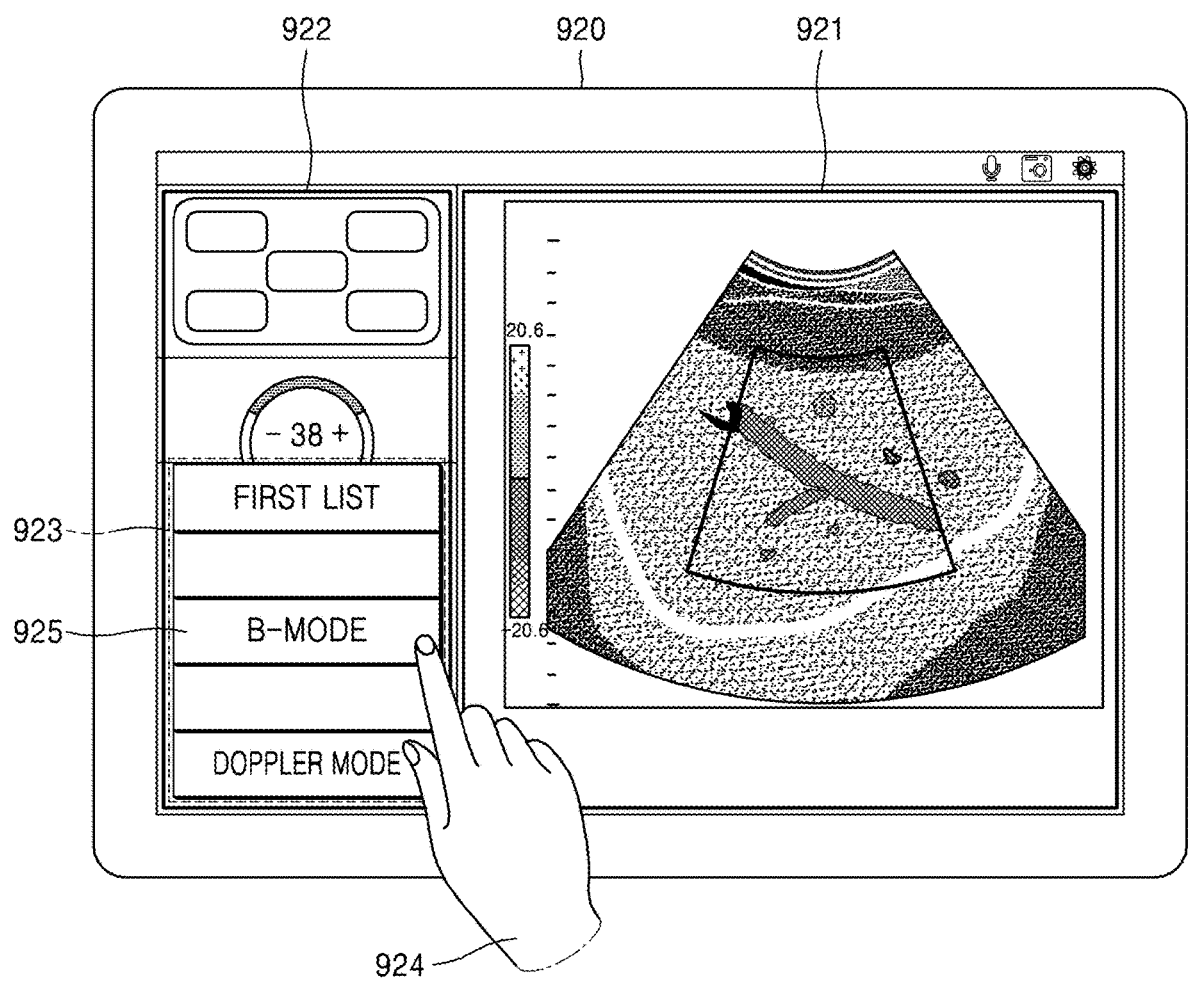
FIG. 16 explains a menu that may be provided when a user skilled at using ultrasound diagnosis apparatuses uses an ultrasound diagnosis apparatus.
Figure 17:
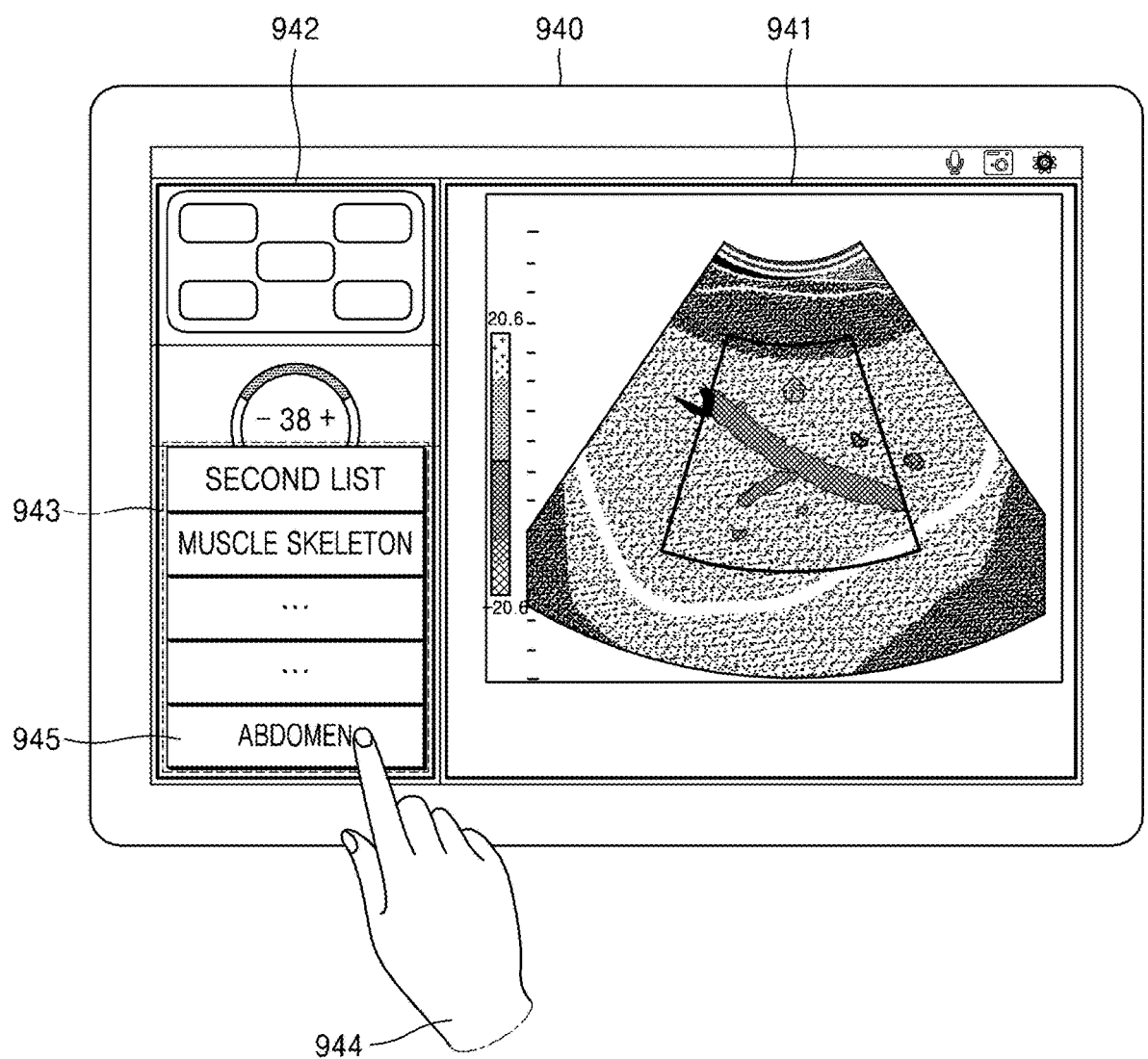
FIG. 17 explains a menu that may be provided when a user skilled at using ultrasound diagnosis apparatuses uses an ultrasound diagnosis apparatus.
Figure 18:
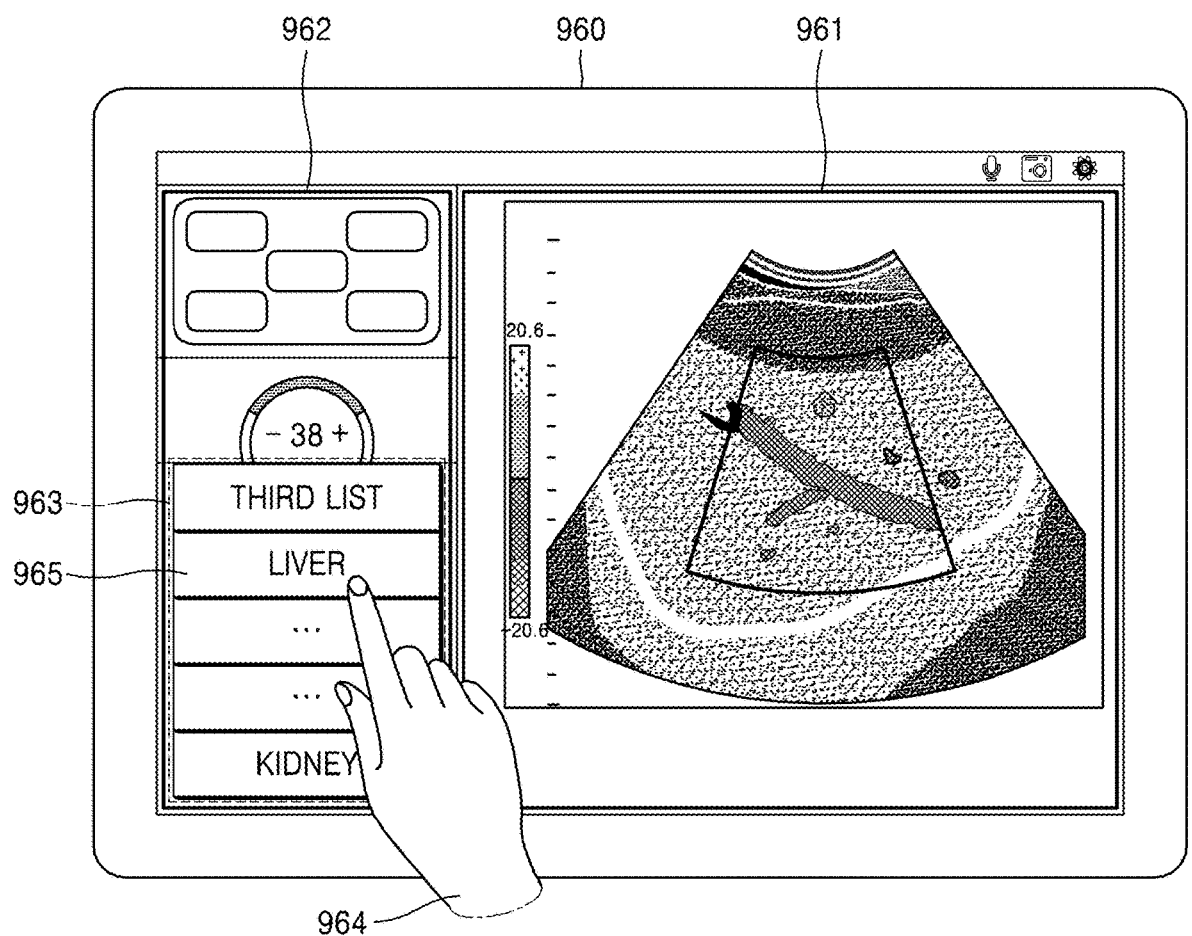
FIG. 18 explains a menu that may be provided when a user skilled at using ultrasound diagnosis apparatuses uses an ultrasound diagnosis apparatus.

FIGS. 16-18 explain menus that may be provided when a user skilled at using ultrasound diagnosis apparatuses uses an ultrasound diagnosis apparatus.

FIG. 16 illustrates a display unit 920 displaying a menu selection screen image, according to an embodiment of the disclosure. The display unit 920 may include an ultrasound image display region 921 and a menu display region 922.

The menu display region 922 may display a list corresponding to the block 911. For example, the menu display region 922 may include a first list 923, which is a list of image modes. The first list 923 may include at least one item from among a B-mode and a Doppler mode. For example, a user 924 may select a B mode item 925 from the first list 923.

FIG. 17 is a subsequent view of FIG. 16, and illustrates a screen image displayed on a display unit 940 after the user 924 selects the B mode item 925. The display unit 940 may include an ultrasound image display region 941 and a menu display region 942. The menu display region 942 may display a list of the block 912, which is a lower list of the block 911. For example, the menu display region 942 may include a second list 943. The second list 943 may include at least one item from among the muscle skeleton and the abdomen which are included in a body part list. For example, a user 944 may select an abdomen item 945 from the second list 943.

FIG. 18 is a subsequent view of FIG. 17, and illustrates a screen image displayed on a display unit 960 after the user 944 selects the abdomen item 945. The display unit 960 may include an ultrasound image display region 961 and a menu display region 962. The menu display region 962 may display a list of the block 913, which is a lower list of the block 912. The menu display region 962 may display a list of detailed body parts. The user 964 may select one from the items included in the detailed body part list. For example, the menu display region 962 may include a third list 963. The third list 963 may include at least one item from among the liver and the kidney which are included in the detailed body part list. For example, a user 964 may select a liver item 965 from the third list 963. The ultrasound diagnosis apparatus 300 may determine a reference location, based on a selection by the user 964. The ultrasound diagnosis apparatus 300 may display information including at least one selected from a location of a probe, a path, and the reference location. The user 964 may position the probe 310 at the reference location, based on the information displayed on the display unit 960.

Even when at least one is selected from the first through third lists by a user in FIGS. 15-18, the ultrasound diagnosis apparatus 300 may acquire an ultrasound image from a reference location. For example, since a skilled user is able to know a reference location enabling an optimal ultrasound image to be acquired for a body part of which an ultrasound image is to be acquired, the skilled user may not need a reference location that is provided by the ultrasound diagnosis apparatus 300. The skilled user may select a B mode from the first list 923 as in FIG. 16, but may select no items from the second list 943 and the third list 963. The skilled user may acquire an ultrasound image of the B mode by positioning a probe at the reference location on the body of an inspection target.

However, a user unskilled at using the ultrasound diagnosis apparatus 300 may not know a location of the probe that is suitable to acquire an ultrasound image, and a method of setting a function of the ultrasound diagnosis apparatus 300 that is suitable for a body part of which an ultrasound image is desired to be acquired. For example, the unskilled user may want to acquire an ultrasound image of a liver. In this case, when the first list 923 for selecting a B mode or a Doppler mode is first displayed to the unskilled user, the unskilled user may not know what to select from the first list 923 in order to perform ultrasound measurement on a liver. In addition, the unskilled user has difficulty in knowing at which location the probe is to be positioned in order to acquire an ultrasound image of the liver.

Thus, the ultrasound diagnosis apparatus 300 may enable a user to select, according to his or her skill, a mode of a menu that is provided by the ultrasound diagnosis apparatus 300.

Figure 19:
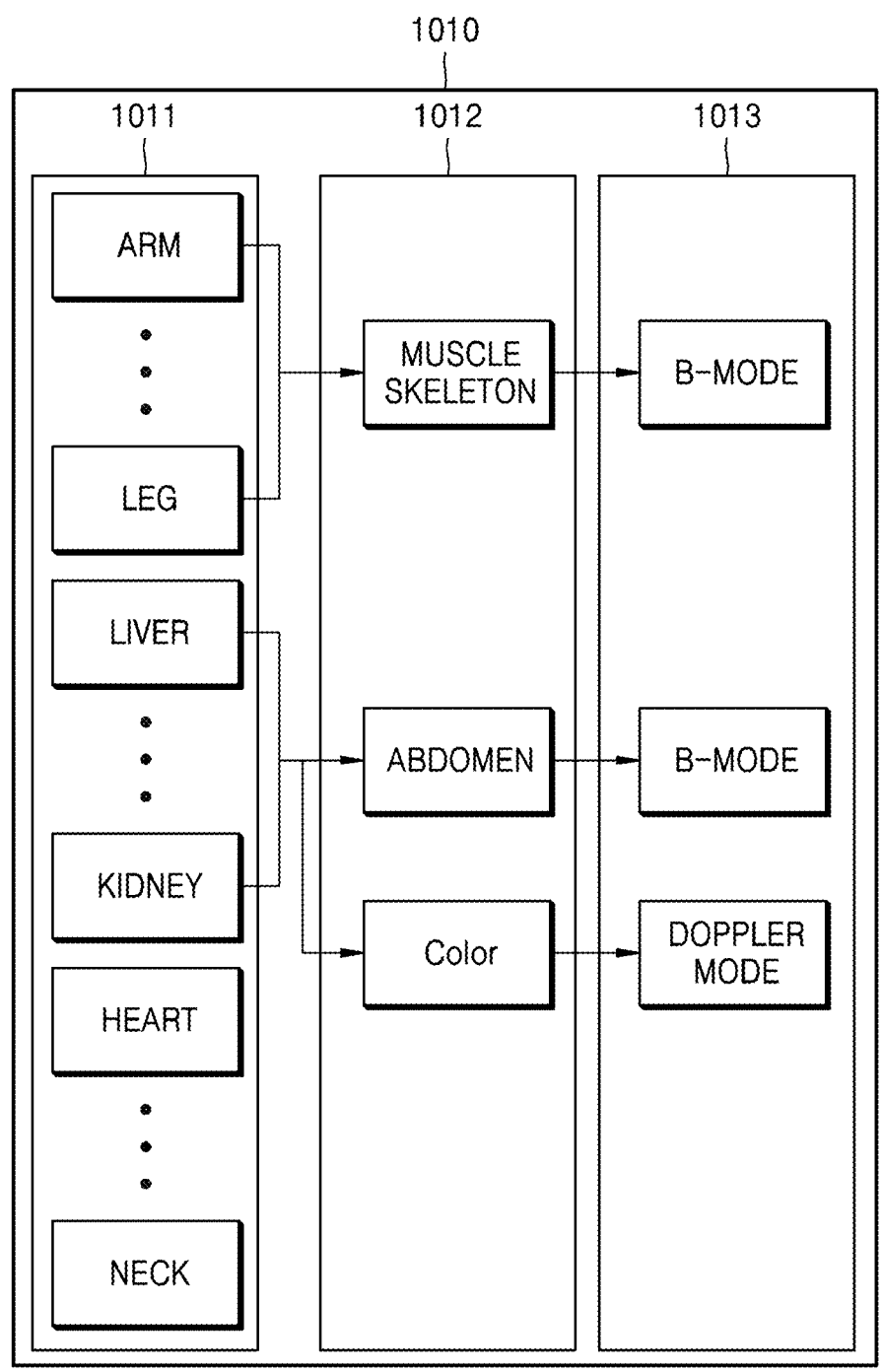
FIG. 19 explains a menu that may be provided when a user unskilled at using ultrasound diagnosis apparatuses uses an ultrasound diagnosis apparatus.

FIG. 19 explains a menu that may be provided when a user unskilled at using ultrasound diagnosis apparatuses uses an ultrasound diagnosis apparatus.

Figure 20:
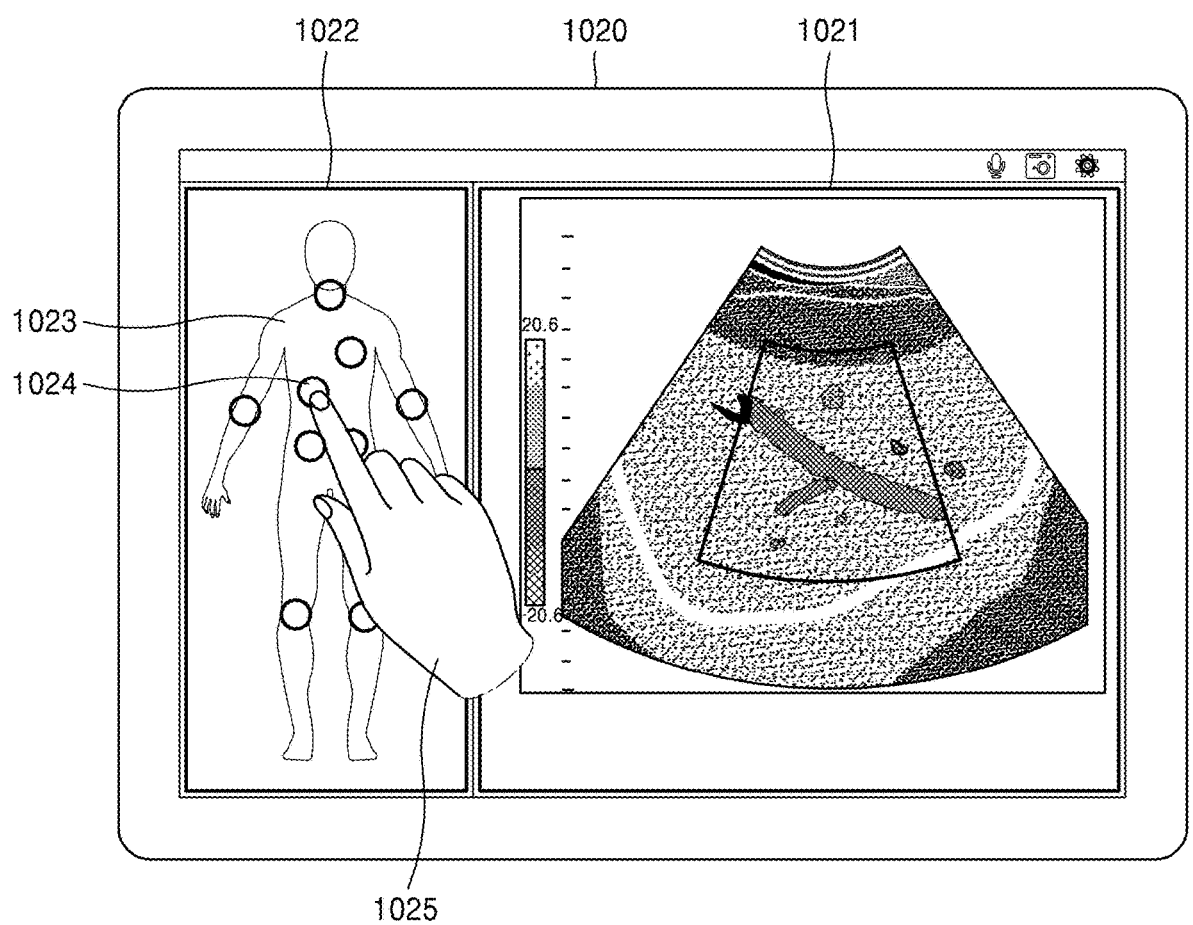
FIG. 20 explains a menu that may be provided when a user unskilled at using ultrasound diagnosis apparatuses uses an ultrasound diagnosis apparatus.
Figure 21:
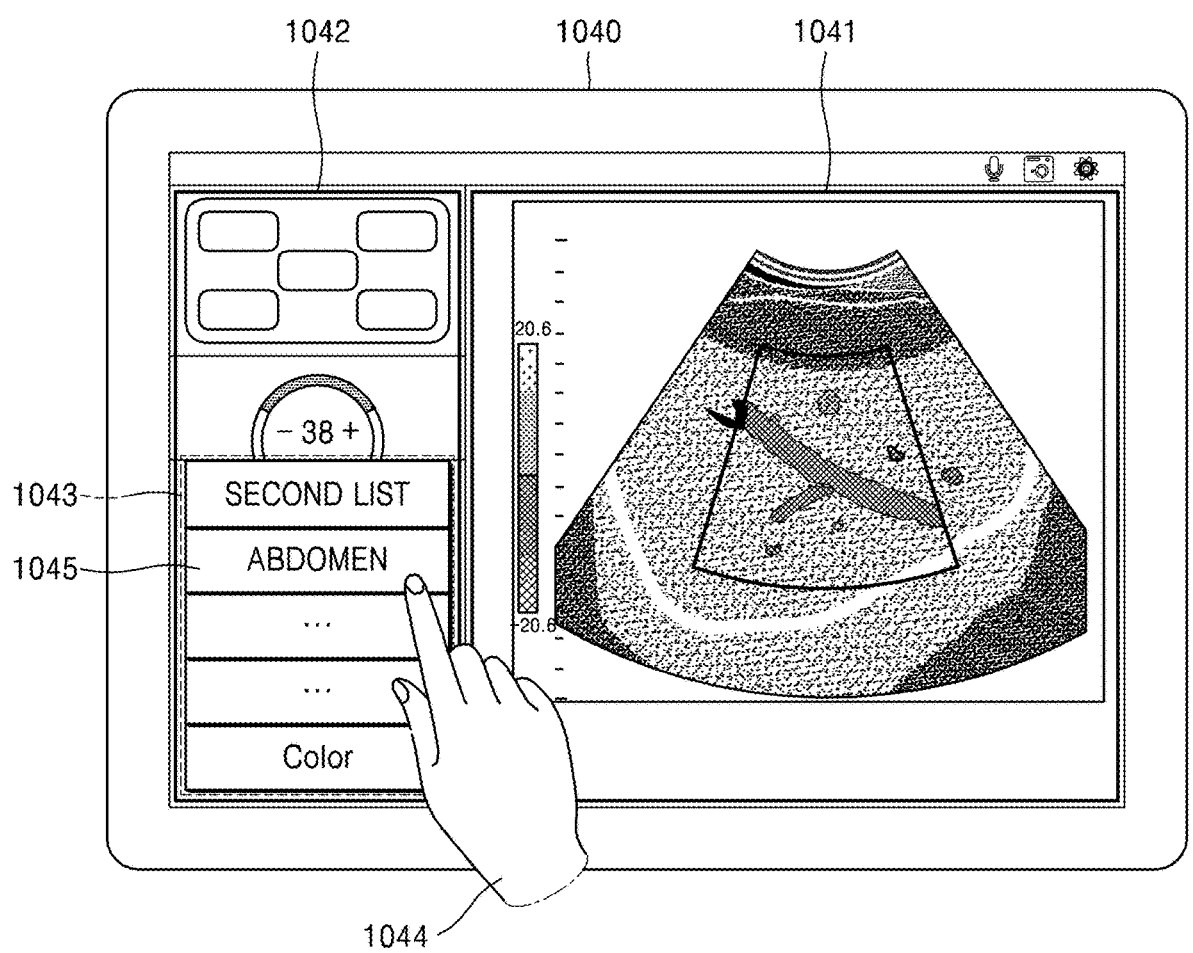
FIG. 21 explains a menu that may be provided when a user unskilled at using ultrasound diagnosis apparatuses uses an ultrasound diagnosis apparatus.
Figure 22:
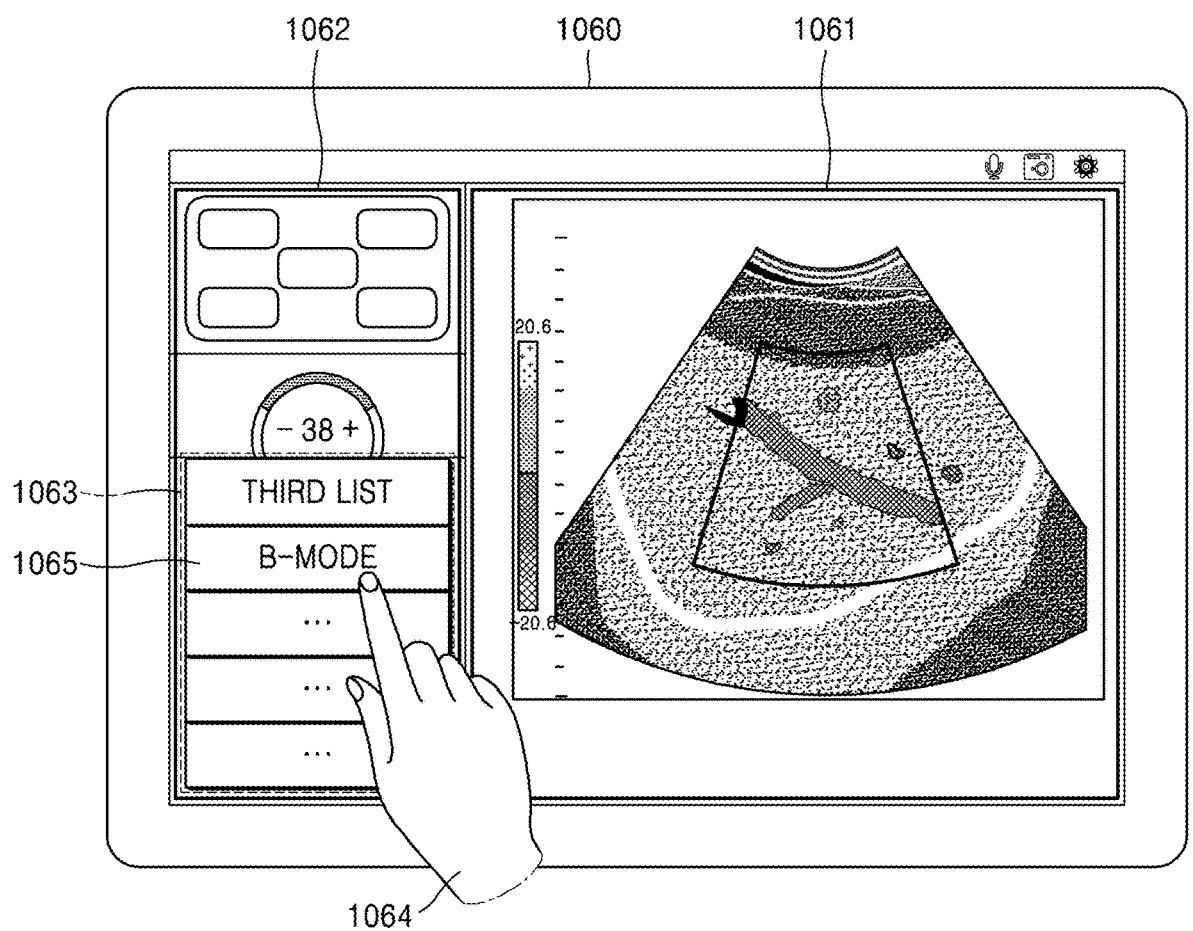
FIG. 22 explains a menu that may be provided when a user unskilled at using ultrasound diagnosis apparatuses uses an ultrasound diagnosis apparatus.

FIGS. 20-22 explain menus that may be provided when a user unskilled at using ultrasound diagnosis apparatuses uses an ultrasound diagnosis apparatus. According to an embodiment of the disclosure, the ultrasound diagnosis apparatus 300 may enable a user to first select a body part of which an ultrasound image is to be acquired.

The selection by the user may be based on a hierarchical menu that is provided by the ultrasound diagnosis apparatus 300. A block 1010 indicates a hierarchical structure. A user may select a lowermost menu from an uppermost menu. A block 1011 may be a list representing an uppermost menu. The block 1011, which is a list of an uppermost menu, may include at least one item from among an arm, a leg, a liver, a kidney, a heart, and a neck. The user may select a detailed body part of which an ultrasound image is to be acquired, from among the items listed in the block 1011, which is the uppermost menu list.

A block 1012 may represent a list of a lower menu of the block 1011. The block 1012 may include at least one item from among a muscle skeleton, abdomen, and a color. A lower list of the liver item of the block 1011 may include at least one item from among the abdomen and the color included in the block 1012. The color denotes a color Doppler image.

A block 1013 may represent a list of a lower menu of the block 1012. The block 1013 may include at least one item from among a B-mode and a Doppler mode. A lower list of the muscle skeleton item of the block 1012 may include a B-mode item included in the block 1013.

Users having no background knowledge about ultrasound diagnosis apparatuses have difficulty in knowing an image mode that is to be selected in order to an ultrasound image of a predetermined body part, and a location at which a probe is to be positioned. Thus, the ultrasound diagnosis apparatus 300 may provide a hierarchical menu in the order of the block 1011, the block 1012, and the block 1013 such that even unskilled users may easily set a function of the ultrasound diagnosis apparatus 300.

FIG. 20 illustrates a display unit 1020 displaying a menu selection screen image, according to an embodiment of the disclosure. The display unit 1020 may include an ultrasound image display region 1021 and a menu display region 1022. The ultrasound diagnosis apparatus 300 may display a body part selection menu on the menu display region 1022. A user 1025 may select a predetermined body part from the body part selection menu in order to acquire an image of the predetermined body part. The ultrasound diagnosis apparatus 300 may select a reference location corresponding to the selected body part.

According to an embodiment of the disclosure, the ultrasound diagnosis apparatus 300 may display the body part selection menu on the menu display region 1022, in the form of a list. For example, the menu display region 1022 may display a first list (not shown) corresponding to the block 1011. In other words, the first list is a list of detailed body parts and thus may include at least one item from among an arm, a leg, a liver, a kidney, and a heart. For example, the user 1025 may select a liver item (not shown) from the third list.

According to an embodiment of the disclosure, as shown in FIG. 20, the ultrasound diagnosis apparatus 300 may not display the body part selection menu in the form of a list, but may display the body part selection menu on an image 1023 representing the object. A plurality of body parts may be displayed on the image 1023 representing the object. For example, a plurality of circular icons, such as a body part 1024, may be displayed. The plurality of body parts may be locations corresponding to the items of the block 1011, respectively. For example, the user 1025 may select the body part 1024 from among the plurality of body parts displayed on the image 1023 representing the object. The body part 1024 may be a liver. Although not shown in FIG. 20, when the user 1025 selects the body part 1024, the display 1020 may represent that the liver has been selected, via a text. By displaying body parts of which ultrasound images are to be acquired on the image 1023 representing the object as described above, users may more easily select a body part of which an ultrasound image is to be acquired. Moreover, users may easily recognize visually where to locate the probe 310.

The ultrasound diagnosis apparatus 300 may acquire a location of the probe 310. The ultrasound diagnosis apparatus 300 may determine whether the location of the probe 310 corresponds to the reference location 1024 selected by the user 1025. When it is determined that the location of the probe 310 does not correspond to the reference location 1024 selected by the user 1025, the ultrasound diagnosis apparatus 300 may display a path on the image 1023 representing the object.

FIG. 21 is a subsequent view of FIG. 20, and illustrates a screen image displayed on a display unit 1040 after the user 1025 selects the body part 1024. The display unit 1040 may include an ultrasound image display region 1041 and a menu display region 1042. The menu display region 1042 may display a list of the block 1012, which is a lower list of the block 1011. For example, the menu display region 1042 may include a second list 1043. The second list 1043 may include at least one item from among an abdomen and a color. For example, a user 1044 may select an abdomen item 1045 from the second list 1043.

FIG. 22 is a subsequent view of FIG. 21, and illustrates a screen image displayed on a display unit 1060 after the user 1044 selects the abdomen item 1025. A menu display region 1062 may display a list of the block 1013, which is a lower list of the block 1012. For example, the menu display region 1062 may include a third list 1063. The third list 1063 may include a B-mode item. For example, a user 1064 may select a B mode item 1065 from the third list 1063. When the user 1064 selects the B-mode item 1065, an ultrasound image display region 1061 of the display 1060 may display an image corresponding to an ultrasound B mode.

When a user is unskilled at using the ultrasound diagnosis apparatus 300, although a body part selected from the menu display region 1022 of the ultrasound diagnosis apparatus 300 by the user is a liver, the user may actually position the probe 310 at a location that is not the location of a liver. In this case, an ultrasound image displayed on the ultrasound image display region 1061 is not an ultrasound image of the liver. Accordingly, as described above with reference to FIGS. 5-9C, when the location of the probe 310 is different from the reference location, the control unit 320 may guide the probe 310 to be positioned at the liver which is the reference location.

Even when at least one is selected from the first through third lists by the user, the control unit 320 may control an ultrasound image to be acquired from the reference location. For example, the user may select a liver from detailed body parts included in the first list, but may select no items from the second list 1043 and the third list 1063. The ultrasound diagnosis apparatus 300 may acquire a reference location, based on the selected body part. The ultrasound diagnosis apparatus 300 may automatically select an ultrasound image mode that is adequate to acquire an ultrasound image of the liver. For example, the ultrasound image mode may be a B mode.

The ultrasound diagnosis apparatus 300 may display the acquired reference location on the display unit 340. The user may position the probe 310 at the reference location while checking the display unit 340. The ultrasound diagnosis apparatus 300 may acquire an ultrasound image when the probe 310 is positioned at the reference location.

The ultrasound diagnosis apparatus 300 may set information that is used to generate an ultrasound image, according to a body part selected by the user as a body part of which an ultrasound image is to be acquired. For example the ultrasound diagnosis apparatus 300 may set a parameter including at least one selected from a gain, a penetrating depth, and a frequency of a predetermined probe, based on the body part of which an ultrasound image is to be acquired. The ultrasound diagnosis apparatus 300 may set a beam-forming method as a predetermined method, based on the body part of which an ultrasound image is to be acquired. The ultrasound diagnosis apparatus 300 may perform image processing including at least one selected from noise removal, pixel interpolation, image continuation, and space composition, based on the body part of which an ultrasound image is to be acquired.

Figure 23:
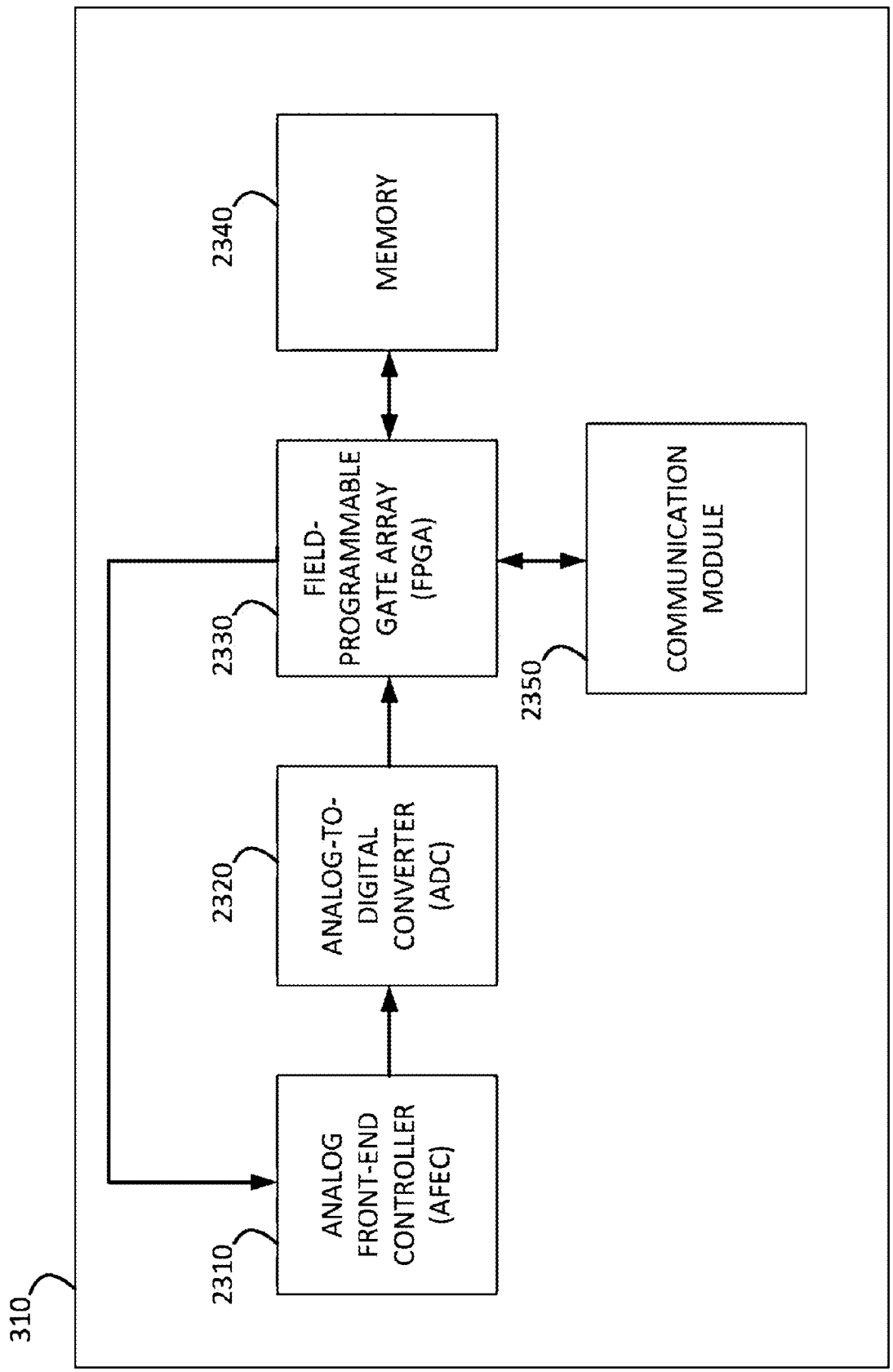
FIG. 23 is a block diagram of a wireless probe according to an embodiment of the disclosure.

FIG. 23 is a block diagram of a wireless probe according to an embodiment of the disclosure. As shown in FIG. 23, the probe 310 may include an analog front-end controller (AFEC) 2310, an analog-to-digital converter (ADC) 2320, a field-programmable gate array (FPGA) 2330, a memory 2340, and a communication module 2350. The AFEC 2310, the ADC 2320, the FPGA 2330, the memory 2340, and the communication module 2350 are implemented in hardware, firmware, or a combination of hardware and software. The probe 310 and the components of the probe 310 are described in association with Kim et al., "Design and Implementation of a 128-Channel Wireless Handheld Probe for Ultrasound Medical Imaging"; Kim et al., "A CMOS Receiver ASIC for Wireless Handheld Ultrasound Imaging System"; and Kim et al., "A High Voltage CMOS Pulser Combined with a T/RX Switch for Wireless Handheld Ultrasound Imaging System", all of which are incorporated by reference herein in their entirety.

Although embodiments herein describe the FPGA 2330, in other embodiments, operations carried out by the FPGA 2330 may be implemented by a central processing unit (CPU), a graphics processing unit (GPU), an accelerated processing unit (APU), a microprocessor, a microcontroller, a digital signal processor (DSP), an application-specific integrated circuit (ASIC), or another type of processing component. Further, although some embodiments herein describe the probe 310 as a 128-channel probe, it should be understood that other embodiments include a different number of channels, such as 64 channels, 256 channels, etc.

Memory 2340 includes a random access memory (RAM), a read only memory (ROM), and/or another type of dynamic or static storage device (e.g., a flash memory, a magnetic memory, and/or an optical memory) that stores information and/or instructions for use by the FPGA 2330.

Communication module 2350 includes a transceiver-like component (e.g., a transceiver and/or a separate receiver and transmitter) that enables the probe 310 to communicate with other devices, such as via a wired connection, a wireless connection, or a combination of wired and wireless connections. Communication module 2350 may permit the probe 310 to receive information from another device and/or provide information to another device. For example, the communication module 2350 may include an Ethernet interface, an optical interface, a coaxial interface, an infrared interface, a radio frequency (RF) interface, a universal serial bus (USB) interface, a Wi-Fi interface, a cellular network interface, or the like.

The probe 310 may be controlled to execute one or more processes described herein. The probe 310 may perform these processes under control of the FPGA 2330 executing software instructions stored by a non-transitory computer-readable medium, such as the memory 2340 and/or another storage component. A computer-readable medium is defined herein as a non-transitory memory device. A memory device includes memory space within a single physical storage device or memory space spread across multiple physical storage devices.

Software instructions may be read into the memory 2340 from another computer-readable medium or from another device via the communication module 2350. When executed, software instructions stored in the memory 2340 may cause the FPGA 2330 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 23 are provided as an example. In practice, the probe 310 may include additional components, fewer components, different components, or differently arranged components than those shown in FIG. 23. Additionally, or alternatively, a set of components (e.g., one or more components) of the probe 310 may perform one or more functions described as being performed by another set of components of the probe 310.

Figure 24:
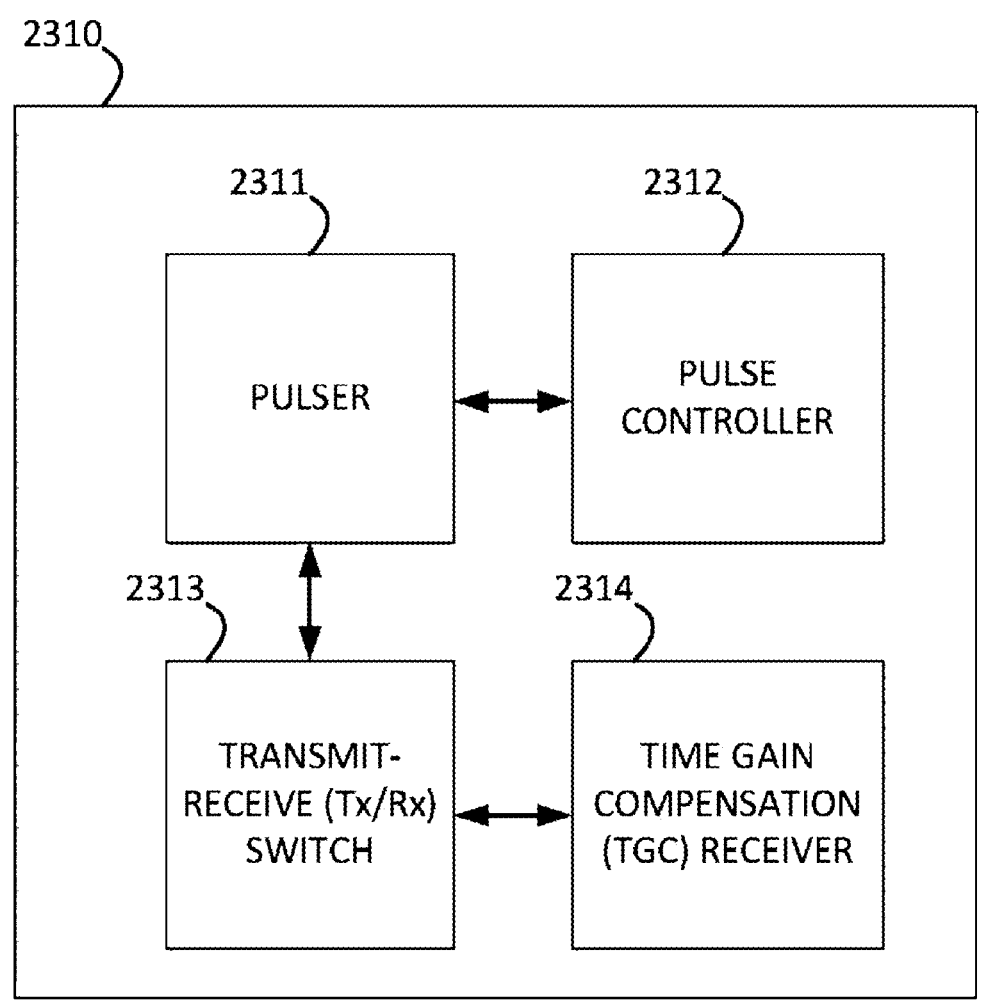
FIG. 24 is a block diagram of an analog front-end controller (AFEC) of a wireless probe according to an embodiment of the disclosure.

FIG. 24 is a block diagram of an analog front-end controller (AFEC) of a wireless probe according to an embodiment of the disclosure. As shown in FIG. 24, the AFEC 2310 includes a pulser 2311, a pulse controller 2312, a transmit/receive (Tx/Rx) switch 2313, and a time gain compensation (TGC) receiver 2314.

According to an embodiment, the pulser 2311 may include a Tx level shifter, an input buffer, an active clamp switch, and high voltage output driver stages. The Tx level shifter may receive an analog signal from a Tx pattern generator, and amplify the analog signal to adjust a high voltage MOSFET (HVMOS) transistor. The active clamp switch reduces deleterious effects introduced during digital-to-analog signal conversion in the Tx pattern generator, thereby improving image quality. The final stage high voltage PMOS and NMOS transistors generate high voltage rectangular signals by generating high DC voltage of +40 volts (V) and −40 V. According to an embodiment, two transistors include a same turn-on resistance in order to permit a balance between positive and negative sides of the pulse in the situation of temperature and supply voltage variation.

According to an embodiment, the Tx/Rx switch 2313 is configured to be set to an on state during an Rx mode, and an off state during a Tx mode. A level shifter is configured to adjust the transistors of the Tx/Rx switch between on and off states. For example, an output voltage of the level shifter adjusts between −40 V and +5 V based on an Rx-enabling signal.

The Tx/Rx switch is configured with an output capacitor size that permits a reduction in signal distortion during switching between the Tx mode and the Rx mode. Additionally, the Tx/Rx switch 2313 is configured to include a turn-on resistance that reduces thermal noise and recovery time during transitions between the Tx mode and the Rx mode, and between the Rx mode and the Tx mode.

According to an embodiment, the TGC receiver 2314 is configured to operate in association with an analog decoder and an attenuator. The analog decoder may receive digital signals from the FPGA 2330, and convert the digital signals into on signals and off signals for the attenuator. As an example, the analog decoder may receive five (5) digital signals, and convert the five digital signals into thirty two (32) on and off signals. The attenuator controls a gain range of the TGC receiver 2314 with discrete gain steps of 1.5 decibels (dB). The TGC receiver 2314 is configured to implement gain control using an internal timer and serial peripheral interface (SPI) control data received from the FPGA 2330.

According to an embodiment, the TGC receiver 2314 is configured to include active loads at each stage in order to control gain of the amplifier by using a pair of MOS transistors. The TGC receiver 2314 is configured to adjust a gain based on controlling an on-resistance of an active MOS transistor. The first two stages in the TGC receiver 2314 are configured with a PMOS common source topology in order to permit low 1/f noise performance. The main transistor size in the first stage is configured to a trade-off between noise reduction and a total size of the TGC receiver 2314.

According to an embodiment, the TGC receiver 2314 is configured with a beamformer to align the phase of signals received from various transducer elements by delaying and summing output signals of the receiver circuit. The beamformer is configured to be implemented in either analog or digital topologies. According to an embodiment, the delay resolution is configured to be 12.5 ns (80 MHz) or 25 ns (40 MHz). In this way, the maximum delay range is configured to be 1.25 μs or 2.5 μs, respectively. The delay block is configured to include one hundred (100) delay lines, which are composed of sample-and-hold stages with a digital controller. A metal-insulator-metal (MIM) capacitor is configured to reduce signal distortion. According to an embodiment, signal summation is performed by controlling write and read clocks of the delay block. After passing through pipelined delay blocks, an operational amplifier integrates the received signals for n-channels. In this way, the signal gain of the summing block is increased.

According to an embodiment, the TGC receiver 2314 is fabricated using a 0.35 CMOS process. According to experimental results, such a configuration permits second and third harmonic distortion against fundamental signals of 56 dBc for a 350 mV$_{pp}$ output signal. A gain range of 6 boards provided more than 55 dB by changing an on-resistance of active loads in the TGC receiver 2314 with a control voltage range from −3.3 V to +3.3 V. Also, a gain variation range provided less than ±1 dB for 6 test boards. For second and third harmonics, linearity shows more than 40 dBc at a middle level gain of 19 dB with greater than 42 dBc of signal-to-noise ratio (SNR). In order to avoid crosstalk, the TGC receiver 2314 is configured with another metal layer option in the CMOS process for a ground-shield. Thus, the digital clock harmonics are configured to be isolated from the analog receiver signal path.

In this way, some embodiments herein provide a TGC receiver ASIC using a 0.35 μm CMOS process. The TGC receiver employs a TGC and an analog sample-and-hold beamformer for a wireless ultrasound diagnostic system. Measured results show more than 55 dB of gain range and excellent harmonic properties for the TGC. Also, the analog beamformer is configured with 100 delay lines in each channel, and an op-amp based signal integrator. The receiver provides greater than 40 dB of SNR with eliminated digital clock coupling effects by adding an additional ground metal layer.

Figure 25:
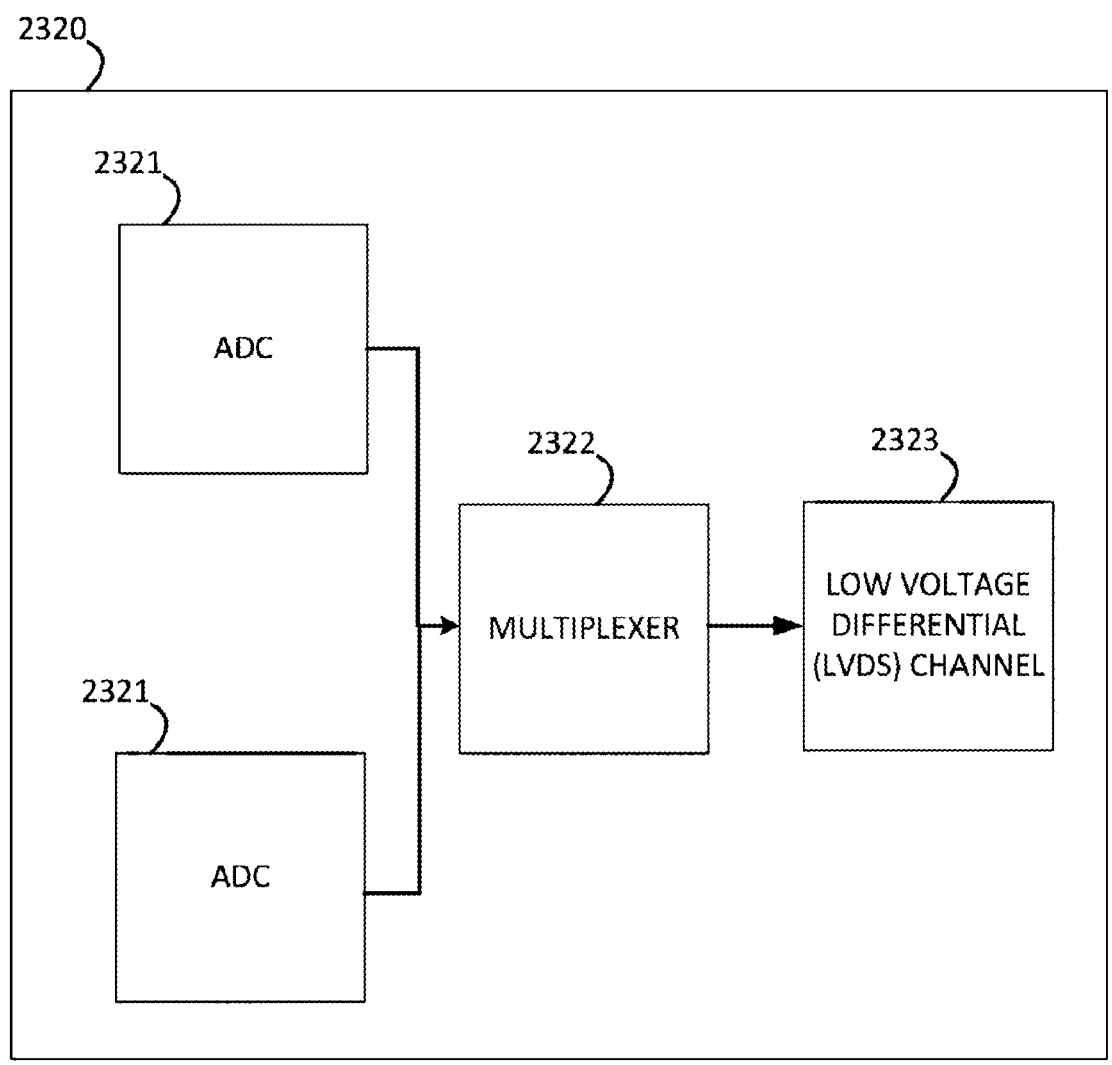
FIG. 25 is a block diagram of an analog-to-digital converter (ADC) of a wireless probe according to an embodiment of the disclosure.

FIG. 25 is a block diagram of an analog-to-digital converter (ADC) of a wireless probe according to an embodiment of the disclosure. As shown in FIG. 25, the ADC 2320 includes a set of ADCs 2321, a multiplexer 2322, and a low voltage differential (LVDS) channel 2323.

According to an embodiment, the ADC 2320 is configured with a single-to-differential buffer in the first stage of the ADC 2320. The ADC 2320 is configured with a Gm-C filter topology for the anti-aliasing filter (AAF). The AAF is configured as a second order fully differential biquad filter with transconductance elements. According to an embodiment, the transfer function of the biquad filter is represented as:

$$H(s) = \frac{\frac{g_{m1}g_{m3}}{C_1 C_2}}{s^2 + \frac{g_{m2}}{C_1}s + \frac{g_{m3}g_{m4}}{C_1 C_2}}$$

The above equation implies a gain of:

$$H(0) = \frac{g_{m1}}{g_{m4}}$$

According to an embodiment, DC gain is set to zero (0) dB by setting $g_{m1}=g_{m4}=g_m$. In an embodiment, the AAF is configured with a maximum corner frequency of ten (10) megahertz (MHz).

As an example, and for a ten (10) MHz band limited signal, the ADC 2320 is configured with an oversampling rate of twenty four (24) to permit a data rate of multiplexed output data to satisfy a maximum link rate of the LVDS channel 2323.

According to an embodiment, the ADC 2320 is configured with a modulator that includes a local feedback path, a main feedback path (e.g., two main feedback paths), and a feedforward path (e.g., three feedforward paths) to improve the phase response by inserting additional zeroes. The modulator filter is configured as a third order Gm-C filter using a transductor and a unit element. In this way, high unity gain and lower power operation are permitted. For example, the excess loop delay and closed loop feedback stability issues are reduced by the three feedforward paths of the architecture, and metastability is addressed by having two stages of comparator latches inside the quantizer. According to an embodiment, the ADC 2320 is configured with a 4-bit quantizer having minimal latency flash architecture and fifteen (15) comparators. To reduce clock jitter that would cause the DAC to raise the in-band noise floor, the ADC 2320 is configured with a 4-bit current steering DAC. In this way, noise energy per cycle and sensitivity to clock jitter are reduced.

According to an embodiment, the ADC 2320 is configured with a cascaded integrated comb (CIC) filter. To provide a sharper cutoff, the ADC 2320 is configured with a finite impulse response (FIR) filter in conjunction with the CIC filter. The ADC 2320 is configured with a parallel-to-serial interface to receive the twelve (12) bits output from the FIR filter at twenty (20) MHz. The serial output interface is configured to run at four hundred and eighty (480) MHz per channel. Two channels are muxed in order to decrease the overall number of input/output (I/O) pins. Serial data is transmitted in each clock edge, thereby providing a nine hundred and sixty (960) megabit per second (MB/s) data rate. The LVDS channel 2323 output interface is configured to drive the interconnection from the ADC 2320.

Figure 26:
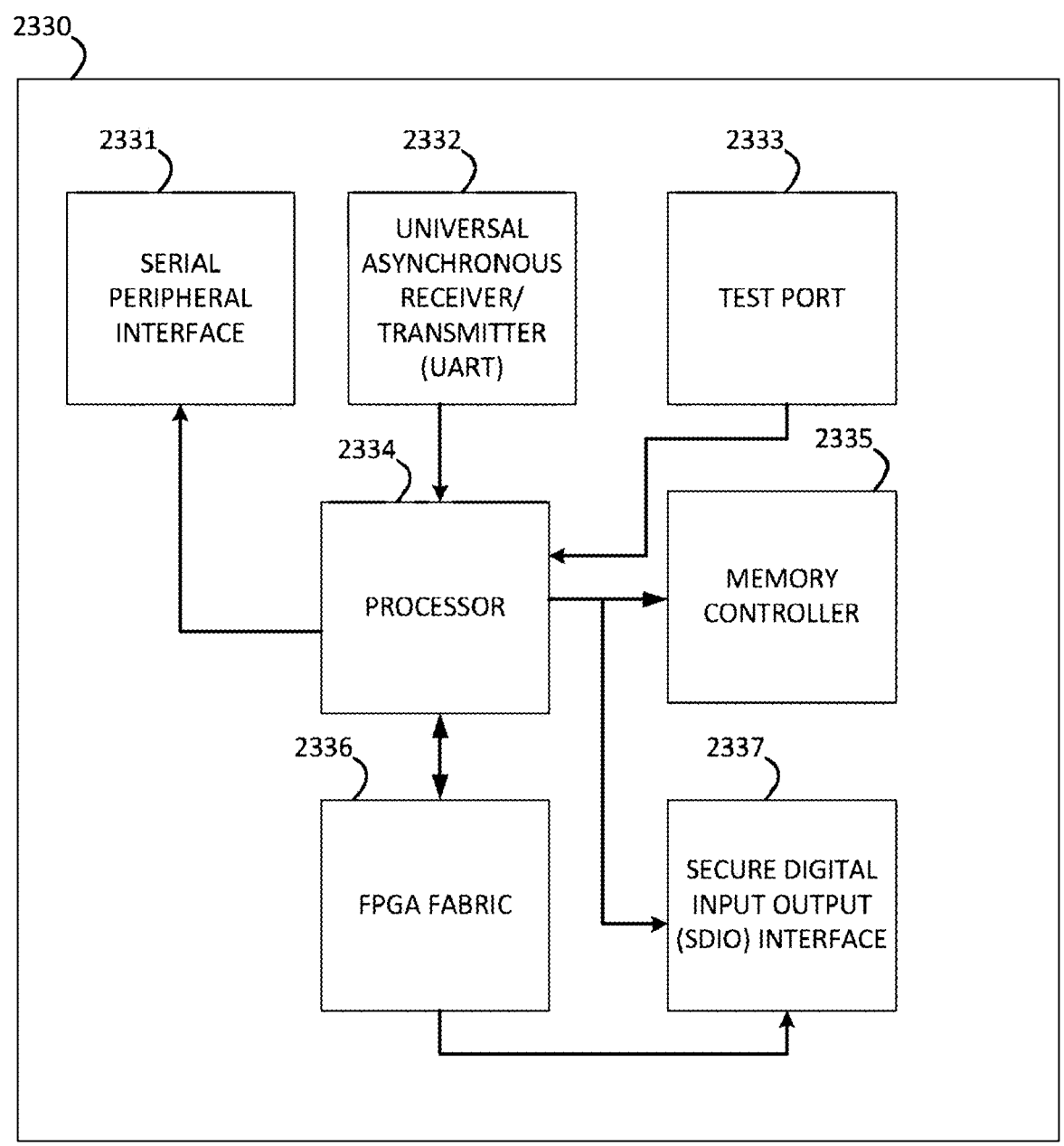
FIG. 26 is a block diagram of a field-programmable gate array (FPGA) of a wireless probe according to an embodiment of the disclosure.

FIG. 26 is a block diagram of a field-programmable gate array (FPGA) of a wireless probe according to an embodiment of the disclosure. As shown in FIG. 26, the FPGA 2330 includes a serial peripheral interface 2331, a universal asynchronous receiver/transmitter (UART) 2332, a test port 2333, a processor 2334, a memory controller 2335, an FPGA fabric 2336, and a secure digital input output (SDIO) interface 2337.

According to an embodiment, the FPGA 2330 includes a mid-end beamformer and back-end processing components. The mid-end beamformer is configured to delay signals in different channels and align signals before a summing operation is performed. The summed signal is provided to the back-end processing components to permit demodulation, envelope detection, and signal amplitude calculation. The FPGA 2330 is configured with a control block that generates control signals using pre-determined information.

According to an embodiment, local memory is updated by each scanline. Further, delay information is stored in external memory. The mid-end processing components of the FPGA 2330 include one hundred and twenty eight (128) paths, and the amount of delay for each path is dynamically set by a bulk delay component and a fractional delay component, sequentially. The FPGA 2330 is configured to set an apodization weight for each path.

According to an embodiment, a bulk delay component of the FPGA 2330 delays a signal by an integer number of sampling periods, and the fractional delay component is a polyphase filter that provides interpolated data using up-sampling. The apodization coefficients are multiples that assign signals different weights in different channels. According to an embodiment, the amount of data-log compression in the FPGA 2330 is 16×1024×128×30=63 Mbps, wherein 16 is the data bit-width, 1024 is the number of samples per scan lines, 128 is the number of scan lines per frame, and 30 is the frame rate, respectively.

According to an embodiment, the AFEC 2310 and the ADC 2320 were fabricated in association with 0.35 micrometer (μm) 100 V HV-CMOS and 0.13 μm standard CMOS processes. As a particular example, the AFEC 2310 includes dimensions of 13.50 mm×13.78 mm, and the ADC 2320 includes dimensions of 16.88 mm×15.39. The AFEC 2310 is configured with power routing located in the middle to permit the supply of DC voltages on the left side of a 64-channel, and the symmetrical right side of the 64-channel. The ADC 2320 is configured so as to be partitioned into eight groups of 16-channel blocks, with each 16-channel block providing a 20 MHz word clock, and a 480 MHz bit clock. The 16-channel blocks are configured with individual banks of I-V references and supply regulations, and are configured for similar voltages to be connected externally through split planes in the ball grid array (BGA) substrate. The 16-channel blocks are configured for individual SPI control, thereby enabling partial or complete channel power down.

According to an embodiment, the pulser 2311 of the AFEC 2310 is configured to generate voltages of 76.8 $V_{pp}$ and 75.4 $V_{pp}$ based on all channels operating simultaneously. The pulser 2311 of the AFEC 2310 is configured to provide 15 and 13 ns falling and rising times, respectively, during 128-channel full operation.

The number and arrangement of components shown in FIGS. 23-26 are provided as an example. In practice, the devices shown in FIGS. 23-26 may include additional components, fewer components, different components, or differently arranged components than those shown in FIGS. 23-26. Additionally, or alternatively, a set of components (e.g., one or more components) of the devices shown in FIGS. 23-26 may perform one or more functions described as being performed by another set of components of the devices shown in FIGS. 23-26.

Figure 27:
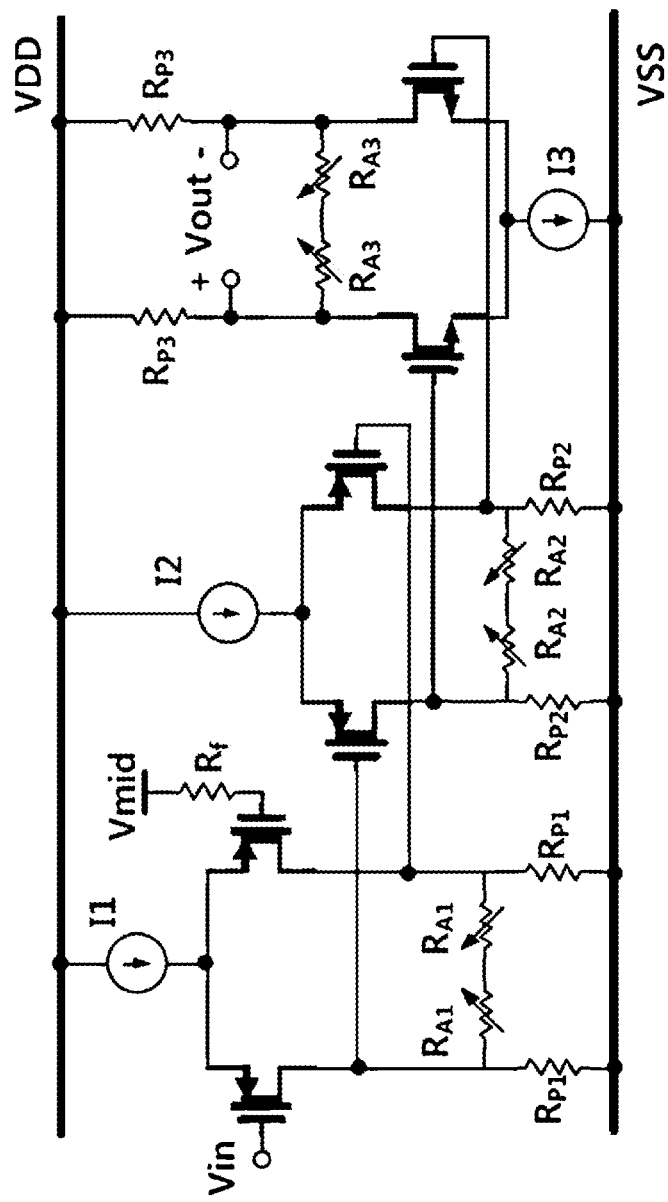
FIG. 27 is a diagram of a time gain compensation receiver according to an embodiment of the disclosure.

FIG. 27 is a diagram of a time gain compensation receiver according to an embodiment of the disclosure. FIG. 27 shows a schematic of the designed TGC, which has single input and differential outputs. The 3-stage TGC has active loads ($R_{A1\sim3}$) at each stage in order to control voltage gain of the amplifier by using a pair of MOS transistors. Gain of the TGC can be changed by control of active MOS on-resistance. The first two stages in the TGC are designed with a PMOS common source topology to realize low 1/f noise performance. The main transistor size in the first stage is also optimized for trade-off between noise figure and total size of the TGC. The designed TGC exhibited more than 55 dB of gain range and more than 40 dBc of harmonic-distortion-limit properties while maintaining 350 $mV_{pp}$ of output voltage swing.

Figure 28:
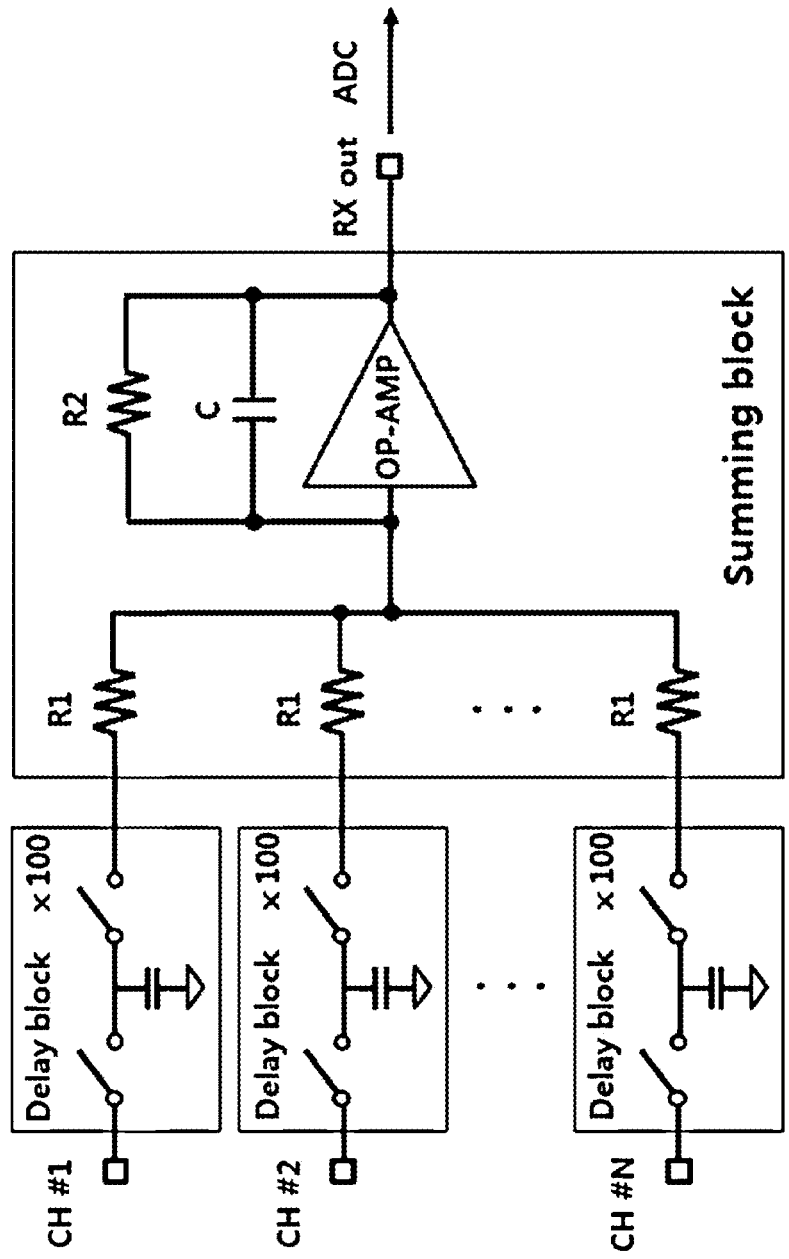
FIG. 28 is a diagram of an analog delay and voltage summing block according to an embodiment of the disclosure.

In the receiver chain, a beamformer is used to align the phase of signals received from various transducer elements by delaying and summing output signals of the receiver circuit. The beamformer can be implemented in either analog or digital topologies. The digital beamformer is robust against noise, and, in some cases, includes an external ADC at each channel. In order to minimize system composition and power consumption, an analog beamformer using switched-capacitor topology is used in some embodiments. A delay resolution can be selected to be 12.5 ns (80 MHz) or 25 ns (40 MHz), so, the maximum delay range is 1.25 us or 2.5 us, respectively. The delay block includes 100 delay lines, which are composed of sample-and-hold stages with a digital controller. Instead of adopting an MOS capacitor, a metal-insulator-metal (MIM) capacitor is used in some embodiments to avoid capacitor non-linearity, which may cause signal distortion in this structure. Signal summation can be coherently realized by controlling write and read clocks of the delay block. After passing through pipelined delay blocks, an operational amplifier integrates receiving signals for N-channels as shown in FIG. 28. Consequently, signal gain of the summing block can increased as calculated from 20·log(N), compared to that of a single channel.

Figure 29:
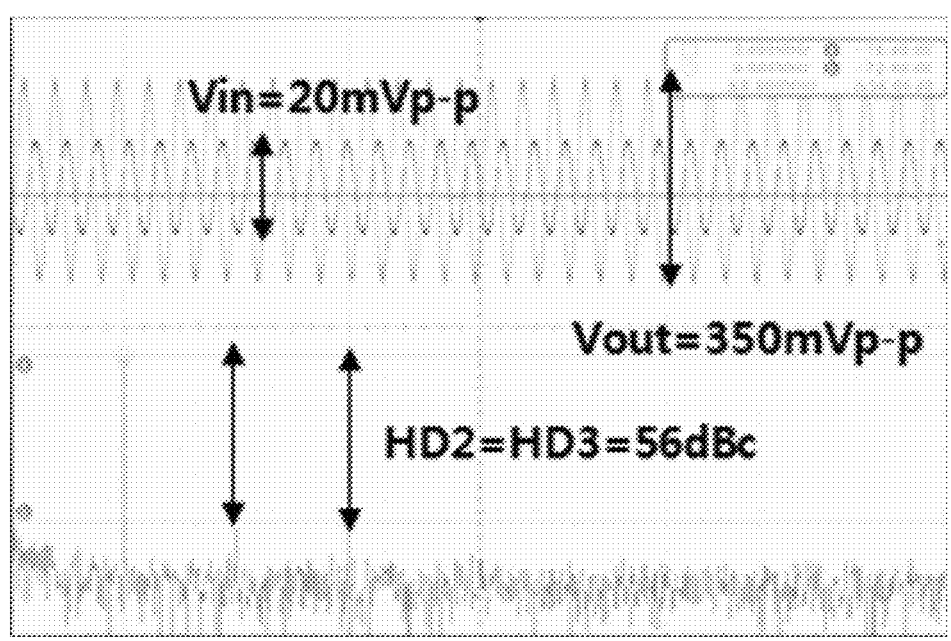
FIG. 29 is a diagram of example results of measured harmonic performances of a time gain compensation receiver according to an embodiment of the disclosure.
Figure 30:
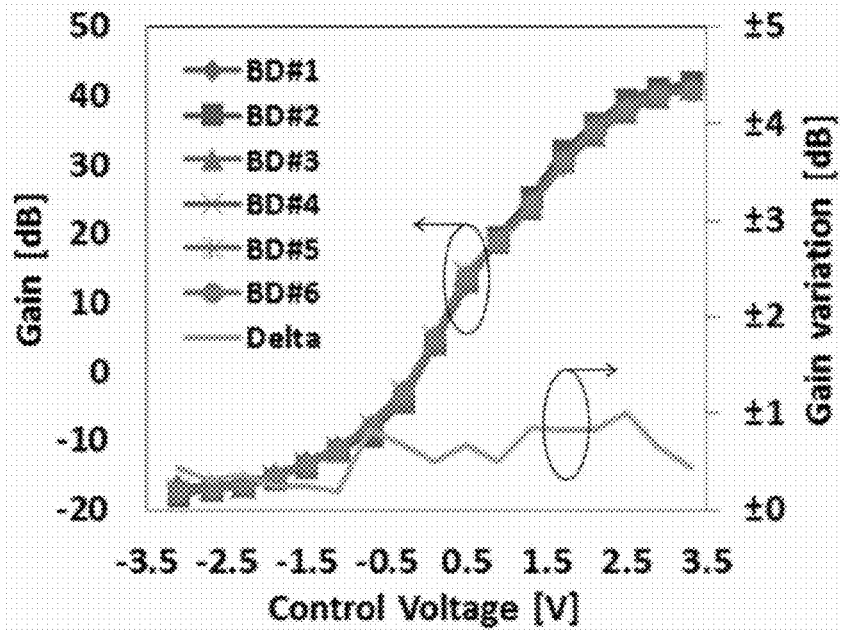
FIG. 30 is a diagram of example results of measured gain and gain variation ranges of a time gain compensation receiver according to an embodiment of the disclosure.
Figure 31:
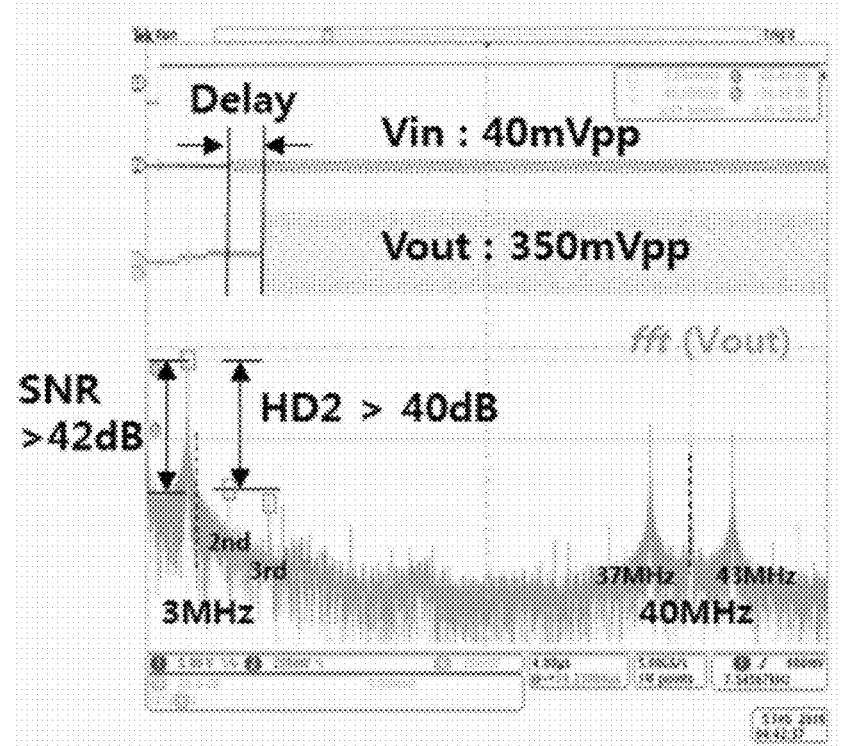
FIG. 31 is a diagram of example results of a measured output signal of a time gain compensation receiver in time and frequency domains according to an embodiment of the disclosure.

The proposed receiver is fabricated using a 0.35 μm CMOS process. FIG. 29 shows a measured output signal and harmonic performances of the proposed TGC. As shown in FIG. 29, second and third harmonic distortion against fundamental signals (HD2, HD3) equaled 56 dBc for a 350 $mV_{pp}$ output signal. FIG. 30 depicts example results of gain and gain variation ranges for 6 test boards. The gain range of 6 boards depicts more than 55 dB by changing on-resistance of active loads in the TGC with a control voltage range from −3.3 V to +3.3 V. Also, gain variation range is less than ±1 dB for the 6 test boards. FIG. 31 depicts a measured output signal of the receiver with a 200 ohm load in the time and frequency domains. For second and third harmonics, linearity shows more than 40 dBc at a middle level gain of 19 dB with more than 42 dBc of SNR. Mixed signals between 3 MHz received signal and 40 MHz delay clock appeared at 37 MHz and 43 MHz, which can be eliminated by system filtering. In order to avoid crosstalk between analog blocks and digital clocks, some embodiments include another metal layer option in the CMOS process for ground-shield. Thus, in some embodiments, digital clock harmonics are perfectly isolated from the analog receiver signal path.

Figure 32:
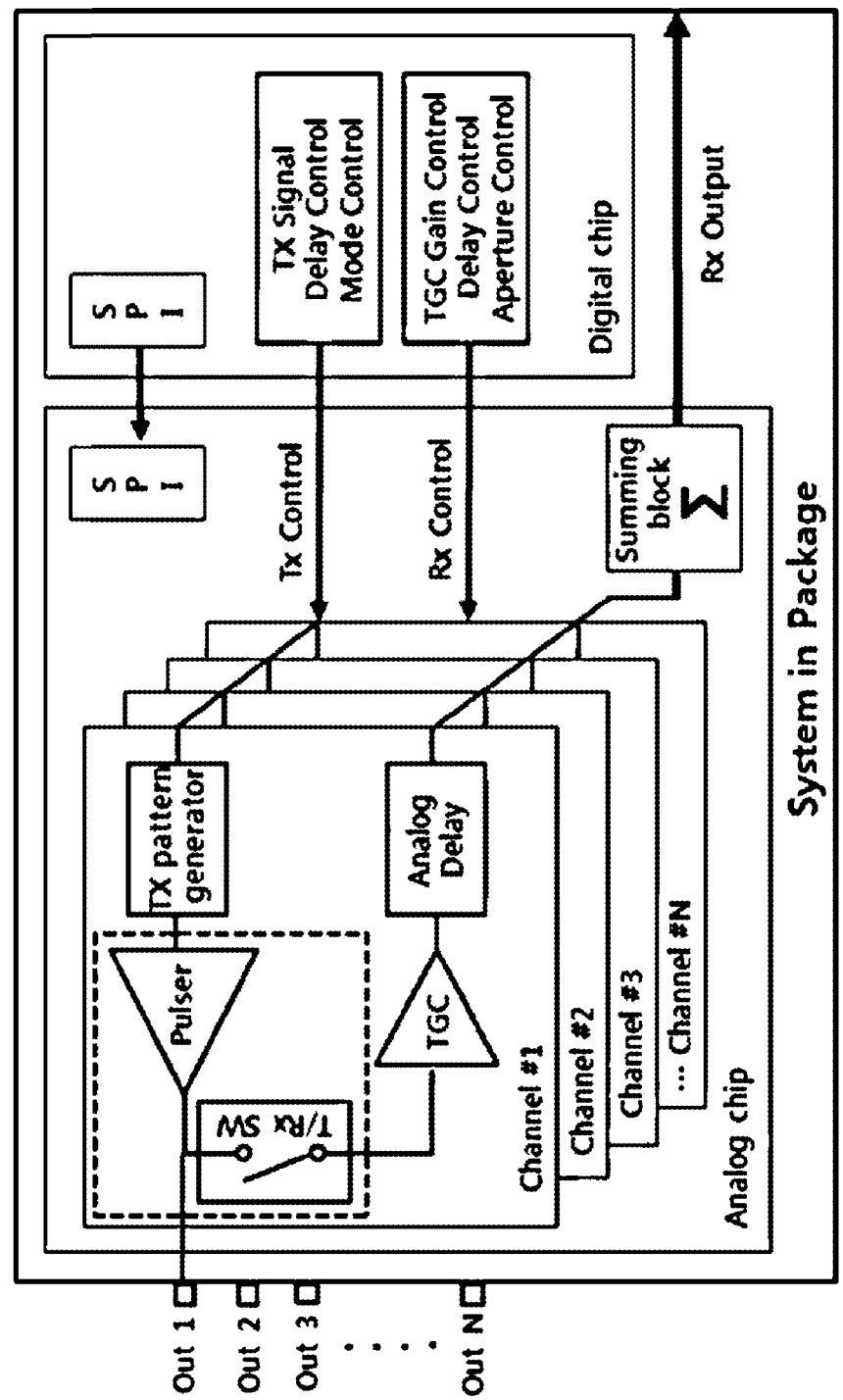
FIG. 32 is a diagram of an N-channel front end controller according to an embodiment of the disclosure.

FIG. 32 depicts a conceptual block diagram including analog and digital chips in a single system-in-package (SiP). The N-channel analog chip includes a Tx pattern generator, a pulser, a Tx/Rx switch, a time-gain-control (TGC), and an analog delay circuit in a single channel. The digital chip transmits a Tx digital signal to a Tx pattern generator in an analog chip. The Tx pattern generator converts a digital signal to an analog rectangular pulse. The pulser generates a high voltage output by amplifying a small signal of the Tx pattern generator. At each channel, a single analog pad is commonly used for Tx output and Rx input. A Tx/Rx switch is employed between the Tx and Rx chains to protect low voltage receiver circuits from high voltage signals of a pulser during Tx mode. Next, the received signal is transmitted to a TGC sample-and-hold analog delay circuit and is then summed by a summing block with a gain of 20·log(N).

Figure 33:
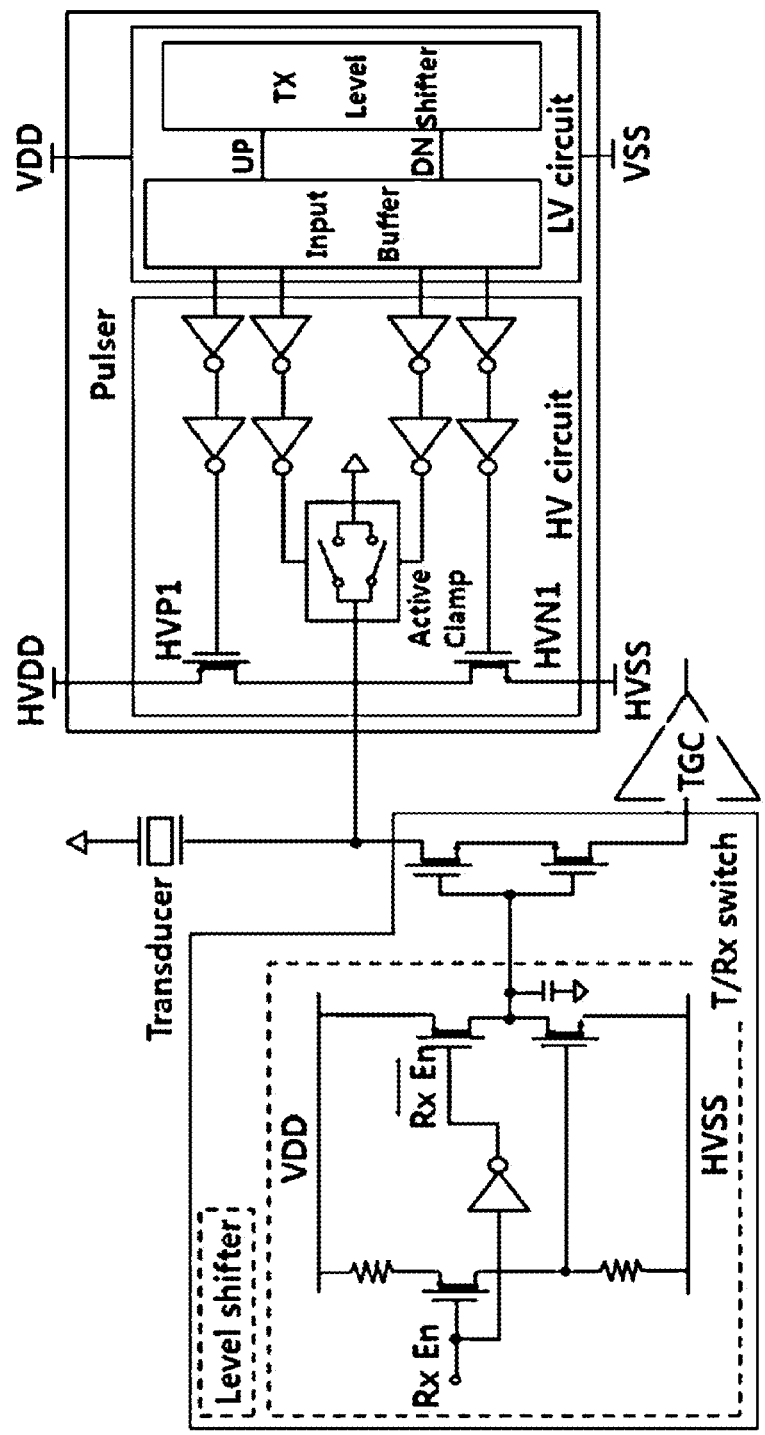
FIG. 33 is a diagram of a pulser according to an embodiment of the disclosure.

FIG. 33 depicts a block diagram of a pulser and Tx/Rx switch. The pulser includes a Tx level shifter, an input buffer, an active clamp switch, and high voltage output driver-stages. A Tx level shifter stage generates an analog signal, which is from a Tx pattern generator, that is sufficient to turn-on and turn-off the final high voltage MOS transistors. Active clamp switches are employed to avoid signal ring-down effect, which is from digital to analog signal conversion in the TX pattern generator and affects overall image quality. The final stage transistors of HVP1 and HVN1 generate high voltage rectangular signals by feeding high DC voltages of HVDD (+40 V) and HVSS (−40 V). To strike a balance between positive and negative sides of pulses in case of temperature and supply voltage variations, HVP1 and HVN1 are configured to have a same turn-on resistance.

The pulser is configured considering harmonic performances, such as second harmonic distortion (HD2) and harmonic distortion by pulse cancellation to support not only B-mode but also CW and Doppler mode imaging. The original pulse (A, 0°), inverse pulse (B, 180°), and cancelled-out pulse (A+B) were simulated in the time domain, and transformed to the frequency domain. The difference between fft(A) and fft(A+B) can be a defined harmonic distortion by pulse cancellation (HDPC) and between fft(A) and second harmonic of fft(A+B) can be a defined second harmonic distortion by pulse cancellation (HDPC2), respectively. The simulated pulser displayed an HD2 of 43.7 dBc, an HDPC of 43.5 dBc, and an HDPC2 of 41.8 dBc at a 5 MHz fundamental frequency and a 10 MHz second harmonic frequency.

The Tx/Rx switch is turned-on during Rx-mode, and turned-off during Tx-mode. A level shifter is employed in order to turn-on and turn-off transistors of the Tx/Rx switch. The output voltage of the level shifter swings from HVSS (−40 V) to VDD (+5 V) with respect to an RX-enabling signal. To avoid a peaking signal at the moment of TX-to-RX mode switching, the output capacitor size in the level shifter is configured in consideration thereof. Also, turn-on resistance of the Tx/Rx switch is configured to be minimized in order to reduce thermal noise and recovery time during Tx-to-Rx or Rx-to-Tx transition. The Tx/Rx switch is configured to transmit the signal with low insertion loss during Rx-mode and block the unwanted high voltage signal with high isolation performance during Tx-mode. Simulated results of insertion loss and isolation performance were 0.6 dB and 50 dB, respectively.

Figure 34:
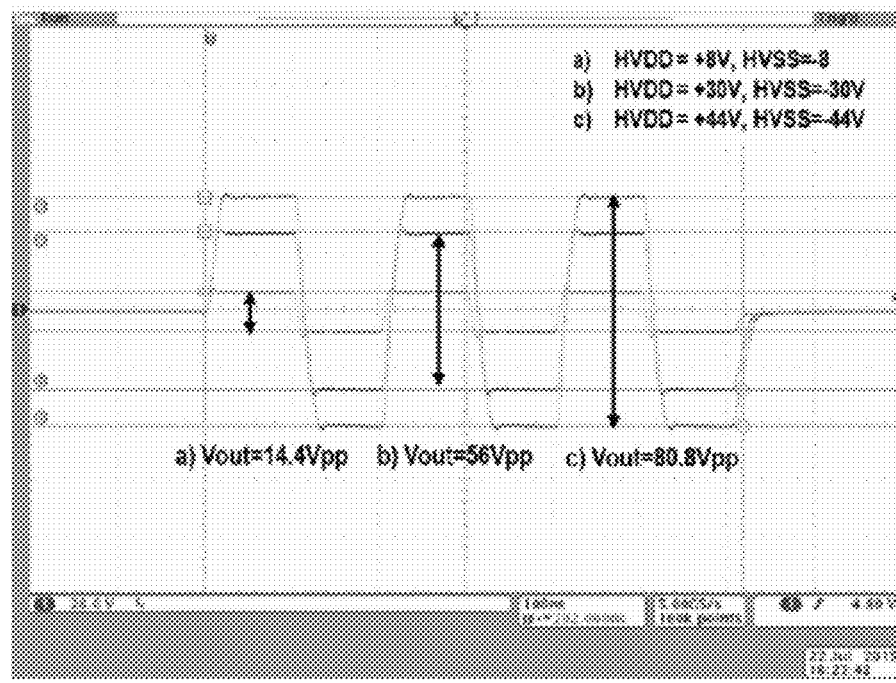
FIG. 34 is a diagram of example results of measured output voltages of a pulser according to an embodiment of the present disclosure.
Figure 35:
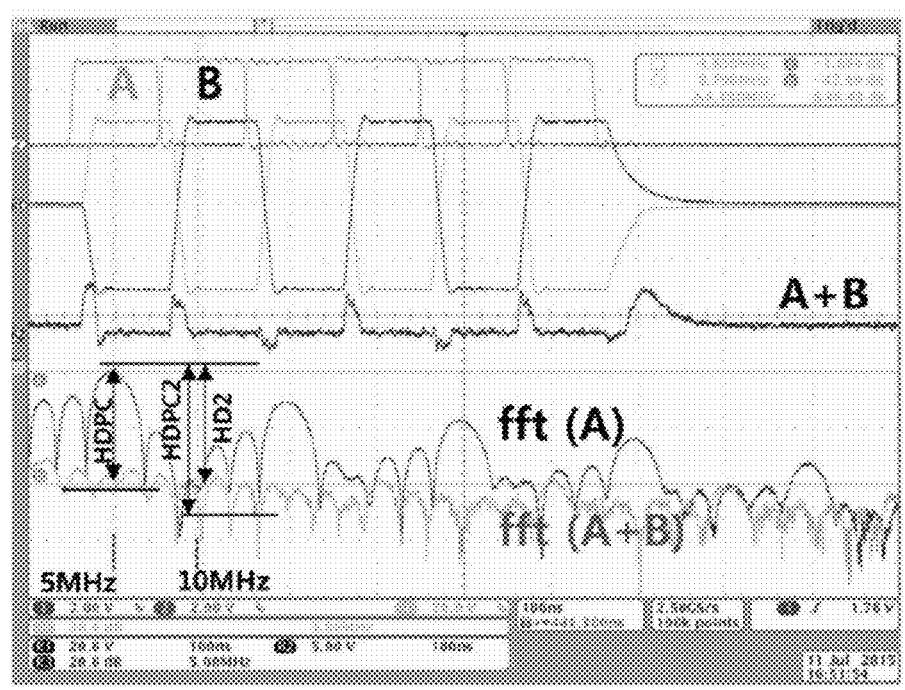
FIG. 35 is a diagram of example results of measured harmonic performance of a pulser according to an embodiment of the disclosure.
Figure 36:
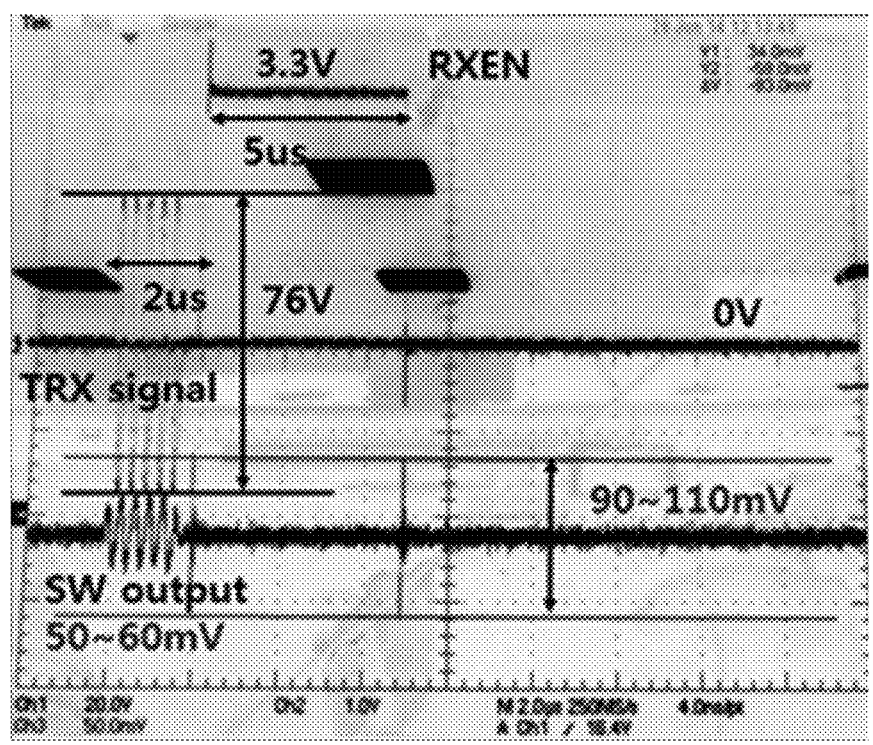
FIG. 36 is a diagram of measured isolation results of a T/Rx switch according to an embodiment of the disclosure.

The proposed pulser and Tx/Rx switch were fabricated using a 0.35 μm CMOS process with a high voltage option, which has a high voltage transistor with a maximum drain to source voltage of 100 V and a maximum gate to source voltage of 18 V. As shown in FIG. 34, the pulser generates a variable output pulse of 14.4~80.8 $V_{pp}$ by feeding a DC supply voltage of ±8~±44 V. FIG. 35 depicts harmonic imaging performance of the pulser. The measured results depict an HD2 of 41 dBc, an HDPC of 45 dBc, and an HDPC2 of 40.4 dBc, respectively. FIG. 36 depicts isolation performance of the Tx/Rx switch. Output voltage was limited to 60 $mV_{pp}$ against a 76 $V_{pp}$ pulser signal with 62 dB of isolation performance. The voltage peaking was also limited to 110 $mV_{pp}$ for Tx-to-Rx mode switching.

Figure 37:
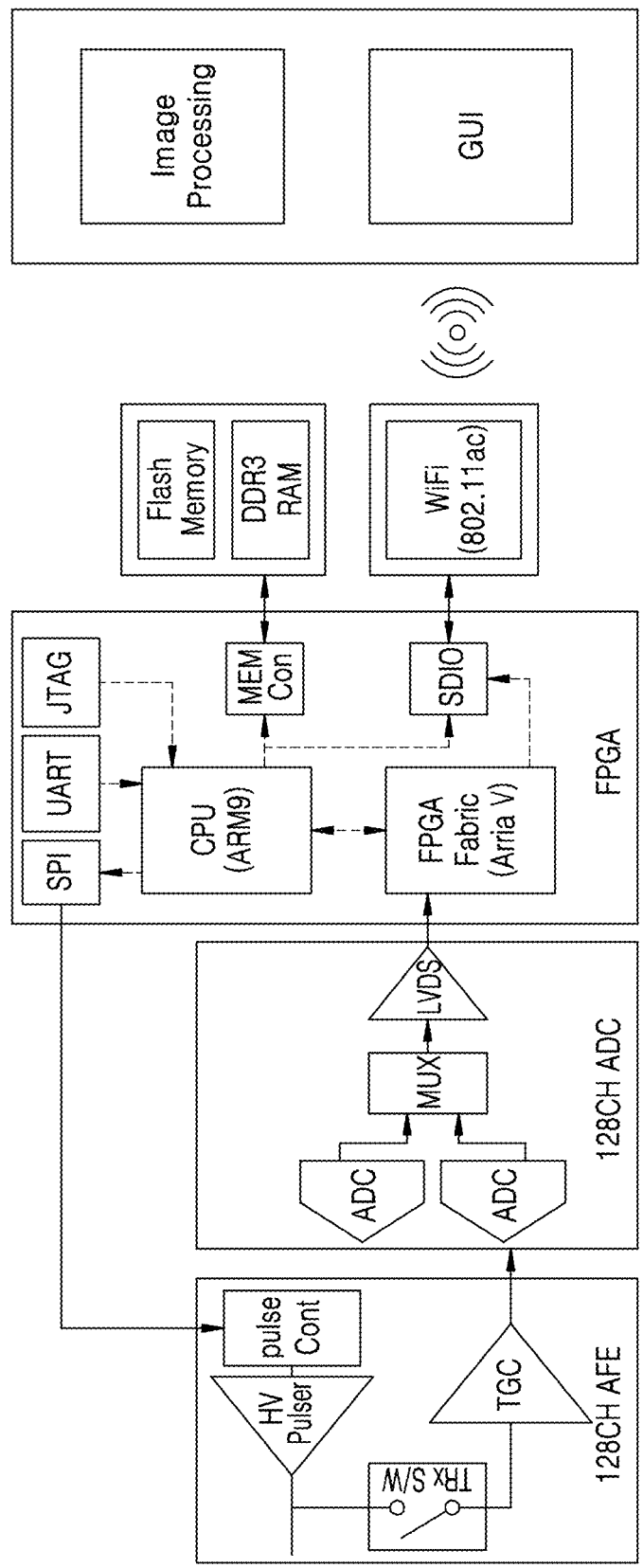
FIG. 37 is a diagram of a system architecture and a handheld wireless ultrasound imaging system according to an embodiment of the disclosure.

The proposed system architecture according to an embodiment is divided into three parts: AFE, ADC, and FPGA chips. As shown in FIG. 37, all the foregoing parts are integrated on the same PCB board. The AFE is architected to have a pulse control unit, an HV pulser, a Tx/Rx switch and a TGC. The HV pulser utilizes commercially HV CMOS processes offering higher supply voltages. In the mixed signal part, an ADC is implemented in a lower voltage technology and process node. A lower process node, 0.13 μm, allows reduced dynamic power consumption for digital blocks such as decimation filters, serializers, control and switching circuits as they significantly add up power consumption due to parallelization of 128 channels. Also, back-end processing such as a line buffer for extended aperture, a black-hole filling/noise spike filter, persistence, and sine logic are implemented in the FPGA that is in communication with flash memory and DDR3 RAM. To perform various diagnosis modes, the system is configured to be replaceable with an FPGA and memory of larger capacity without modifying any circuit. Additionally, a wireless communication module (e.g., a WiFi combo module) is employed for data transmission to a mobile phone or a tablet PC using the 802.11ac protocol.

Figure 38:
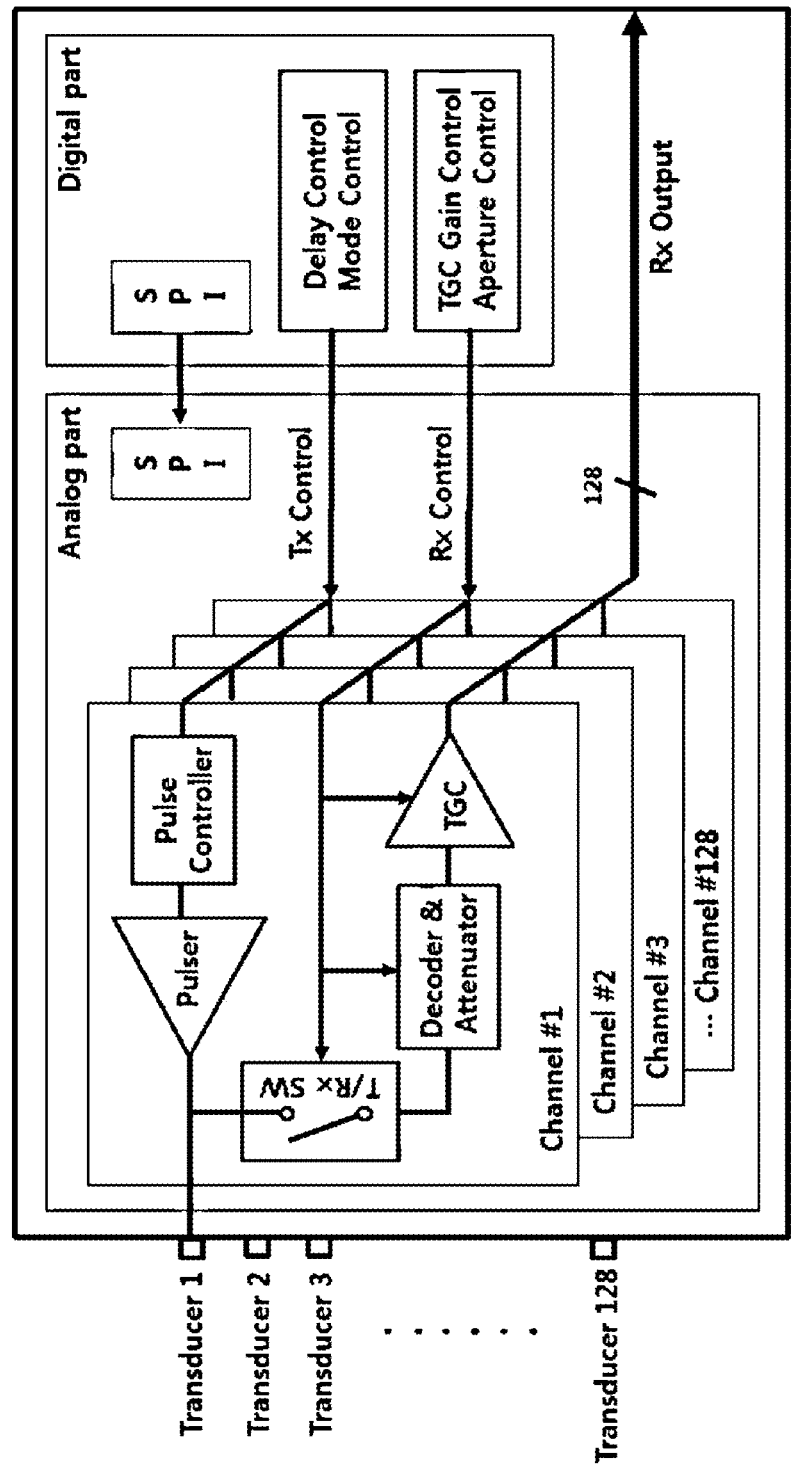
FIG. 38 is a diagram of a 128-channel AFE chipset according to an embodiment of the disclosure.

FIG. 38 depicts a block diagram of a 128-channel AFE chipset. The transmitter of the proposed AFE includes an HV pulser, and a Tx/Rx switch. The HV pulser comprises a Tx level shifter, an input buffer, an active clamp switch, and high voltage output driver stages. The Tx level shifter stage amplifies an analog signal, which is from the Tx pattern generator, to permit turn-on and turn-off of the HVMOS transistors in the final stage. Active clamp switches are employed to avoid signal ring-down effect, which is from digital-to-analog signal conversion in the TX pattern generator and affects overall image quality. The final stage transistors of the HV PMOS and NMOS generate an HV rectangular signal by feeding high DC voltages of +40 V and −40 V. To strike a balance between positive and negative sides of the pulse in case of temperature and supply voltage variations, two transistors are configured to have same turn-on resistances.

The Tx/Rx switch is turned-on during Rx-mode, and is turned-off during Tx-mode. A level shifter is employed in order to turn-on and turn-off transistors of the Tx/Rx switch. An output voltage of the level shifter swings with respect to an Rx-enabling signal from −40 V to +5 V. To avoid a peaking signal at the moment of Tx-to-Rx mode switching, an output capacitor size in the level shifter is configured in consideration thereof. Also, a turn-on resistance of the Tx/Rx switch is configured to be as low as possible in order to reduce thermal noise and recovery time during Tx-to-Rx or Rx-to-Tx transition. The Tx/Rx switch is configured to transmit the signal with low insertion loss during Rx-mode, and block the unwanted high voltage signal with high isolation performance during Tx-mode.

The TGC is combined with an analog decoder and an attenuator. The analog decoder receives 5 digital signals from the FPGA and converts them into 32 on and off signals for the attenuator. The attenuator controls a gain range of the TGC with a discrete gain step of 1.5 dB. An automated TGC gain control algorithm uses an internal timer combined with a serial peripheral interface (SPI) to receive control data from the FPGA. The 3-stage TGC has active loads at each stage in order to control gain of the amplifier by using a pair of MOS transistors. Gain of the TGC can be changed by controlling an on-resistance of the active MOS transistor. The first two stages in the TGC are designed with a PMOS common source topology to realize low 1/f noise performance. The main transistor size in the first stage is also optimized for trade-off between a noise figure and a total size of the TGC. The designed TGC depicts more than 45 dB of gain range and more than 40 dBc of harmonic-distortion-limit properties (HD2, HD3 for second and third harmonics) with 3.7 mA of current consumption while maintaining 350 $mV_{pp}$ of output voltage swing.

Figure 39:
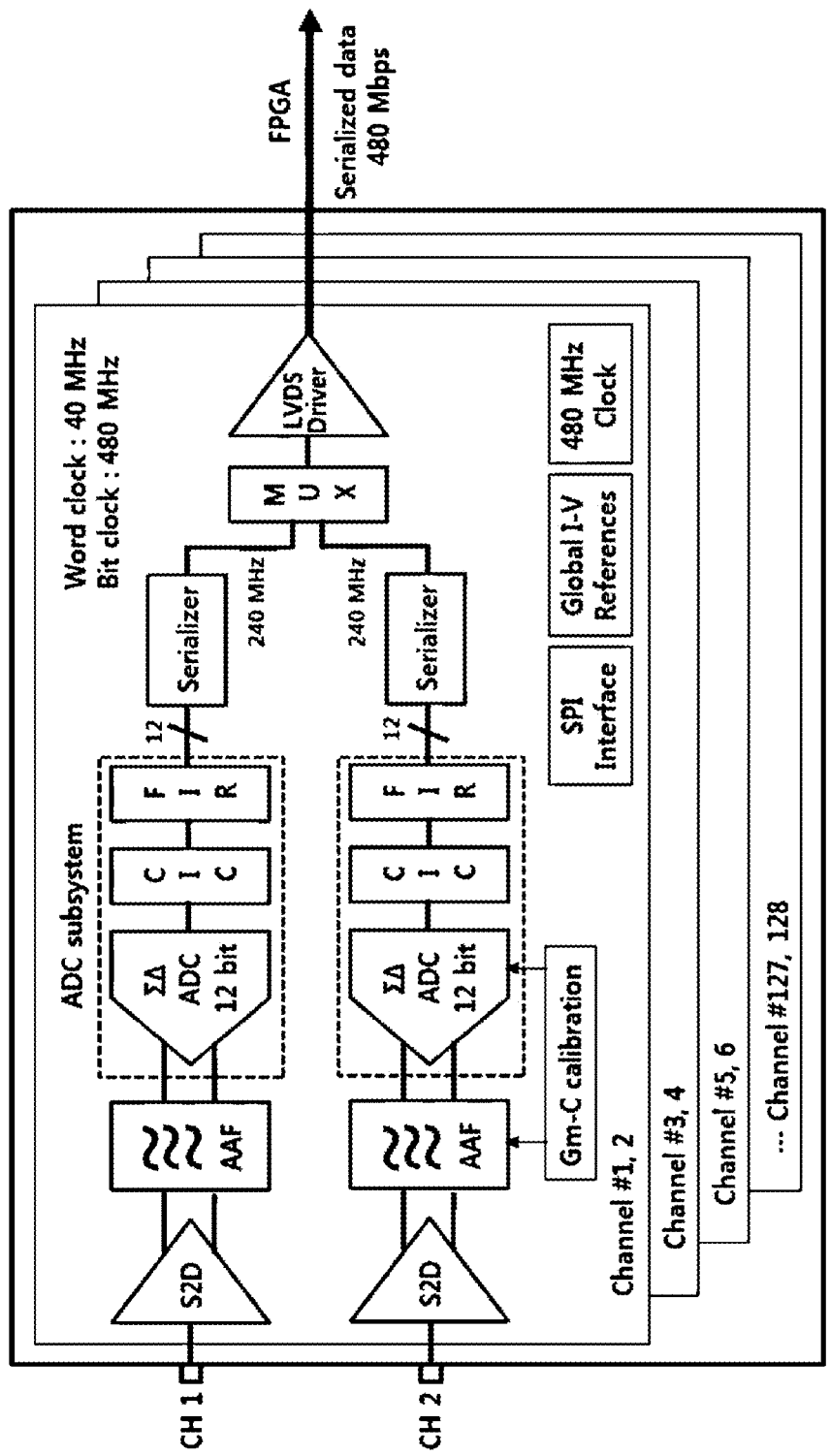
FIG. 39 is a diagram of a 128-channel ADC chipset according to an embodiment of the disclosure.

FIG. 39 depicts a block diagram of the mixed signal ADC chipset for 2-channels. As shown in FIG. 39, a single-to-differential buffer is employed in the first stage of the ADC. The buffer is used to balance specification requirements of low power and low input referred noise. Source degeneration resistors are employed for distortion compensation. The buffer consumes 540 μA of current over a 3.3 V supply. The input referred noise is 8.4 nV√Hz over a 10 MHz input bandwidth for a maximum input of a 0.4 Vpp. The integrated noise is 26.5 $\mu V_{RMS}$.

A Gm-C filter topology is employed for the Anti-Aliasing filter (AAF) due to open loop stages with no op-amp and facility to drive capacitive loads for lower consumption. The filter is implemented as a $2^{nd}$ order fully differential biquad with Nauta transconductance elements. Nauta Gm blocks do not have internal nodes due to usage of inverters as gain elements resulting in parasitic poles shifting to a much higher frequency than the filter cut off. The architecture permits a roughly constant Gm, which supports a process sensitive Gm-C filter topology. The transfer function of the biquad shown could be calculated as:

$$H(s) = \frac{\frac{g_{m1}g_{m3}}{C_1 C_2}}{s^2 + \frac{g_{m2}}{C_1}s + \frac{g_{m3}g_{m4}}{C_1 C_2}}$$

The above equation implies a DC gain of $$H(0) = \frac{g_{m1}}{g_{m4}}.$$

For a constant-$g_m$ case, $g_{m1}=g_{m4}=g_m$, and therefore DC gain is set to 0 dB. The filter is configured for a maximum corner frequency of 10 MHz to ensure that the Nyquist limit is not exceeded. The filter consumed 1 mA of current over a 1.5 V supply while the input referred noise was kept under 24 nV/√Hz.

The continuous time delta-sigma of the ADC presented several design considerations including the selection of an oversampling ratio, and a modulator filter topology. For a 10 MHz band limited signal, an oversampling rate of 24 permits the fitting of the multiplexed output data within the maximum link rate of a low voltage differential signaling (LVDS) channel. The modulator includes a local feedback, 2 main feedbacks, and 3 feedforward paths to boost the phase response by inserting additional zeroes. The modulator filter was implemented as a $3^{rd}$ order gm-C filter using a Nauta transconductor as a unit element due to lack of op-amps, high unity gain and lower power operation. DC gain is maximized by cancelling out the output impedance through negative resistance. The excess loop delay and closed loop feedback stability issues are addressed by the 3 feedforward loops of the architecture while metastability is addressed by having two stages of comparator latches inside the quantizer. A 4-bit quantizer adopting the minimal latency flash architecture and having 15 comparators is employed. Since clock jitter would cause the DAC to raise an in-band noise floor, a 4-bit current steering DAC is employed to reduce the noise energy per cycle and desensitize the circuit to clock jitter.

The decimation filter is implemented as a cascaded integrated comb (CIC) filter as this embodiment does not require any multipliers. To provide a sharper cutoff, a finite impulse response (FIR) filter is used in conjunction with the CIC. A parallel-to-serial interface is implemented to take the 12 bits output from the FIR at 20 MHz. The serial output interface runs a 480 MHz per channel. Two channels are muxed in order to decrease the overall number of I/O pins. Serial data is transmitted in each clock edge which provides a 960 Mb/s data rate at the output. An LVDS output interface is implemented to drive the interconnection from the ADC IC. A near 350 mV swing signal is transmitted to the receiver end with a 100 ohm differential termination.

The digital signal processing block in the FPGA contains two main parts of the mid-end beamformer and the back-end processing. The mid-end portion is responsible for the delay of signals in different channels to align the signals before the summing operation. The summed signal is fed into the back-end where the signal is demodulated. Following envelope detection, the back-end calculates the amplitude of the signals. There is also a control block that generates control signals by using locally pre-computed data. Due to the limitation of space, a local memory is updated by each scanline. All delay information is saved in external memory. The mid-end contains 128 paths and the amount of delays for each are dynamically set by the control signals from the control block. The signals are delayed by two units, a bulk delay and a fractional delay, sequentially. In addition to the delay, each path has an apodization weight. The bulk delay part delays the signal by an integer number of a sampling period while the fractional delay is a polyphase filter, which provides the interpolated data without up-sampling. The apodization coefficients are multipliers used to assign the signals different weights in different channels. The amount of data log-compression in the FPGA is also an important parameter for a decision of the wireless data transfer method. As an example, the required data rate of output in log-compression is 16×1024×128×30=63 Mbps, wherein 16 is the data bit-width, 1024 is the number of samples per scan lines, 128 is the number of scan lines per frame, and 30 is the frame rate, respectively.

Figure 40:
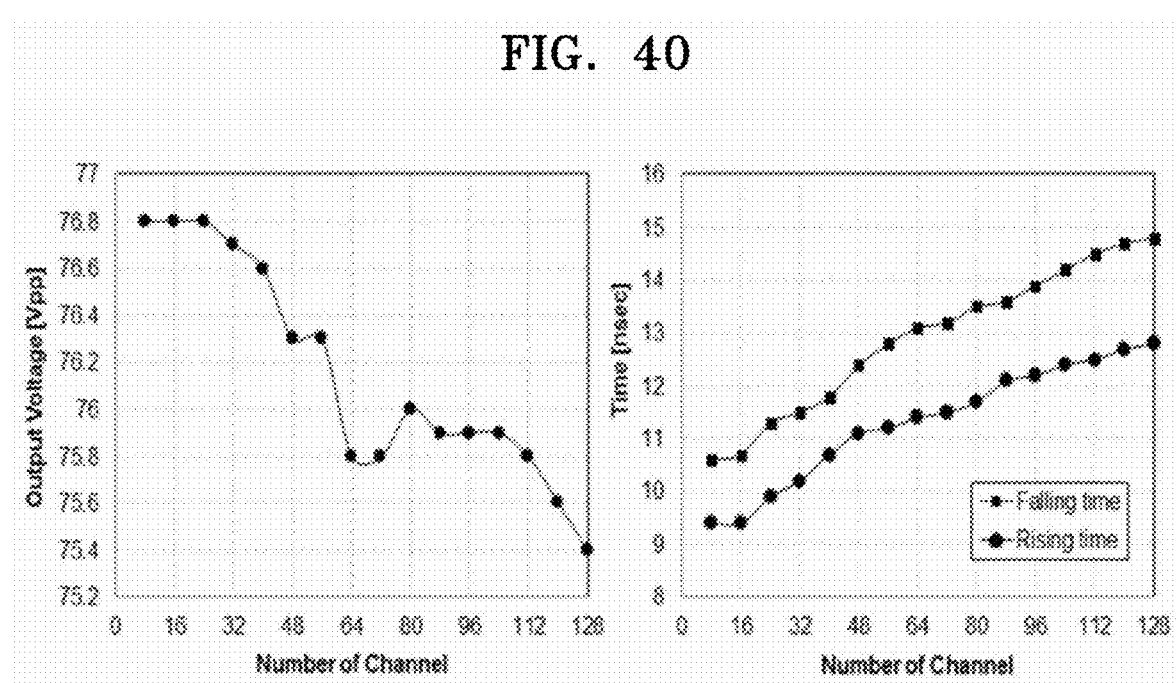
FIG. 40 is a diagram of test results showing an output voltage and rising/falling times of the pulser with respect to a number of channels according to an embodiment of the disclosure.
Figure 41:
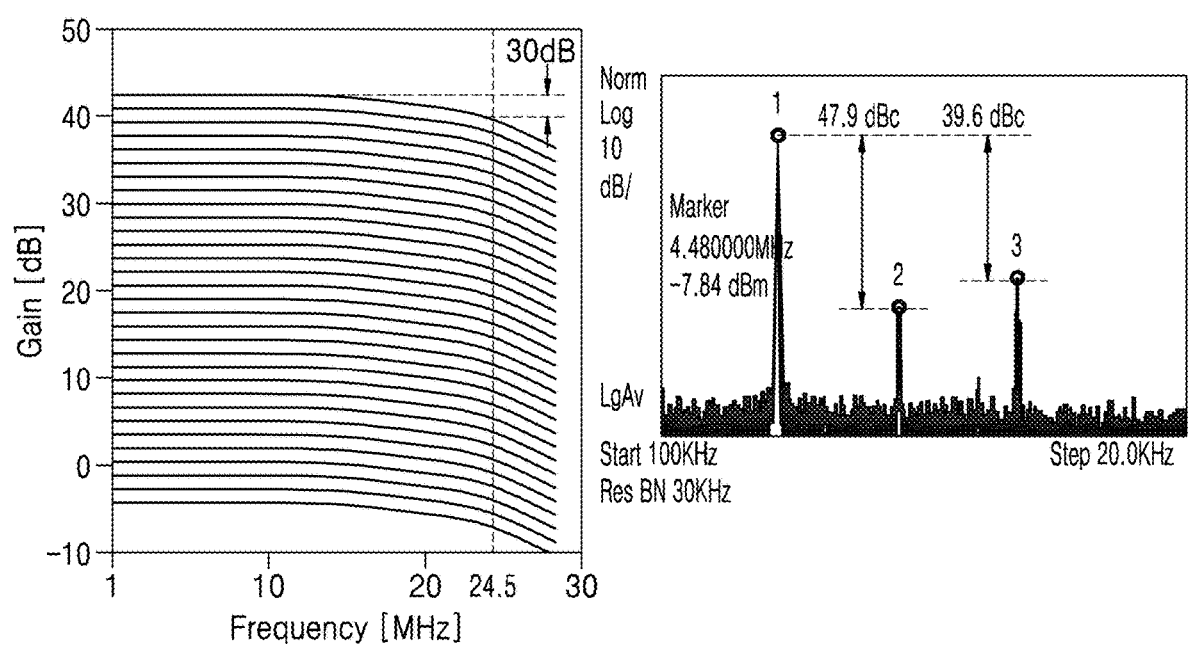
FIG. 41 is a diagram of test results showing a gain range and harmonic performance of the TGC according to an embodiment of the disclosure.
Figure 42:
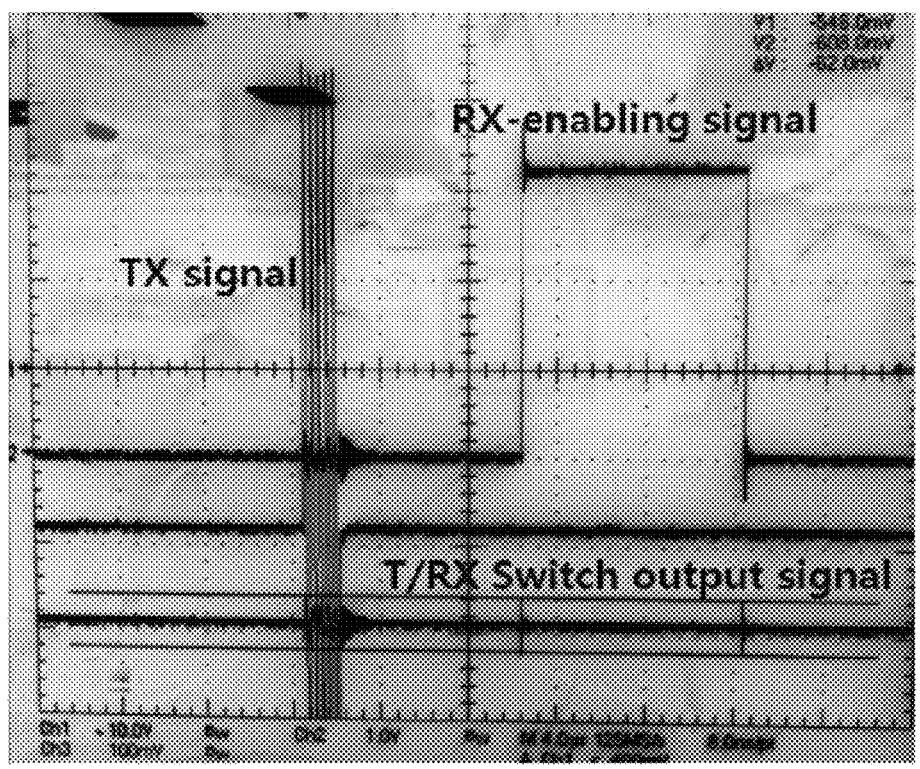
FIG. 42 is a diagram depicting measured isolation performance of the Tx/Rx switch according to an embodiment of the disclosure.
Figure 43:
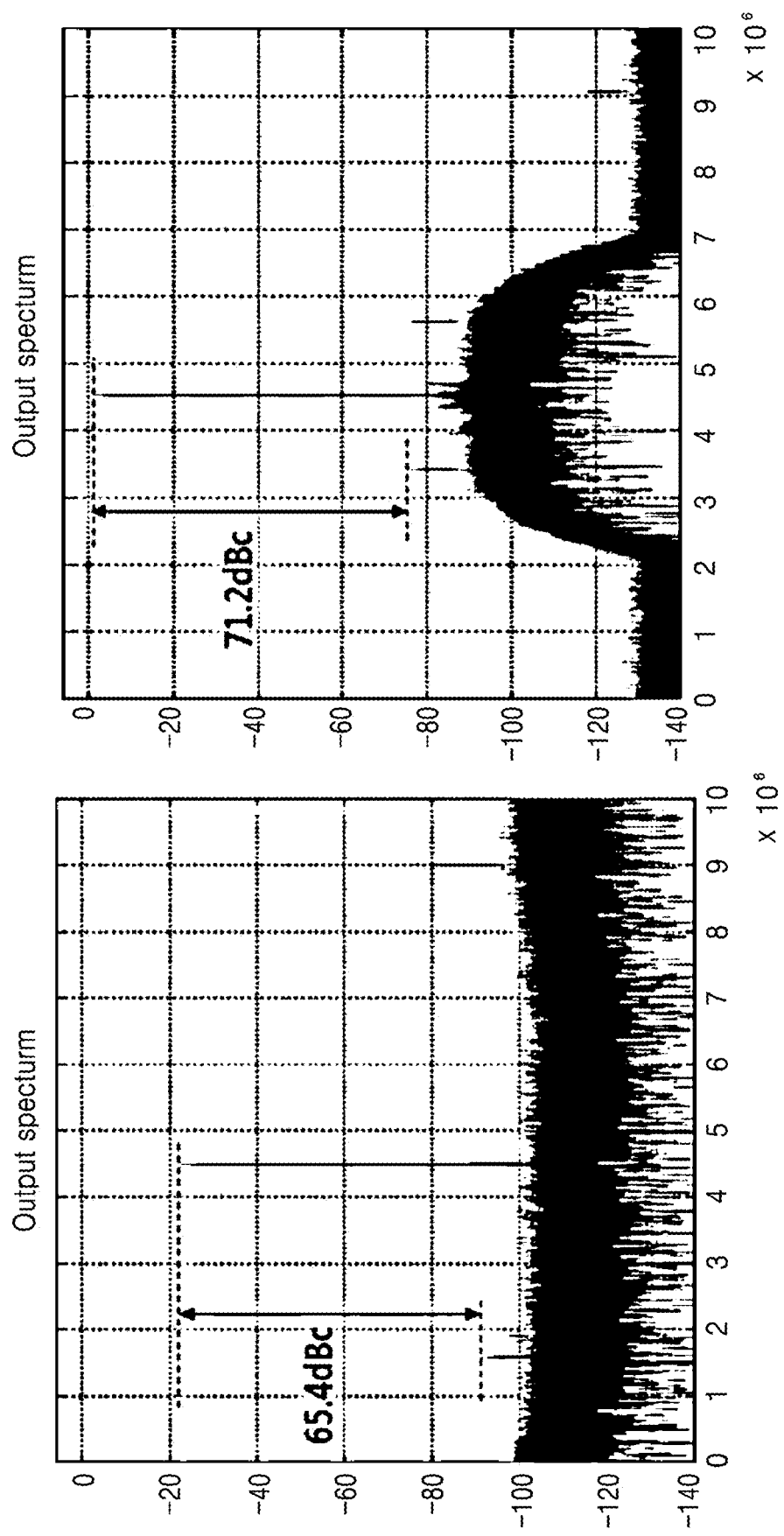
FIG. 43 is a diagram depicting a measured output FFT of the ADC at 4.5 MHz for a 50 mV input with and without BPF according to an embodiment of the disclosure.
Figure 44:
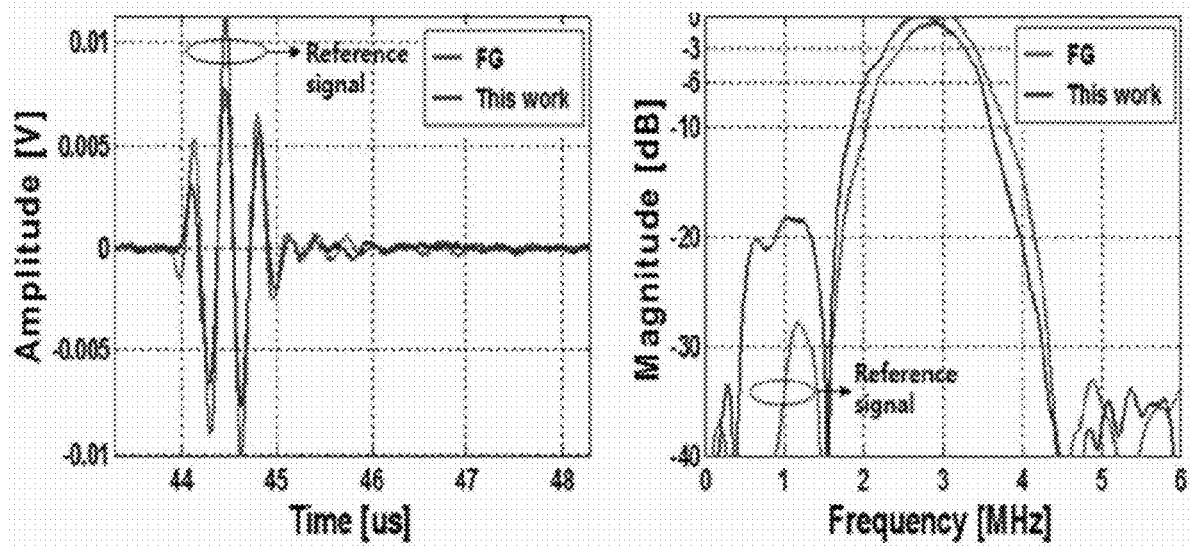
FIG. 44 is a diagram depicting acoustic and spectral output signals of the pulser according to an embodiment of the disclosure.

FIG. 40 depicts pulser performance in the AFE chipset. The pulser generates a maximum voltage of 76.8 $V_{pp}$, and a reduced voltage of 75.4 $V_{pp}$ when all channels operate simultaneously. Falling and rising times of the pulse were also measured with respect to the number of channels. The pulser shows a maximum of 15 and 13 ns of falling and rising times for 128-channel full operation. For receiver measurement, a gain range is 47 dB from −5 dB to +42 dB with 1.5 dB discrete gain steps. Also, HD2 and HD3 are 47.9 dBc and 39.6 dBc at a maximum gain of +42 dB, respectively, as shown in FIG. 41. FIG. 42 depicts isolation performance of the Tx/Rx switch. Output voltage is limited to 50 mV against a 76.8 $V_{pp}$ pulser signal with 64 dB of isolation performance. The voltage peaking is also limited to 62 mV for Tx-to-Rx mode switching signal. The ADC output spectrum is displayed in FIG. 43. The plot on the left shows the FFT for a 4.5 MHz input under normal conditions without any optimization. The measured SNR was roughly 65.4 dB at an ENOB of 10.57 bits. In order to enhance the spurious free dynamic range (SFDR), a simple digital bandpass filter centered around 4.5 MHZ was applied to filter out the spurious harmonic. The result of applying the filter is shown in FIG. 44 on the right that enhanced SNR close to 71.2 dB at an ENOB of 11.53 bits by filtering out the 9 MHz harmonic.

Figure 45:
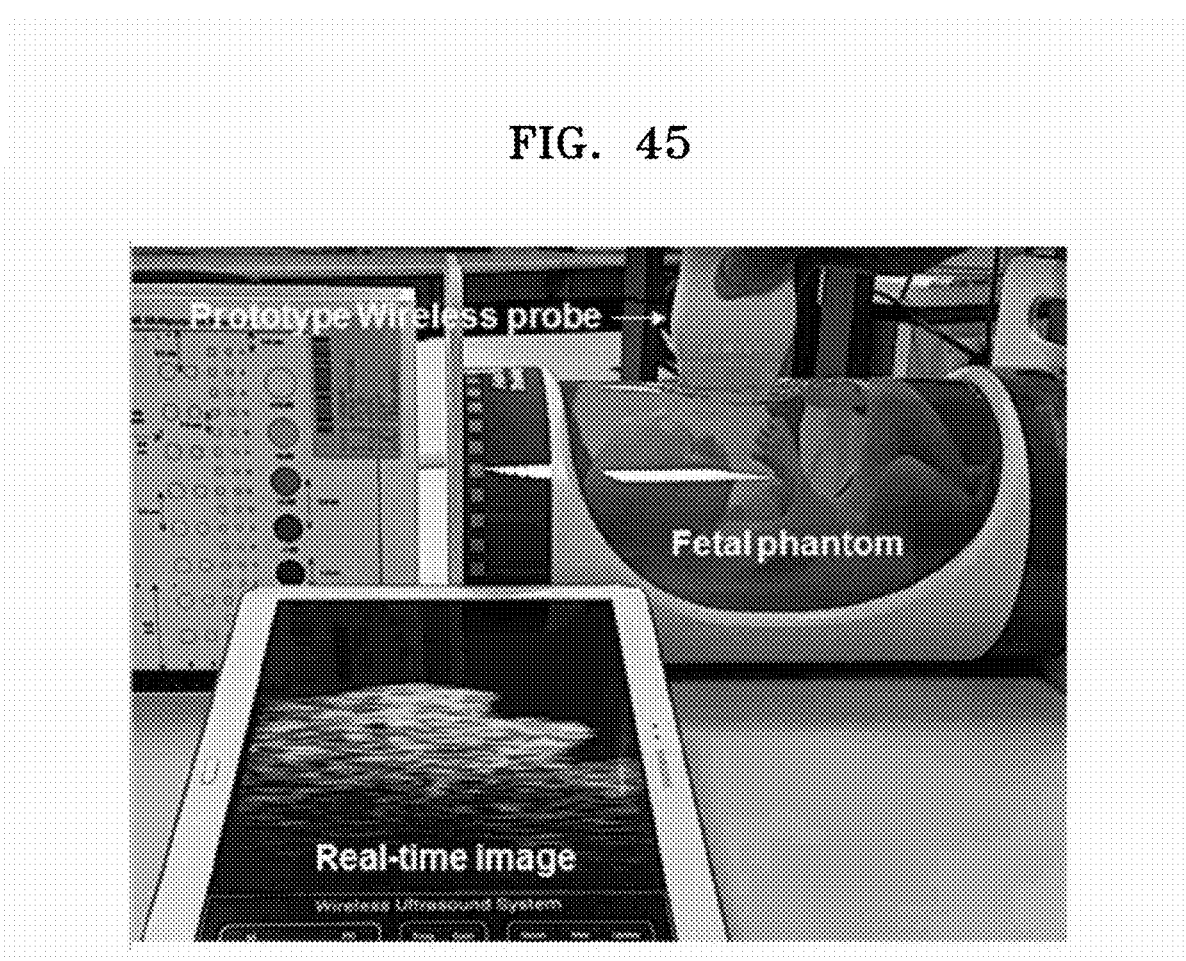
FIG. 45 is a diagram depicting real-time B-mode imaging of the 128-channel wireless probe on a fetal phantom according to an embodiment of the disclosure.

In a test measurement, the Tx acoustic signal was measured with a hydrophone, which was placed 4.5 mm above from transducer surface. A phased array piezoelectric transducer was used to obtain the acoustic signal output from a 2-cycled 76.8 $V_{pp}$ pulse at 2.9 MHz. Acoustic and spectral signals of the pulser are shown in FIG. 44. The blue line is a reference signal when an input signal is generated by a function generator, and the green line is a real signal from the pulser. The two signals are similar in the acoustic and spectral domains. The AFE and ADC chipsets were employed in a wireless ultrasound probe that was successfully demonstrated to yield a real-time B-mode ultrasound image of a fetal phantom as shown in FIG. 45 at 3 MHz operating frequency. The per-channel power consumption was 10 mW for the AFE chip and 25 mW for the ADC chip, respectively.

Some implementations herein provide a 128-channel wireless ultrasound handheld ultrasound system. The device is integrated with 128-channel AFE, ADC, and FPGA chipsets, and a wireless module for full digital beamforming, high SNR, and wireless data communication. According to test results, the AFE chipset provides a 76.8 $V_{pp}$ pulse and 47 dB of gain range with nearly 1.5 dB of discrete gain step. The delta-sigma ADC including drivers and anti-aliasing filters performs SNDR of 67 dB at an ENOB of 10.57 bits. The probe provides real-time B-mode images to a tablet PC which is equipped with image optimization algorithms and a graphic user interface (GUI), and supports B-, CW- and Doppler modes.

According to the disclosure, general users may easily manipulate ultrasound diagnosis apparatuses and easily ascertain a reference location from which an optimal ultrasound image of a predetermined body part may be acquired, thereby acquiring an ultrasound image. Thus, the ultrasound diagnosis apparatus may have increased accuracy and may more rapidly acquire an ultrasound image.

A method according to an embodiment of the disclosure may be embodied as program commands executable by various computer means and may be recorded on a non-transitory computer-readable recording medium. The computer-readable recording medium may include program commands, data files, data structures, and the like separately or in combinations. The program commands to be recorded on the computer-readable recording medium may be specially designed and configured for embodiments of the disclosure or may be well-known to and be usable by one of ordinary skill in the art of computer software. Examples of the non-transitory computer-readable recording medium include a magnetic medium such as a hard disk, a floppy disk, or a magnetic tape, an optical medium such as a compact disk-read-only memory (CD-ROM) or a digital versatile disk (DVD), a magneto-optical medium such as a floptical disk, and a hardware device specially configured to store and execute program commands such as a ROM, a random-access memory (RAM), or a flash memory. Examples of the program commands are advanced language codes that can be executed by a computer by using an interpreter or the like as well as machine language codes made by a compiler.

The embodiments should be considered in a descriptive sense only and not for purposes of limitation. Descriptions of features or aspects within each embodiment should typically be considered as available for other similar features or aspects in other embodiments. While the disclosure has been particularly shown and described with reference to embodiments thereof, it will be understood by those of ordinary skill in the art that various changes in form and details may be made therein without departing from the spirit and scope of the disclosure as defined by the following claims.

What is claimed is:

1. An ultrasound diagnosis apparatus comprising:
a probe configured to acquire ultrasound data of an object;
an image generator configured to generate an ultrasound image of the object by using the ultrasound data;
a location tracking sensor configured to acquire a location of the probe on the object;
a display configured to display the location of the probe and a reference location on an image representing the object; and
a controller configured to determine whether the location of the probe corresponds to the reference location,
wherein when it is determined that the location of the probe does not correspond to the reference location, the controller is further configured to:
determine a movement path to be taken by the probe to move to the reference location, and
control the display to display the movement path from the location of the probe to the reference location on the image representing the object.

2. The ultrasound diagnosis apparatus of claim 1, further comprising a storage configured to map a plurality of locations of the probe with a plurality of reference ultrasound images and store a result of the mapping,
wherein the location tracking sensor is further configured to:
compare the ultrasound image with the plurality of reference ultrasound images,
select one from among the plurality of reference ultrasound images based on a result of the comparison, and
acquire a location corresponding to the selected reference ultrasound image as the location of the probe.

3. The ultrasound diagnosis apparatus of claim 1, further comprising a photographing unit configured to photograph the probe and the object, wherein the location tracking sensor is further configured to detect an area corresponding to the probe and an area corresponding to the object from an image captured by photographing the probe and the object, and acquire the location of the probe based on a location of the area corresponding to the probe with respect to the area corresponding to the object.

4. The ultrasound diagnosis apparatus of claim 1, wherein, when the location of the probe corresponds to the reference location, the controller is further configured to control the display to display an image representing that the location of the probe corresponds to the reference location.

5. The ultrasound diagnosis apparatus of claim 1, wherein, when the location of the probe corresponds to the reference location, the controller is further configured to control the probe to transmit an ultrasound signal to the object and receive an echo signal from the object to acquire the ultrasound data.

6. The ultrasound diagnosis apparatus of claim 1, further comprising a communicator configured to transmit the ultrasound image to an external device when the location of the probe corresponds to the reference location.

7. The ultrasound diagnosis apparatus of claim 1, further comprising an input interface configured to receive a user input of selecting at least one location from among a plurality of locations on the object, wherein the controller is further configured to determine the selected location as the reference location.

8. The ultrasound diagnosis apparatus of claim 1, further comprising a communicator configured to receive, from an external device, information that is used to determine the reference location, wherein the controller is further configured to determine the reference location based on the received information.

9. The ultrasound diagnosis apparatus of claim 1, further comprising a communicator configured to transmit at least one selected from the location of the probe, the reference location, the ultrasound image, and an image displayed on the display to an external device.

10. The ultrasound diagnosis apparatus of claim 9, wherein the communicator receives information that is used to generate the ultrasound image, from the external device, and the controller is further configured to control at least one selected from the probe and the image generator, based on the received information.

11. The ultrasound diagnosis apparatus according to claim 1, wherein the probe comprises, an analog front-end controller, an analog-to-digital converter, a field-programmable gate array, and a communication module, and wherein the analog front-end controller comprises a pulser, a switch configured to switch between a transmit mode and a receive mode, and a time gain compensation receiver.

12. The ultrasound diagnosis apparatus according to claim 1, wherein the probe comprises, an analog front-end controller, an analog-to-digital converter, a field-programmable gate array, and a communication module, and wherein the analog-to-digital converter comprises a multiplexer and a low voltage differential channel.

13. The ultrasound diagnosis apparatus according to claim 1, wherein the probe comprises, an analog front-end controller, an analog-to-digital converter, a field-programmable gate array, and a communication module, and wherein the analog front-end controller comprises a 128 channel analog front-end controller and the analog-to-digital converter comprises a 128 channel analog-to-digital converter.

14. The ultrasound diagnosis apparatus according to claim 1, wherein the probe comprises, an analog front-end controller, an analog-to-digital converter, a field-programmable gate array, and a communication module, and wherein the analog front-end controller, the analog-to-digital converter, and the field-programmable gate array are integrated on a single printed circuit board.

15. The ultrasound diagnosis apparatus according to claim 1, wherein the probe comprises, an analog front-end controller, an analog-to-digital converter, a field-programmable gate array, and a communication module.

* * * * *